US012186004B2

(12) United States Patent
Sprinkle et al.

(10) Patent No.: US 12,186,004 B2
(45) Date of Patent: *Jan. 7, 2025

(54) CONTROL CONSOLE AND ACCESSORIES FOR RF NERVE ABLATION AND METHODS OF OPERATING THE SAME

(71) Applicant: Stryker Corporation, Kalamazoo, MI (US)

(72) Inventors: Thomas Sprinkle, Kalamazoo, MI (US); Habib Baydoun, Kalamazoo, MI (US); Blake Latchford, Saline, MI (US); Edward Crampton, Portage, MI (US)

(73) Assignee: Stryker Corporation, Portage, MI (US)

( * ) Notice: Subject to any disclaimer, the term of this patent is extended or adjusted under 35 U.S.C. 154(b) by 142 days.

This patent is subject to a terminal disclaimer.

(21) Appl. No.: 18/045,626

(22) Filed: Oct. 11, 2022

(65) Prior Publication Data

US 2023/0056660 A1 Feb. 23, 2023

Related U.S. Application Data

(63) Continuation of application No. 16/605,141, filed as application No. PCT/US2018/027917 on Apr. 17, 2018, now Pat. No. 11,497,543.

(Continued)

(51) Int. Cl.
*A61B 18/12* (2006.01)
*A61B 18/14* (2006.01)
*A61B 18/00* (2006.01)

(52) U.S. Cl.
CPC .......... *A61B 18/1206* (2013.01); *A61B 18/14* (2013.01); *A61B 2018/00434* (2013.01);
(Continued)

(58) Field of Classification Search
CPC ..... A61B 18/12; A61B 18/1206; A61B 18/14; A61B 2017/00026; A61B 2017/00084;
(Continued)

(56) References Cited

U.S. PATENT DOCUMENTS 4,785,829 A 11/1988 Convert et al.
5,484,400 A 1/1996 Edwards et al.
(Continued)

FOREIGN PATENT DOCUMENTS

DE 102005007769 B4 9/2008
EP 1301135 A1 4/2003
(Continued)

OTHER PUBLICATIONS

English language abstract and machine-assisted English translation for DE 10 2005 0077 769 extracted from espacenet.com database on Nov. 14, 2019, 8 pages.

(Continued)

*Primary Examiner* — Michael F Peffley
(74) *Attorney, Agent, or Firm* — Howard & Howard Attorneys PLLC

(57) ABSTRACT

Electrosurgical systems and methods are provided for RF nerve ablation, wherein a control console has multiple RF amplifiers associated with multiple channels, and multiple DC power supplies each dedicated to a corresponding one of the RF amplifiers. Each of a plurality of power supply relays are coupled between one of the DC power supplies and the dedicated corresponding one of the RF amplifiers. A controller is configured to apply switching signals to control each of the power supply relays to selectively switch on and off connections between the DC power supplies and the dedicated corresponding RF amplifiers. The controller may apply control signals to each RF amplifier sequentially, one at a time, to deliver energy separately and independently to
(Continued)

each of the corresponding channels. The controller may be configured to apply the switching signals to self-grounding relays to selectively switch on and off connections between the channels and return relays.

20 Claims, 19 Drawing Sheets

Related U.S. Application Data

(60) Provisional application No. 62/491,615, filed on Apr. 28, 2017.

(52) U.S. Cl.
CPC ............... *A61B 2018/00577* (2013.01); *A61B 2018/00654* (2013.01); *A61B 2018/00767* (2013.01); *A61B 2018/00791* (2013.01); *A61B 2018/00875* (2013.01); *A61B 2018/124* (2013.01); *A61B 2018/1273* (2013.01)

(58) Field of Classification Search
CPC ........... A61B 2018/00434; A61B 2018/00577; A61B 2018/00654; A61B 2018/00767; A61B 2018/00791; A61B 2018/00875; A61B 2018/124; A61B 2018/1273
USPC ...................................................... 606/32–34
See application file for complete search history.

(56) References Cited

U.S. PATENT DOCUMENTS

| | | | |
|---|---|---|---|
| 5,693,078 A | 12/1997 | Desai et al. | |
| 5,769,847 A | 6/1998 | Panescu et al. | |
| 5,837,001 A | 11/1998 | Mackey | |
| 5,891,179 A | 4/1999 | Er et al. | |
| 5,931,835 A | 8/1999 | Mackey | |
| 5,954,719 A | 9/1999 | Chen et al. | |
| 5,991,355 A | 11/1999 | Dahlke | |
| 6,071,280 A | 6/2000 | Edwards et al. | |
| 6,162,217 A | 12/2000 | Kannenberg et al. | |
| 6,193,713 B1 | 2/2001 | Geistert et al. | |
| 6,203,541 B1 | 3/2001 | Keppel | |
| 6,266,558 B1 | 7/2001 | Gozani et al. | |
| 6,293,941 B1 | 9/2001 | Strul et al. | |
| 6,306,100 B1 | 10/2001 | Prass | |
| 6,319,249 B1 | 11/2001 | Tollner | |
| 6,346,104 B2 * | 2/2002 | Daly ................. | A61B 18/1477 606/41 |
| 6,350,263 B1 | 2/2002 | Wetzig et al. | |
| 6,387,092 B1 | 5/2002 | Burnside et al. | |
| 6,442,422 B1 | 8/2002 | Duckert | |
| 6,456,088 B1 | 9/2002 | Swale | |
| 6,505,079 B1 | 1/2003 | Foster et al. | |
| 6,558,378 B2 | 5/2003 | Sherman et al. | |
| 6,620,157 B1 | 9/2003 | Dabney et al. | |
| 6,620,186 B2 | 9/2003 | Saphon et al. | |
| 6,638,277 B2 | 10/2003 | Schaefer et al. | |
| 6,666,860 B1 | 12/2003 | Takahashi | |
| 6,752,804 B2 | 6/2004 | Simpson et al. | |
| 6,783,523 B2 | 8/2004 | Qin et al. | |
| 6,796,980 B2 | 9/2004 | Hall | |
| 6,936,047 B2 * | 8/2005 | Nasab ................ | A61B 18/1206 606/34 |
| 6,942,660 B2 | 9/2005 | Pantera et al. | |
| 6,962,587 B2 | 11/2005 | Johnson et al. | |
| 7,048,687 B1 | 5/2006 | Reuss et al. | |
| 7,069,116 B2 | 6/2006 | Kunsman et al. | |
| 7,153,300 B2 | 12/2006 | Goble | |
| 7,163,536 B2 | 1/2007 | Godara | |
| 7,223,264 B2 | 5/2007 | Daniel et al. | |
| 7,226,447 B2 | 6/2007 | Uchida et al. | |
| 7,282,049 B2 | 10/2007 | Orszulak et al. | |
| 7,553,309 B2 | 6/2009 | Buysse et al. | |
| 7,567,840 B2 | 7/2009 | Armstrong | |
| 7,574,257 B2 | 8/2009 | Rittman, III | |
| 7,601,149 B2 | 10/2009 | DiCarlo et al. | |
| 7,699,842 B2 | 4/2010 | Buysse et al. | |
| 7,715,912 B2 | 5/2010 | Rezai et al. | |
| 7,736,358 B2 | 6/2010 | Shores et al. | |
| 7,766,905 B2 | 8/2010 | Paterson et al. | |
| 7,799,021 B2 | 9/2010 | Leung et al. | |
| 7,853,326 B2 | 12/2010 | Rittman, III | |
| 7,901,400 B2 | 3/2011 | Wham et al. | |
| 7,909,820 B2 | 3/2011 | Lipson et al. | |
| 7,942,872 B2 | 5/2011 | Ein-Gal | |
| 7,956,620 B2 | 6/2011 | Gilbert | |
| 7,972,329 B2 | 7/2011 | Refior et al. | |
| 7,974,703 B2 | 7/2011 | Goetz et al. | |
| 8,000,785 B2 | 8/2011 | Rittman, III | |
| 8,012,150 B2 | 9/2011 | Wham et al. | |
| 8,052,675 B2 | 11/2011 | Lorang et al. | |
| 8,062,290 B2 | 11/2011 | Buysse et al. | |
| 8,080,008 B2 | 12/2011 | Wham et al. | |
| 8,100,895 B2 | 1/2012 | Panos et al. | |
| 8,182,477 B2 | 5/2012 | Orszulak et al. | |
| 8,190,258 B2 | 5/2012 | Armstrong | |
| 8,216,220 B2 | 7/2012 | Jensen et al. | |
| 8,265,747 B2 | 9/2012 | Rittman, III et al. | |
| 8,267,928 B2 | 9/2012 | Orszulak et al. | |
| 8,267,929 B2 | 9/2012 | Wham et al. | |
| 8,298,223 B2 | 10/2012 | Wham et al. | |
| 8,303,580 B2 | 11/2012 | Wham et al. | |
| 8,306,629 B2 | 11/2012 | Mioduski et al. | |
| 8,343,146 B2 | 1/2013 | Godara et al. | |
| 8,353,901 B2 | 1/2013 | Rossetto et al. | |
| 8,353,903 B2 | 1/2013 | Podhajsky | |
| 8,398,626 B2 | 3/2013 | Buysse et al. | |
| 8,430,874 B2 | 4/2013 | Newton et al. | |
| 8,486,065 B2 | 7/2013 | Lee et al. | |
| 8,500,729 B2 | 8/2013 | Bystryak et al. | |
| 8,532,773 B2 | 9/2013 | Armstrong | |
| 8,556,890 B2 | 10/2013 | Wham | |
| 8,560,062 B2 | 10/2013 | Rittman, III et al. | |
| 8,603,082 B2 | 12/2013 | Lorang et al. | |
| 8,613,743 B2 | 12/2013 | Selig | |
| 8,624,606 B2 | 1/2014 | Gilbert | |
| 8,628,523 B2 | 1/2014 | Rossetto et al. | |
| 8,639,351 B2 | 1/2014 | Parker et al. | |
| 8,653,994 B2 | 2/2014 | Smith | |
| 8,734,438 B2 | 5/2014 | Behnke | |
| 8,771,269 B2 | 7/2014 | Sherman et al. | |
| 8,814,855 B2 | 8/2014 | DiCarlo et al. | |
| 8,818,503 B2 | 8/2014 | Rittman, III | |
| 8,825,158 B2 | 9/2014 | Swerdlow | |
| 8,852,182 B2 | 10/2014 | Tullis et al. | |
| 8,905,926 B2 | 12/2014 | Colombo et al. | |
| 8,918,184 B1 | 12/2014 | Torgerson et al. | |
| 8,956,347 B2 | 2/2015 | Lorang et al. | |
| 9,002,465 B2 | 4/2015 | Ranu | |
| 9,005,193 B2 | 4/2015 | Govari et al. | |
| 9,008,793 B1 | 4/2015 | Cosman, Sr. et al. | |
| 9,023,029 B2 | 5/2015 | Honda et al. | |
| 9,033,973 B2 | 5/2015 | Krapohl et al. | |
| 9,037,259 B2 | 5/2015 | Mathur | |
| 9,072,539 B2 | 7/2015 | Messerly et al. | |
| 9,082,273 B2 | 7/2015 | Mohn et al. | |
| 9,089,360 B2 | 7/2015 | Messerly et al. | |
| 9,113,888 B2 | 8/2015 | Orszulak et al. | |
| 9,113,912 B1 | 8/2015 | Mehta et al. | |
| 9,119,628 B1 | 9/2015 | Mehta et al. | |
| 9,155,583 B2 | 10/2015 | Bek et al. | |
| 9,168,054 B2 | 10/2015 | Turner et al. | |
| 9,168,091 B2 | 10/2015 | Janssen et al. | |
| 9,192,308 B2 | 11/2015 | Brannan et al. | |
| 9,198,710 B2 | 12/2015 | Honda et al. | |
| 9,277,955 B2 | 3/2016 | Herscher et al. | |
| 9,283,031 B2 | 3/2016 | Janssen et al. | |
| 9,301,802 B2 | 4/2016 | Rossetto et al. | |
| 9,333,034 B2 * | 5/2016 | Hancock ............. | A61B 18/042 |
| 9,339,324 B2 | 5/2016 | Eisele et al. | |
| 9,364,277 B2 | 6/2016 | Sisken et al. | |

(56) References Cited

U.S. PATENT DOCUMENTS

| | | |
|---|---|---|
| 9,421,385 B2 | 8/2016 | Vijayagopal et al. |
| 9,463,326 B2 | 10/2016 | Ranu |
| 9,474,564 B2 | 10/2016 | Behnke et al. |
| 9,504,855 B2 | 11/2016 | Messerly et al. |
| 9,545,521 B1 | 1/2017 | Torgerson et al. |
| 9,579,503 B2 | 2/2017 | McKinney et al. |
| 10,363,084 B2 | 7/2019 | Friedrichs |
| 2001/0020166 A1 | 9/2001 | Daly et al. |
| 2002/0156472 A1 | 10/2002 | Lee et al. |
| 2003/0014087 A1 | 1/2003 | Fang et al. |
| 2003/0181898 A1* | 9/2003 | Bowers .............. A61B 18/1206 606/34 |
| 2003/0187430 A1* | 10/2003 | Vorisek .................. A61B 18/14 606/41 |
| 2003/0212394 A1 | 11/2003 | Pearson et al. |
| 2004/0006264 A1 | 1/2004 | Mojarradi et al. |
| 2004/0267252 A1 | 12/2004 | Washington et al. |
| 2005/0096644 A1 | 5/2005 | Hall et al. |
| 2006/0079887 A1 | 4/2006 | Buysse et al. |
| 2006/0161148 A1 | 7/2006 | Behnke |
| 2007/0032835 A1 | 2/2007 | Rittman |
| 2007/0066971 A1 | 3/2007 | Podhajsky |
| 2007/0129716 A1 | 6/2007 | Daw et al. |
| 2007/0203481 A1 | 8/2007 | Gregg et al. |
| 2007/0255269 A1 | 11/2007 | Shin |
| 2007/0282321 A1 | 12/2007 | Shah et al. |
| 2008/0183169 A1 | 7/2008 | Klimovitch et al. |
| 2008/0249523 A1 | 10/2008 | McPherson et al. |
| 2008/0281322 A1 | 11/2008 | Sherman et al. |
| 2009/0138061 A1 | 5/2009 | Stephens et al. |
| 2011/0160718 A1 | 6/2011 | Werner |
| 2011/0172656 A1 | 7/2011 | Schall et al. |
| 2011/0270120 A1 | 11/2011 | McFarlin et al. |
| 2011/0306960 A1 | 12/2011 | Eisele et al. |
| 2012/0215213 A1 | 8/2012 | Juzkiw et al. |
| 2012/0310298 A1 | 12/2012 | Besio et al. |
| 2013/0023873 A1 | 1/2013 | Danek et al. |
| 2013/0116752 A1 | 5/2013 | Parker et al. |
| 2014/0052130 A1 | 2/2014 | Park et al. |
| 2014/0088593 A1 | 3/2014 | Van Wyk et al. |
| 2014/0135760 A1 | 5/2014 | Cadouri et al. |
| 2014/0258800 A1 | 9/2014 | Gilbert |
| 2014/0316404 A1 | 10/2014 | Neumann et al. |
| 2014/0330266 A1 | 11/2014 | Thompson et al. |
| 2014/0350541 A1 | 11/2014 | Hill et al. |
| 2015/0105701 A1 | 4/2015 | Mayer et al. |
| 2015/0241505 A1 | 8/2015 | Freeman et al. |
| 2015/0265333 A1 | 9/2015 | Shin et al. |
| 2015/0282861 A1 | 10/2015 | Anderson et al. |
| 2015/0297282 A1 | 10/2015 | Cadouri |
| 2016/0206362 A1 | 7/2016 | Mehta et al. |
| 2016/0206363 A1 | 7/2016 | Mehta et al. |
| 2016/0213425 A1 | 7/2016 | Rossetto et al. |
| 2016/0256219 A1 | 9/2016 | Lee et al. |
| 2016/0287311 A1 | 10/2016 | Friedrichs |
| 2017/0049513 A1 | 2/2017 | Cosman, Jr. et al. |
| 2017/0050021 A1 | 2/2017 | Cosman, Sr. |
| 2017/0050038 A1 | 2/2017 | Cosman et al. |
| 2017/0056093 A1 | 3/2017 | Cosman |
| 2020/0078083 A1 | 3/2020 | Sprinkle et al. |

FOREIGN PATENT DOCUMENTS

| | | |
|---|---|---|
| EP | 1372505 A1 | 1/2004 |
| EP | 1545360 A1 | 6/2005 |
| EP | 1645234 A1 | 4/2006 |
| EP | 1649821 A1 | 4/2006 |
| EP | 1810625 A1 | 7/2007 |
| EP | 2112908 A1 | 11/2009 |
| EP | 2510895 A1 | 10/2012 |
| EP | 2653128 A1 | 10/2013 |
| JP | S62139673 A | 6/1987 |
| JP | 2006296490 A | 11/2006 |
| JP | 2007296304 A | 11/2007 |
| JP | 2014534856 A | 12/2014 |
| WO | 9600036 A1 | 1/1996 |
| WO | 9634567 A1 | 11/1996 |
| WO | 0207627 A1 | 1/2002 |
| WO | 02080784 A1 | 10/2002 |
| WO | 2004032777 A1 | 4/2004 |
| WO | 2004047565 A1 | 6/2004 |
| WO | 2004073536 A1 | 9/2004 |
| WO | 2006096475 A1 | 9/2006 |
| WO | 2008101356 A1 | 8/2008 |
| WO | 2013134133 A1 | 9/2013 |

OTHER PUBLICATIONS

English language abstract and machine-assisted English translation for JP 2006-296490 A extracted from espacenet.com database on Mar. 28, 2022, 17 pages.

English language abstract and machine-assisted English translation for WO 2004/047565 extracted from espacenet.com database on Nov. 14, 2019, 7 pages.

English language abstract for JP 2007-296304 A extracted from espacenet.com database on Mar. 28, 2022, 2 pages.

International Search Report for Application No. PCT/US2018/027917 dated Oct. 29, 2018, 5 pages.

Machine-assisted English language abstract or JP 2014-534856 A extracted from espacenet.com database on Mar. 28, 2022, 2 pages.

Machine-assisted English language abstract or JPS 62-139673 A extracted from espacenet.com database on Mar. 28, 2022, 2 pages.

Morgan Automation LTD, "Neurotherm Radio Frequency Lesion Generator Model NT 1000 Service Manual", Jun. 2006, 111 pages.

Neurotherm, "Neurotherm Radio Frequency Lesion Generator Model NT 1100 Operators Manual", Sep. 2008, 97 pages.

Partial International Search Report for Application No. PCT/US2018/027917 dated Jul. 9, 2018, 3 pages.

Stryker Instruments, "Inteventional Spine (IVS) RF Multigen Generator Ref 0406-900-702, Rev. D, Instructions for Use", Jul. 1, 2008, pp. 1-65.

Youtube, "Stryker Corporation Interventional Spine Multi-Gen Monopolar Procedure Animation Video", Sep. 28, 2009, https://youtu.be/TulVN_O-xDk, 1 page.

* cited by examiner

CONTROL CONSOLE AND ACCESSORIES FOR RF NERVE ABLATION AND METHODS OF OPERATING THE SAME

CROSS-REFERENCE TO RELATED APPLICATIONS

This is a continuation of U.S. application Ser. No. 16/605,141, filed Oct. 14, 2019, issued as U.S. Pat. No. 11,497,543, which is a national entry of International Application No. PCT/US2018/027917, filed Apr. 17, 2018, which claims priority to and all the benefits of U.S. Provisional Patent Application No. 62/491,615, filed Apr. 28, 2017, the entire disclosure of each being hereby incorporated by reference.

TECHNICAL FIELD

The present disclosure relates to electrosurgical consoles for performing radio frequency (RF) nerve ablation and methods and accessories associated with the same.

BACKGROUND

RF energy is commonly utilized to ablate diseased sensory nerves for the purposes of treating nerve based pain. Conventionally, an electrosurgical console having a single RF amplifier delivers the RF energy through multiple channels to electrodes connected to the control console. The electrodes are placed at the treatment location and application of the RF energy through the electrodes creating RF lesions, and thereby causing ablation of the diseased nerves.

One shortcoming of electrosurgical consoles stems from the limitations of using the single RF amplifier. Comprehensive relief of the patient's pain often requires the treatment of multiple locations. For example, the majority of RF nerve ablation procedures involve lesioning three or more distinct locations. Procedural efficiency dictates the treatment of the multiple locations in a concurrent manner. There exists RF nerve ablation systems that feature concurrent treatment of multiple locations through the use of multiple channels. Such systems, however, commonly utilize a single RF amplifier shared among the multiple channels. Temperature feedback for each channel enables the use of closed loop control in order to regulate the delivery of RF energy to each treatment location.

There are two fundamental approaches to creating RF lesions in multiple locations in a concurrent manner through the use of a single RF amplifier. Lesioning of multiple nerve locations by this single RF amplifier may be accomplished by either the application of the output energy from the single RF amplifier to multiple locations simultaneously, or by non-simultaneous application of the single RF amplifier output energy to multiple locations via sequential time-slicing. Although treating multiple locations, both techniques are limited to use of the single RF amplifier. With the single RF amplifier, there are disadvantages to both the simultaneous energy delivery method as well as the non-simultaneous time-sliced delivery method.

Simultaneous application of RF energy to multiple locations from the single RF amplifier results in only limited ability to control the RF energy delivered to each location. The power delivered to each location is strongly influenced by the patient-circuit impedance from each location to the common return location. The power level required to effectively treat each lesion location is influenced by normally occurring anatomical variation present in all patients such as blood vessels. Fully independent control of each channel is not possible with this method. In order for all channels to achieve their respective set temperature, the output power level must be set to the level required by the most demanding location. A single control loop is used to regulate the RF output amplitude. Control specific to each channel is limited to a simple ON/OFF selection for treatment location.

While non-simultaneous energy delivery makes fully independent control loops possible, practical implementations of non-simultaneous time-slicing from a single RF amplifier is limited by the requirement to utilize mechanical relays to steer the RF output waveform to the various channels. Reliable operation dictates the need to stop RF output before switching relay states and not resume RF output until the relay contacts have settled to the new state. Time-slice switching between channels is thereby limited to relatively low frequencies. For instance, certain control consoles feature channel output cycling around 2 Hertz. Such low frequency switching of RF output energy from the single RF amplifier increases the likelihood of unwanted patient stimulation in the form of inadvertent neuromuscular stimulation. The relatively long off-time that occurs during the low frequency cycling increases the difficulty in heating lesion locations up to treatment temperature. Another shortcoming associated with non-simultaneous time-slicing from a single RF Amplifier are the practical limitations associated with instantaneously changing the magnitude of the RF amplifier output power level when switching between channels.

Another disadvantage of conventional electrosurgical consoles stems from the inability of conventional consoles to verify proper delivery of stimulation energy to the patient. Safety and efficacy of the nerve ablation procedure is highly dependent upon proper placement of the electrodes at the treatment location. The electrode must be placed proximal to the nerve to be ablated, otherwise the procedure's effectiveness will be diminished. Likewise it is important that the electrode not be placed proximal to motor nerves or other tissue to be avoided, otherwise the patient may experience loss of motor function or another adverse side effect associated with lesioning in the wrong location.

Placement of the electrode is facilitated through the use of visualization guidance, and most commonly C-arm x-ray fluoroscopy. While bony structures and the metallic electrodes are visualized quite well by x-ray imaging equipment, nerve fibers are not visible with this imaging technology. Bony structures, visible under fluoroscopy, serve as the navigational landmarks to direct the placement of the electrodes proximal to nerve pathways that are well established.

Secondary to visualization guidance, patient feedback from electrical stimulation applied to each electrode may be utilized during the electrode placement process as a supplemental means of confirming proper electrode placement. There are two distinct forms of electrical stimulation i.e., sensory nerve stimulation and motor nerve stimulation. Electrosurgical consoles enable selection of sensor or motor waveforms and selection of the desired amplitude of the selected stimulation. Patient response provides the user with an ancillary means of evaluating electrode placement.

Sensory nerve stimulation is optimized to elicit a sensory nerve response. Proximity to sensory nerves that have been selected for ablation may be assessed through the application of sensory nerve stimulation to the electrode. On the other hand, motor nerve stimulation is optimized to elicit a motor nerve response. Clearance from motor nerves that must be avoided may be assessed through the application of motor nerve stimulation to the electrode.

With conventional electrosurgical consoles, it is possible for an undetected hardware fault to occur that would inhibit the selected waveform from reaching the patient. If a fault in the motor stimulation circuitry or waveform routing circuitry is undetected, it is possible that a physician may proceed with a nerve ablation procedure based upon faulty patient feedback. This condition may lead to an increased risk of inadvertent motor nerve impairment.

Moreover, management of attachment cables for conventional electrosurgical consoles has proven to be difficult. Different types of electrodes and electrode configurations exist for performing nerve ablation with electrosurgical consoles. Examples include monopolar electrodes, bipolar self-grounding electrodes and dual-monopolar electrodes operating in a parallel bipolar fashion. The different types of electrodes and electrode configurations often require changing of an attachment cable that couples one or more of the electrodes to one of several different combinations of channels of the electrosurgical console. Bipolar self-grounding electrodes have provided a particular challenge. Whereas monopolar electrodes utilize one channel of the electrosurgical console, bipolar self-grounding electrodes utilize two channels of the electrosurgical console. Changing the attachment cable for proper operation of bipolar self-grounding attachments is particularly onerous. The need to change attachment cables in order to match attached accessories has proven to increase the occurrence of use errors. Moreover, it is also well known that attachment cables have a tendency to be misplaced once disconnected from the electrosurgical console.

Furthermore, although bipolar self-grounding electrodes utilize two channels of the electrosurgical console, each bipolar self-grounding electrode is limited to creating a single lesion in a single location. Electrosurgical consoles are usually equipped with no more than four channels for practical reasons. Hence, the use of bipolar self-grounding electrodes limits the ability of the electrosurgical console to perform no more than two bipolar self-grounding lesions at any given time.

Yet another shortcoming of conventional electrosurgical consoles resides in the inability to track and display data associated with electrodes or cable accessories that are utilized by the console. It is known to embed an electronic device (e.g., an electrically erasable programmable read only memory or EEPROM) into a medical device accessory for the purposes of authentication and/or use metering. For example, the electronic device serves to identify the accessory to the main unit to which the accessory is connected. The electronic device typically includes a writeable portion that functions as a use meter. If the accessory is not identified as a supported accessory, then the main unit disables operation with the attached accessory. Upon use of the accessory, the main unit writes to the embedded device, effectively marking the accessory as "used" in order to prohibit the future use of accessories that are intended to be single patient use only.

In the field of nerve ablation, it is known to provide electrodes having a connector containing an EEPROM having an authentication section and an odometer data structure. If the authentication code is not identified by the electrosurgical console as a supported accessory, then the electrosurgical console disables operation with that attached electrode.

Some electrosurgical consoles are configured to read the electrode's use data and provide a warning message to the user that the attached accessory may be approaching the end of its useful life after the odometer had been incremented to a predetermined value. However, the odometer value is never displayed to the user and the data is not stored on electrosurgical console. Therefore, once the electrode is disconnected from the electrosurgical console, the use data, as well as the authentication and identification data are immediately lost. The issue is exacerbated by the fact that a healthcare facility may have dozens of each type of electrode in their inventory. Therefore, users of conventional electrosurgical consoles have no practical way of tracking and displaying data associated with electrodes that are or have been connected to the console. Tracking of authentication and usage data for cable accessories in the field of nerve ablation is virtually non-existent.

As such, there remains a need to address at least the aforementioned problems surrounding conventional electrosurgical consoles and their accessories.

SUMMARY

An example method for controlling a control console configured for RF nerve ablation is provided. The control console comprises a plurality of channels and a plurality of RF amplifiers each dedicated for delivering energy to a corresponding one of the channels, and a controller coupled to the RF amplifiers. The method comprises generating, with the controller, control signals for separately and independently controlling each of the RF amplifiers. The controller sequentially applies the control signals to each RF amplifier, one at a time, for delivering energy to the corresponding channel.

An example of a control console is configured for radio frequency (RF) nerve ablation is provided. The control console comprises a plurality of channels. A plurality of RF amplifiers are each dedicated to deliver energy to a corresponding one of the channels. A controller coupled to the RF amplifiers and being configured to generate control signals to separately and independently control each of the RF amplifiers and to apply the control signals to each RF amplifier sequentially, one at a time, to deliver energy to the corresponding channel.

One example of a cable accessory is provided. The cable accessory is configured to interconnect a monopolar electrode attachment and/or a bipolar self-grounding electrode attachment to a control console. The control console is configured to energize one or more of the electrode attachments through one or more channels to perform RF nerve ablation. The cable accessory comprises a first interface configured to couple to the control console and a second interface configured to couple to the monopolar electrode attachment and/or the bipolar self-grounding electrode attachment. The cable accessory comprises an output circuit path coupled between the first and second interfaces to accommodate signal output from one channel of the control console to the monopolar electrode attachment or the bipolar self-grounding electrode attachment, depending on which electrode attachment is coupled to the second interface. A first return circuit path is coupled between the first and second interfaces to accommodate signal return from the bipolar self-grounding electrode attachment to the one channel of the control console.

Another example of a cable accessory is provided. The cable accessory is configured to interconnect one or more electrode attachments to a control console. The control console is configured to energize the one or more electrode attachments through one or more channels to perform RF nerve ablation. The cable accessory comprises a first interface configured to couple to the control console and a second interface configured to couple to the one or more electrode attachments. A circuit is coupled between the first and second interfaces and comprises a switch arrangement being controllable to select one or more of a plurality of electrical path configurations between the first and second interfaces thereby to accommodate interconnection between the one or more electrode attachments and the one or more channels of the control console.

Another example of a control console configured for RF nerve ablation is provided. The control console comprises a display, a controller, one or more processors and an interface. The interface is configured to receive attachments adapted for RF nerve ablation and to facilitate connection between a memory device of each attachment and the controller. Each memory device has stored thereon identification data identifying the attachment and usage data identifying usage of the attachment. The control console comprises a non-transitory memory having stored thereon instructions, which when executed by the one or more processors, are configured to read and store the identification and usage data associated with the attachments received at the interface. The stored identification and usage data is processed. The instructions, when executed, generate a digital representation of the processed identification and usage data for the display.

Another example of a method for operating a control console configured for RF nerve ablation is provided. The control console comprises a display, a controller, and an interface configured to receive attachments adapted for RF nerve ablation. Each attachment comprises a memory device having stored thereon identification data identifying the attachment and usage data identifying usage of the attachment. The method comprises the control console performing the steps of reading the identification and usage data associated with the attachments from the memory devices and storing the identification and usage data. The stored identification and usage data is processed. The control console generates a digital representation of the processed identification and usage data and displays the digital representation with the display.

Yet another example of a control console configured for RF nerve ablation is provided. The control console comprises a stimulation generator configured to output a stimulation signal and a calibration element configured to receive the stimulation signal. A sensing circuit is configured to generate a reading based on the calibration element receiving the stimulation signal. A controller coupled to the sensing circuit is configured to analyze the reading and to calibrate the sensing circuit based on analysis of the reading.

Yet another example of a method for operating a control console configured for RF nerve ablation is provided. The control console comprises a stimulation generator, a calibration element, a sensing circuit and a controller. The method comprises outputting a stimulation signal with the simulation generator and receiving the stimulation signal with the calibration element. The sensing circuit generates a reading based on the calibration element receiving the stimulation signal. The controller analyzes the reading and calibrates the sensing circuit based on analysis of the reading.

Advantages of the control console, cable accessory, and methods described herein, as well as the examples of the same, will be understood in reference to the description provided herein.

DETAILED DESCRIPTION

I. Overview

Figure 1:
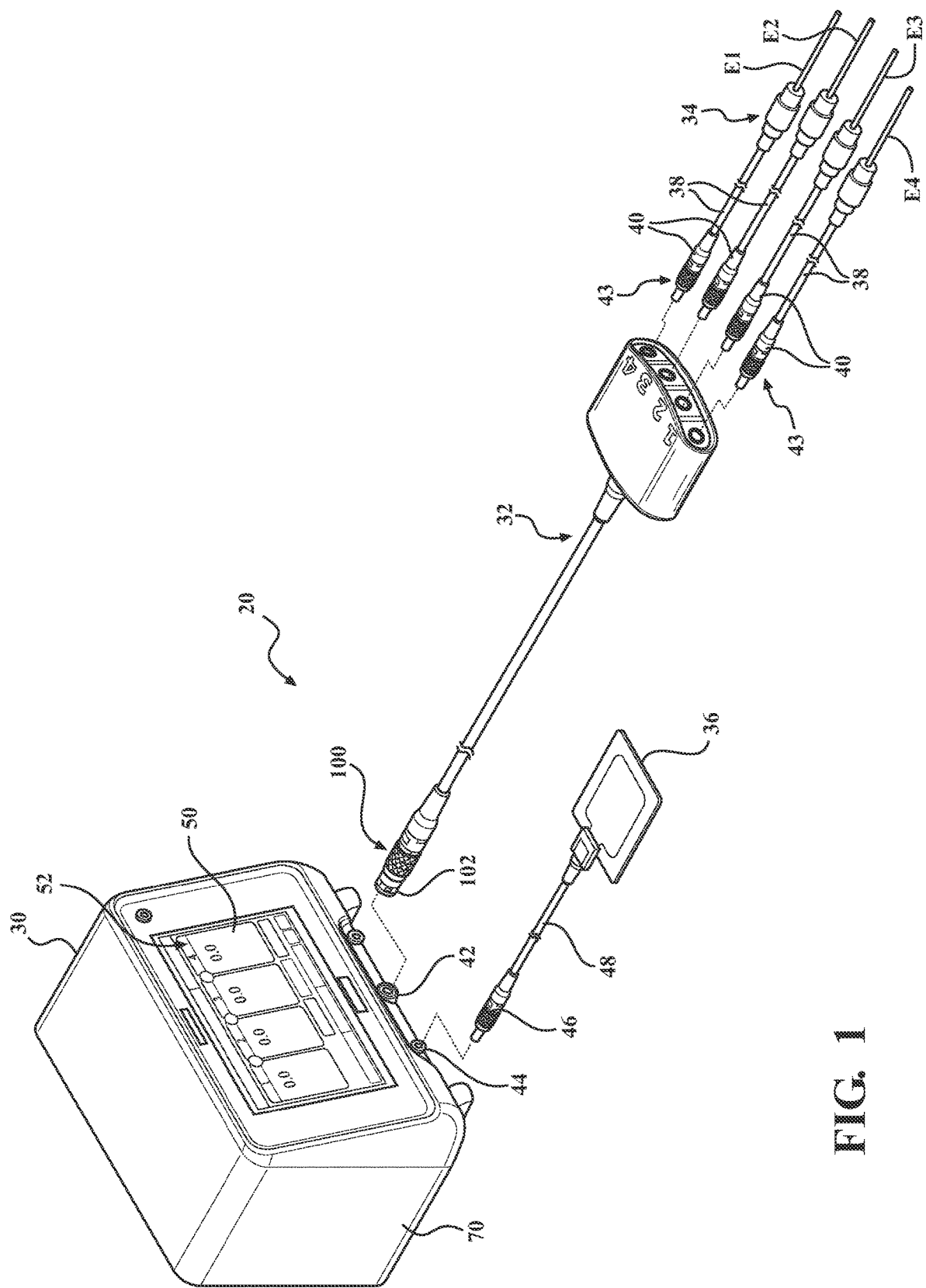
FIG. 1 is a perspective assembly view of one example of an electrosurgical system for RF nerve ablation comprising a control console having connectable thereto a ground pad assembly and a cable accessory connectable to one or more electrode attachments.

Referring to the Figures, wherein like numerals indicate like or corresponding parts throughout the several views, an electrosurgical system 20 is provided having a control console 30 and a cable accessory 32 being configured to connect the control console 30. Referring to FIG. 1, one or more electrode assemblies 34 having electrodes E1-E4 are configured to connect to the control console 30, either directly or through the cable accessory 32. A ground pad 36 may be connected to the control console 30 in certain configurations, as will be described below. Methods of operating the electrosurgical system 20, the control console 30, and the cable accessory 32 additionally are described herein.

The electrosurgical system 20 is configured for RF treatment or modification of patient tissue, and specifically nerves, such as nerves in the spinal area of the patient. The control console 30 generates electrical energy of a controlled radiofrequency and passes this energy through one or more of the electrodes E1-E4.

In one example, which is a pain management procedure, the electrosurgical system 20 is utilized to modify nerve cells to the point at which the nerve cells no longer function. The modification of nerve cells results in the formation of a lesion. The control console 30 applies temperature-controlled, RF energy into targeted nerve tissue to the electrode assembly 24.

The electrosurgical system 20 may also be used in "pulsed mode." Instead of creating heat lesions, RF energy is pulsed with a duty cycle low enough that tissue temperature rise is kept below a level that is lethal to cells. Pain relief is accomplished by altering the nerve tissue through a pulsed electromagnetic field created by the pulsed RF energy, which in turn influences gene expression in the nerves.

The electrosurgical system 20 may be utilized for pain relief procedures relating to any suitable part of the patient that includes nerves that may require pain relief including lumbar, thoracic, and cervical regions of the spinal cord, peripheral nerves, and nerve roots. Examples include, but are not limited to, Facette Denervation, Percutaneous Chordotomy/Dorsal Root Entry Zone (DREZ) Lesion, Trigeminus Neuralgia, and Rhizotomy.

Each electrode assembly 34 delivers the RF energy to a targeted nerve tissue area of a patient. In one example, each electrode assembly 34 comprises a cannula (not shown) in addition to the respective electrode E1-E4. The cannula has an exposed tip and is configured to pierce and penetrate skin and tissue to percutaneously position the exposed tip of the cannula with respect to a nerve targeted. Upon completion of the procedure, the cannula may be discarded. The cannula may also facilitate connection of a syringe (not shown) for localized injection of an anesthetic. Once the targeted nerve tissue is properly medicated, the syringe is removed from the cannula and the cannula remains in the tissue. Each electrode E1-E4 may also be equipped with a temperature sensing device (not shown) for sensing temperature at the target site. In one example, the temperature sensing device is a thermocouple.

Referring to FIG. 1, each electrode E1-E4 is connectable to a first end of a cable 38. The cable 38 comprises a connector 40 at an opposing second end. The connector 40 is removably connectable directly to the control console 30 or to the cable accessory 32. The combination of each electrode E1-E4 and its corresponding cable 38 and connector 40 is herein referred to as an electrode attachment 43. It is to be appreciated that the cable 38 and connector 40 may be integrally formed or separate, detachable parts. Similarly, the electrode E1-E4 may be integrated into the cable 38 or may be a separate, detachable part. Internal to the cable 38 are a plurality of insulated conductors for facilitating transmission of electrical energy for purposes, which will be described below. The cable accessory 32 will also be described in detail in later sections.

Although four electrodes E1-E4 are shown in FIG. 1, it is to be appreciated that any suitable number of electrodes E may be utilized. Additionally, the cable accessory 32 may or may not be used, depending on the configuration of the control console 30 and the ability of to directly connect the electrode attachments 43 to the control console 30.

Examples of electrode assemblies, cannulae, temperature sensing devices, and attachments for electrodes are disclosed in U.S. Pat. No. 8,852,182, granted on Oct. 7, 2014 and entitled "Electrode Assembly with Separate Bipolar Cannula and Supply Electrode," the disclosure of which is hereby incorporated by reference in its entirety.

The control console 30, in FIG. 1, comprises a first connection interface 42 configured to connect to the electrodes E1-E4. More specifically, the first connection interface 42 is configured to receive the cable accessory 32 to which any of the electrodes E1-E4 are connected. In instances where the cable accessory 32 is not utilized, the control console 30 may alternatively be configured to comprise a plurality of connection interfaces each for separately connecting to only one electrode E1-E4. The control console 30 further comprises a second connection interface 44 configured to connect to the ground pad 36, and more specifically to a connector 46 of a cable 48 connected to the ground pad 36.

The control console 30, as shown in FIG. 1, comprises a display device 50 configured to display a graphical user interface (GUI) 52 for enabling the user, among other things, to select operating parameters and to navigate through different modes of operation provided by software on the control console 30. The display device 50, in one example, is a touch screen device, such as an LCD touch screen, enabling selection of digital buttons represented on the display device 50 using the location of a touching (e.g., capacitively sensed) on the screen. In some examples, the display device 50 may be paired with and aligned with a separate touch screen device. Additionally, the display device 50 may sense pressure applied from a touch to enable advanced or secondary functions or as an added measure of redundancy before activating certain features, such as energization of electrical energy through any of the electrodes E1-E4. Alternatively, the GUI 52 may be controlled by peripheral input devices connected to the control console 30, such as a mouse and keyboard.

The modes selectable on the GUI 52 include a sensory nerve stimulation mode, a motor nerve stimulation mode, and a lesion mode. The sensory nerve stimulation mode is selected from the GUI 52 to enable the control console 30 to elicit a sensory nerve response by applying a sensory stimulation signal through any of the electrodes E1-E4. Proximity to sensory nerves that have been selected for treatment may be assessed through the application of sensory nerve stimulation to the given electrode(s) E1-E4. Examples of parameters of the sensory stimulation signal that may be selected from the GUI 52 include amplitude (volts) and time duration (e.g., 2 seconds) of application of the stimulation signal. Furthermore, the GUI 52 may display an impedance (Ohms) of the signal path defined from the first connection interface 42 of the control console 30, through the cable accessory 32 (if applicable), the electrode attachment 43 (including the electrode), the patient, and returning through the ground pad 36 back to the second connection interface 44 of the control console 30. Additional features of impedance measurement and analysis are described below.

The motor nerve stimulation mode is selected from the GUI 52 to enable the control console 30 to elicit a motor nerve response by applying a motor stimulation signal. Clearance from motor nerves that must be avoided may be assessed through the application of motor stimulation signal to the electrode E1-E4. Amplitude and application duration of the motor stimulation signal may be selectable from the GUI 52 and impedance during application of the motor stimulation signal may be monitored and displayed on the GUI 52.

The lesion mode is selected from the GUI 52 to enable the control console 30 to generate the RF output signal to any of the electrodes E1-E4 for treating the target nerve. The lesion mode comprises two sub-modes, i.e., the thermal mode and the pulsed mode. The thermal mode is designed to ablate the target site for eliminating nerve function. Examples of settings for the thermal mode that are selectable from the GUI 52 include the desired temperature to apply at the target nerve (e.g., 80 degrees Celsius) and the desired time duration of application of the RF output (e.g., 90 seconds). The pulsed mode is configured to treat sensitive nerves without eliminating nerve function. Examples of settings for the pulsed mode that are selectable from the GUI 52 include the RF voltage (e.g., variable or 30-75 volts), the RF pulse parameters such as frequency (e.g., 2 Hz-50 Hz) and the respective pulse width (e.g., 2 ms, 4 ms, 10 ms, 20 ms, 100 ms, etc.). Those skilled in the art appreciate that the thermal and pulsed modes may be combined or separate. Furthermore, the thermal mode may comprise RF output signals comprising pulses and the pulsed mode may be configured to deliver RF output signals that are configured for thermal ablation. Modes for RF ablation other than those described herein may also be utilized. It is to be appreciated that various other features may be provided by the GUI 52 other than those described herein. Additionally, the GUI 52 may have any configuration or design for enabling any of the features or selections described herein.

Figure 2:
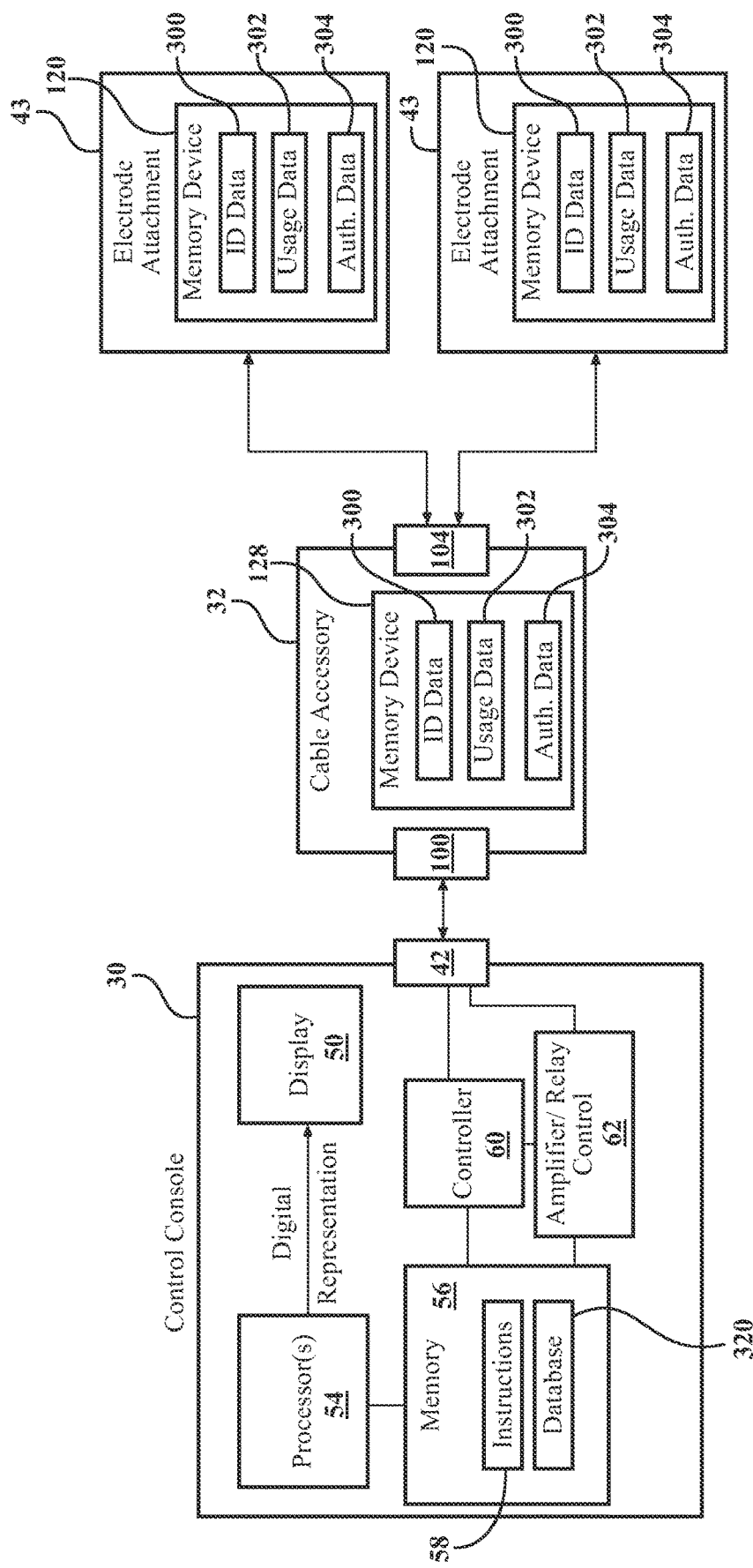
FIG. 2 is a block diagram of certain components and features of the control console, cable accessory, and one or more electrode attachments.

Referring to FIG. 2, the control console 30 comprises one or more processors 54 and one or more memory devices 56. Computer-executable instructions 58 or code may be stored on the one more memory devices 56. The instructions 58 are accessible by the one or more processors 54, and when executed by the one or more processors 54 are configured to implement various functions of the control console 30. For example, the instructions, when executed are configured to implement the GUI 52 on the display 50. Various other functions implemented by execution of the instructions are described below. The processor(s) 54 and memory device(s) 56 may have any suitable configuration and may be any suitable type to enable implementation of the functions described herein.

The control console 30 may comprise a controller 60, which in one example is implemented by the processor(s) 54. Alternatively, the controller 60 may be device separate from the processor(s) 54. That is, the controller 60 may execute the instructions 58 stored in memory 56 and/or may execute its own instructions, e.g., stored in programmable ROM, RAM, or flash memory internal to the controller 60 chipset, for example. For example, the controller 60 may comprise a microcontroller or MCU having any suitable number of bits, e.g., 32 bits. In one example, the controller 60 implements a motherboard of the control console 30, which is capable of reading measurement values and sensing signals from the electrodes E1-E4, providing the requisite stimulation or RF output signals to the electrodes E1-E4, implementing temperature control loops and impedance measurement control, configuring variable power supplies, identifying electrode attachments 43 and connection configurations, and providing communication with peripherals of the control console 30, such as the display 50, speakers, and controlling devices configured for other communication such as wireless, Ethernet, or USB-based communication. Functions other than those described herein may be implemented by the controller 60. Additionally, any of the functions described herein may be implemented by the controller 60, one or more processors 54 or a combination thereof.

Referring back to FIG. 2, the control console 30 further comprises an amplifier/relay section 62. This section 62 may comprise an amplifier section 64 and a relay section 66. The amplifier and relay sections 64, 66 may be separate sections or integrated into a common section or board. Furthermore, the amplifier and relay sections 64, 66 may be combined into a single controller or control system. These sections 64, 66 may be controlled by any suitable component or sub-system, such as the controller 60. The amplifier section 64 is coupled to the controller 60 and is configured to provide several different RF amplifiers 68, which are controllable to generate the desired or specified RF output signal through variable power supply provided from the controller 60. The relay section 66 is configured to with various relays for directing electrical pathways for power supply control, RF amplifier 68 output control, RF amplifier 68 return control, impedance calibration and control, stimulation calibration and control, ground pad 36 testing, and specialized electrode attachment 43 return paths (e.g., self-grounding bipolar electrodes). The amplifier/relay control section 62 is described in detail below.

Referring to FIG. 1, the control console 30 comprises a housing 70. In one example, the processor(s) 54, memory 56, controller 60, and amplifier/relay control section 62 are disposed within the housing 70. The display 50, the connection interface 42 for the cable accessory 32/electrodes E1-E4, and the interface 43 for the ground pad 36 are coupled to the housing 70 and exposed to an exterior of the housing 70 to enable user interaction therewith. Depending on the configuration and functionality of the control console 30, some of the described components alternatively may be located remote from the control console 30 and implemented by a separate device that is connects to or otherwise is in communication with the control console 30.

Figure 3:
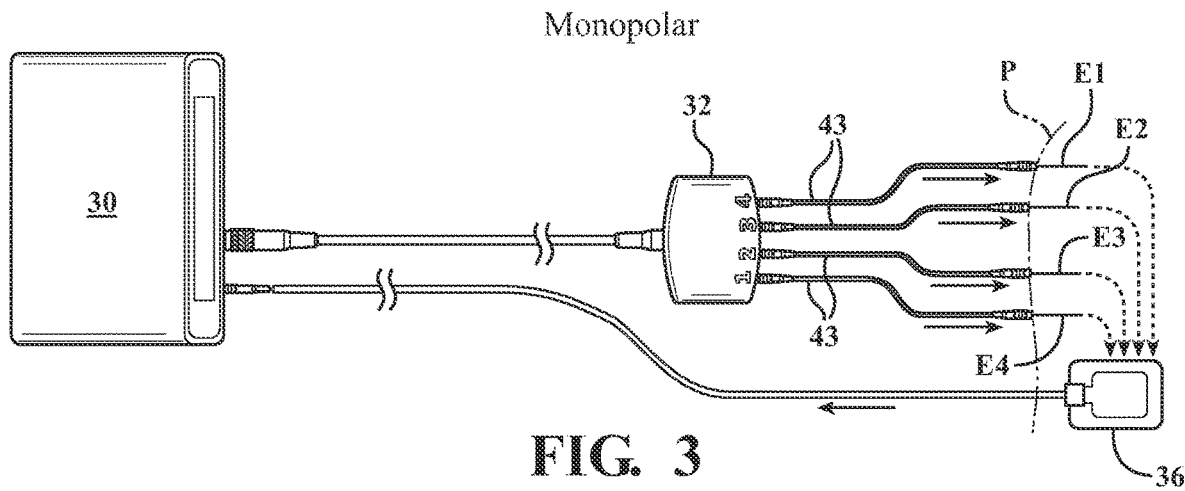
FIG. 3 is diagram illustrating flow of RF output signals generated by the control console in an example where the electrode attachments are monopolar and are operating in a monopolar mode.
Figure 4:
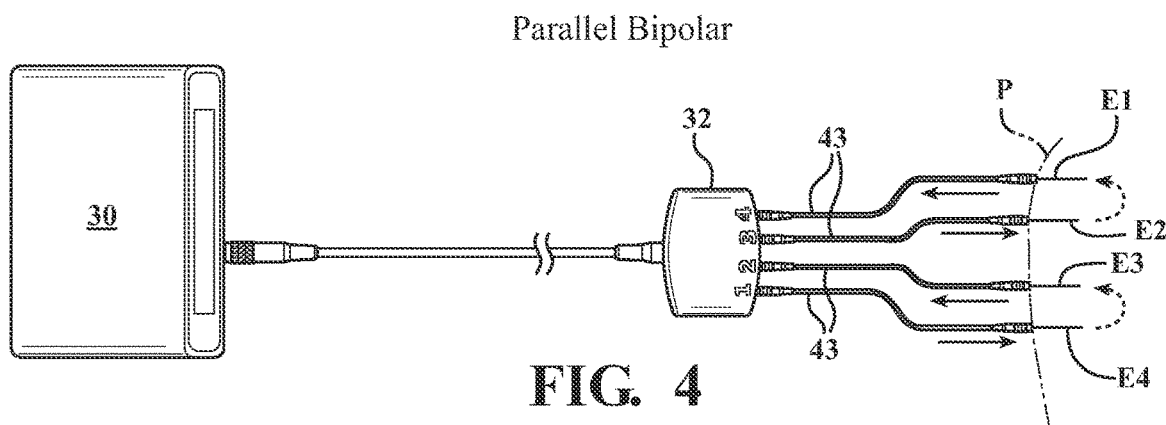
FIG. 4 is diagram illustrating flow of RF output signals generated by the control console in an example where the electrode attachments are monopolar and are operating in a parallel bipolar mode.
Figure 5:
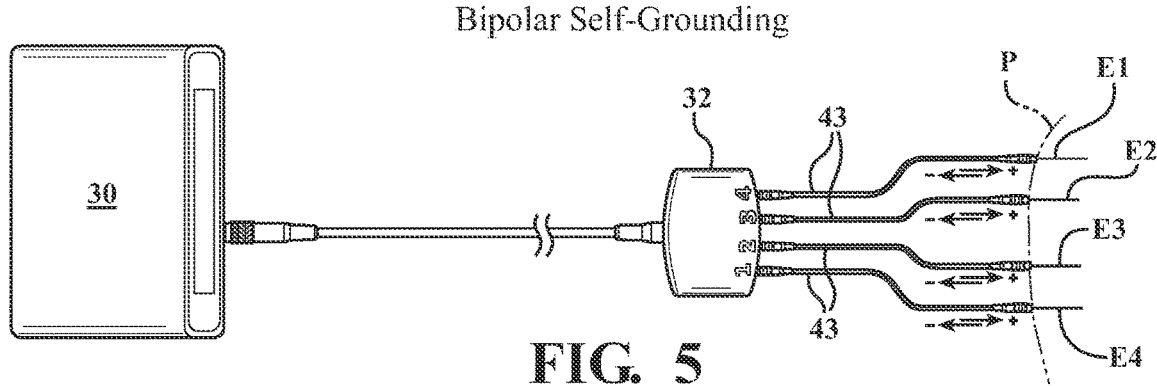
FIG. 5 is diagram illustrating flow of RF output signals generated by the control console in an example where the electrode attachments comprise bipolar self-grounding electrodes.

The various types of electrodes E1-E4, electrode attachments 43 and configurations as well as the RF output signal delivery path for the same will now be described. In general, the control console 30 is configured to operate with at least three different types of electrode attachment 43 configurations, namely monopolar, parallel bipolar, and self-grounding bipolar configurations. These various electrode attachment 43 configurations are illustrated on a high level in FIGS. 3-5. For simplicity, FIGS. 3-5 show connection between the control console 30 and four electrodes E1-E4 applied at respective treatment sites for each configuration. Of course, more or less electrodes E1-E4 may be utilized for any given procedure, as described. Furthermore, the following explanation with respect to FIGS. 3-5 focuses on RF output delivery and omits workflow steps relating to the procedure, such as application of the sensory and motor stimulation signals and injection of anesthetic, which are typically applied before application of the RF output signal. Additionally, control configurations of the control console 30 and cable accessory 32 for accommodating these various electrode attachment 43 configurations are described in later sections.

The monopolar configuration is illustrated in FIG. 3 using four monopolar electrodes E1-E4, the electrode attachment 43 of each being attached separately to the cable accessory 32 which is coupled to the control console 30. For the monopolar configuration, the ground pad 36 is utilized and is placed adjacent the treatment site, e.g., on the skin of the patient P. Each monopolar electrode E1-E4 separately receives the RF output signal from the control console 30 through the cable accessory 32 and through the respective electrode attachment 43. Each electrode E1-E4, upon receipt of the RF output signal, creates a monopolar lesion volume at a distal end tip of each electrode E1-E4 for lesioning the treatment site. For example, frictional heating occurs near an uninsulated tip of the cannula of the corresponding electrode E1-E4 due the RF current alternating at a high frequency. The RF output signal transmits from the distal tip of each electrode E1-E4 to the ground pad 36, and ultimately returning to the control console 30. Thus, for monopolar configurations, each electrode E1-E4 effectively is energized in separately, without dependence on the other electrodes E1-E4 due to the presence of the ground pad 36 providing a common return path for any of the electrodes E1-E4 utilized during the process.

The parallel bipolar configuration is illustrated in FIG. 4 using four monopolar electrodes E1-E4, the electrode attachment 43 of each being attached separately to the cable accessory 32 which is coupled to the control console 30. For the parallel bipolar configuration, two adjacent pairs of monopolar electrodes, e.g., E1, E2, and E3, E4 are utilized in conjunction. The ground pad 36 is not required to be utilized in the parallel bipolar configuration for reasons explained below. However, there may be situations where the ground pad 36 is utilized with the bipolar electrodes, such as where the electrodes are utilized in a monopolar fashion for stimulation, but in a bipolar fashion for nerve ablation. Monopolar electrodes E2 and E4 separately receive the RF output signal from the control console 30 through the cable accessory 32 and through the respective electrode attachment 43. Upon receipt of the RF output signal, electrodes E1 and E2, collaboratively create a bipolar lesion volume shared between distal end tips of electrode E1 and E2 for lesioning the treatment site. Similarly, electrodes E3 and E4 collaboratively create a bipolar lesion volume shared between distal end tips of electrode E3 and E4 upon receipt of the RF output signal. Thus, whereas a monopolar configuration drives the RF output signal between the tip of the electrode E1-E4 and the ground pad 36, the parallel bipolar configuration drives the RF output signal between two nearby electrode tips, e.g., E1, E2, and E3, E4, respectively. The lesion volume may take different shapes depending on the distance between adjacent electrode tips. The RF output signal returns to the control console 30 through electrodes E1 from E2, and through electrode E3 from E4, respectively. Thus, for parallel bipolar configurations, the electrodes E1-E4 are energized in pairs, and operation is dependent on the adjacent electrode E1-E4. Those skilled in the art appreciate that the electrode pairs need not be exactly parallel to one another. Furthermore, although separate monopolar electrodes (and separate monopolar attachment cables 43) have been described in pairs, it is contemplated that a combined parallel bipolar attachment cable 43 and electrode assembly 34 may be utilized.

The bipolar self-grounding configuration is illustrated in FIG. 5 using four bipolar self-grounding electrodes E1-E4, the electrode attachment 43 of each being attached separately to the cable accessory 32 which is coupled to the control console 30. The bipolar self-grounding electrodes E1-E4 comprise a different configuration and operate differently from the described monopolar electrodes E1-E4. Specifically, each bipolar self-grounding electrode E1-E4 separately receives the RF output signal from the control console 30 through the cable accessory 32 and through the respective electrode attachment 43. The ground pad 36 is not required to be utilized in the bipolar self-grounding configuration for reasons explained below. Each bipolar self-grounding electrode E1-E4, upon receipt of the RF output signal, creates a bipolar lesion volume at a distal end tip of each electrode E1-E4 for lesioning the treatment site. However, unlike the monopolar configuration, the RF output signal is returned through the same tip of each electrode E1-E4, and ultimately returning to the control console 30. The bipolar self-grounding configuration is similar to the monopolar configuration in that each electrode E1-E4 effectively is energized in separately, without dependence on the other electrodes E1-E4. However, unlike the monopolar configuration, the return path of the RF output signal for the bipolar self-grounding configuration is optimized by enabling the RF output signal to return to the console 30 directly through each respective electrode E1-E4. This eliminates the need to assemble and place the ground pad 36, and further eliminating prolonged transmission of the RF signal output from the electrode E1-E4 to the ground pad 36 through the patient P. In other words, each electrode E1-E4 is "self-grounded" by enabling the aforementioned return path through a single electrode E1-E4.

Aspects and components of the controller 60 and the amplifier and relay control section 62 are described in FIGS. 6-9 for examples of the monopolar, parallel bipolar, and self-grounding bipolar configurations. It is to be appreciated that the same controller 60 and the amplifier and relay control section 62 configuration is intended for illustration in FIGS. 6-9. However, for simplicity in illustration, components that are not required to be utilized in respective monopolar, parallel bipolar, and self-grounding bipolar configurations have been omitted from illustration. Although omitted, it is intended that these components would still exist to accommodate configurations other than the respective configuration illustrated. Furthermore, although a certain number of components and electrical paths are described and numbered for simplicity, it is to be appreciated that additional components and electrical paths are contemplated for any of the described configurations.

Figure 6:
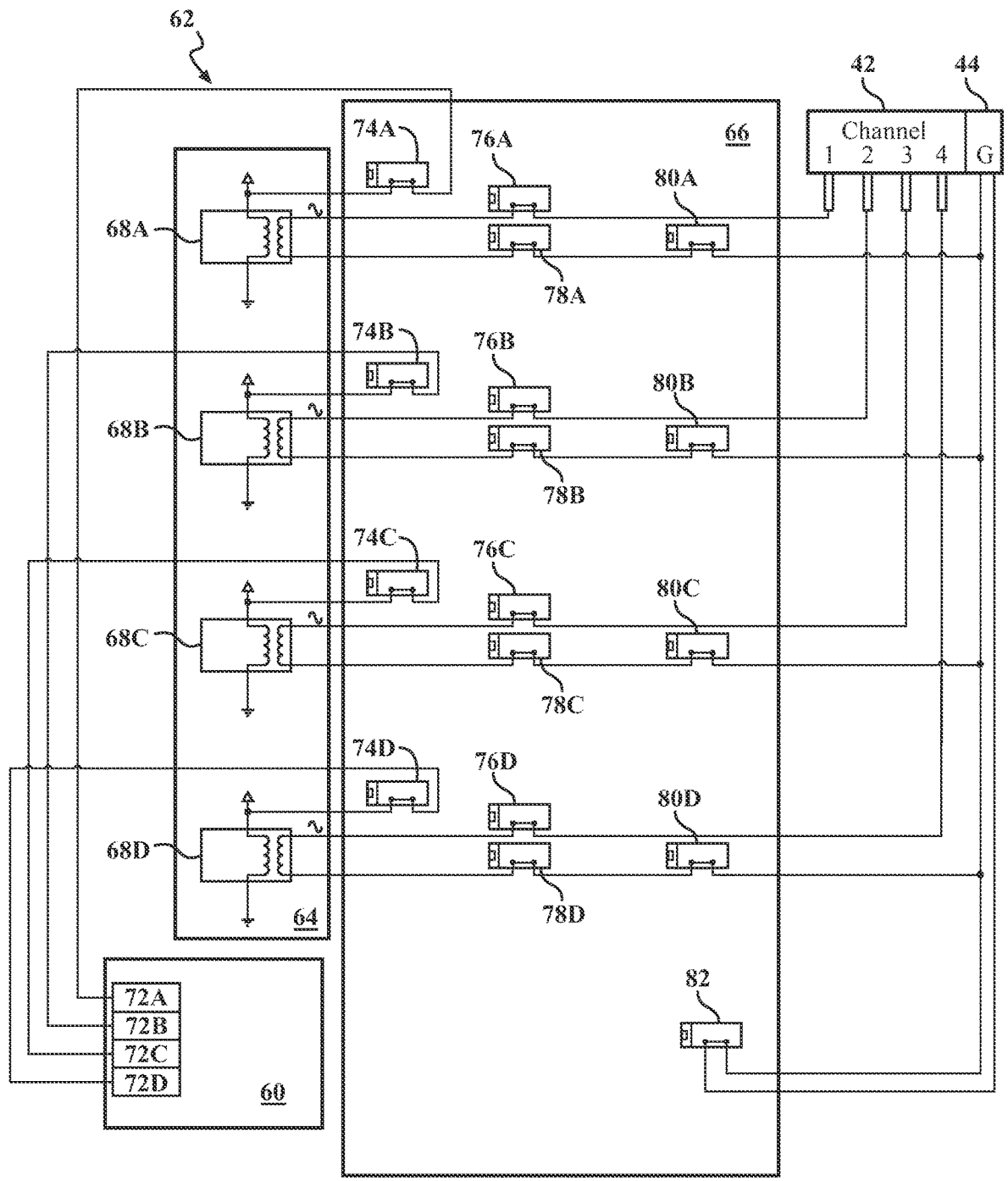
FIG. 6 is a circuit diagram of components of the control console being configured to accommodate monopolar electrode attachments of FIG. 3 operating in the monopolar mode.

As fully shown in FIG. 6, the amplifier section 64 comprises four separate RF amplifiers 68A-68D. Although four separate RF amplifiers 68A-68D are shown, it is to be appreciated that any number of RF amplifiers 68 greater than two may be provided or utilized depending on the configuration. Each RF amplifier 68A-68D provides the RF output signal for a corresponding channel CH1, CH2, CH3, CH4 of the control console 30. Each CH1, CH2, CH3, CH4 is associated with the corresponding RF amplifier 68A-68D and not necessarily with the electrode number E1-E4 connected to the first connection interface 42 of the control console 30. However, there are some configurations, as will be described, where this may be the case.

The controller 60 comprises DC power supplies 72A-72D for the RF amplifiers 68A-68D. In one example, each DC power supply 72A-72D is dedicated for the respective RF amplifier 68A-68D and/or channel CH1, CH2, CH3, CH4. In other examples, the DC power supplies 72A-72D may be combined for any one or more RF amplifiers 68A-68D. Depending on the selection from the GUI 52, the DC voltage provided by each DC power supply 72A-7D may be variable or anywhere from 0-40 volts.

Associated with each RF amplifier 68A-68D is a power supply relay 74A-74D. The power supply relay 74A-74D is coupled between each DC power supply 72A-72D and an input of each respective RF amplifier 68A-68D. Each power supply relay 74A-74D is configured to selectively switch on/off connection of the DC power supply 72A-72D to the respective RF amplifier 68A-68D. For example, such switching may be off when DC power to the respective RF amplifier 68A-68D is not needed and switched on when DC power is needed. The power supply relays 74A-74D are controlled by switching signals provided by the controller 60 and/or the relay section 66. The input of each RF amplifier 68A-68D is connected to ground in order to create a return path for electrical current provided from each DC power supply 72A-72D. The power supply relays 74A-74D may be any suitable type of relays, such as inductive load drivers, reed relays, or the like.

The input of each RF amplifier 68A-68D is configured to separately receive electrical current at from the respective DC power supply 72A-72D and each RF amplifier 68A-68D generates a respective RF output signal at its output. The RF output signal parameters will depend on various factors, such as parameters selected by the user from the GUI 52, such as voltage from the DC power supply 72A-72D, frequency, pulse width of the RF output, and the like.

The controller 60 is configured to monitor one or more treatment parameters. As described above, examples of such treatment parameters include patient-circuit impedance (e.g., impedance of the path from each respective RF amplifier 68A-68D output, through the patient P, and back to each respective RF amplifier 68A-68D) and temperature of the lesion location (e.g., monitored by thermocouples coupled to each electrode E1-E4). In situations where one or more of the electrodes E1-E4 is coupled to the respective channel CH1-CH4, the controller 60 is configured to generate the control signals for controlling each RF amplifier 68A-68D at the input based on the one or more of the monitored treatment parameters.

In one example, the control signals for each RF amplifier 68A-68D comprise two pulse width modulated (PWM) control signals 91, 93 (shown in FIGS. 10-12) applied for each RF amplifier 68A-68D. The PWM control signals 91, 93 are applied to enable each RF amplifier 68A-68D to generate RF output signals RFA and RFB for each channel CH1-CH4. For instance, the monopolar configuration may use one RFA output signal, the parallel bipolar configuration may use two RFA output signals or two RFB output signals (each one from a different channel), and the self-grounding bipolar configuration may use one RFA signal and one RFB signal from one channel (or different channels). In one example, the PWM control signals 91, 93 are out of phase from each other (e.g., by 180 degrees) and are delivered at a high frequency, such as 500 KHz. The two PWM control signals 91, 93 pass through field effect transistors (FET) drivers and logic level shift to larger PWM signals at 12V, while maintaining the frequency. The PWM control signals 91, 93 further pass through respective power FETs and are amplified using a topology known as push-pull and are ultimately converted to a sine wave at the output of each RF amplifier 68A-68D. The sine wave is the source of the RF energy and thereby implements the RF output signal.

In one example, each RF amplifier 68A-68D comprises a transformer having a center (neutral) tap input and two line taps. The amplified version of the PWM control signals 91, 93, from the power FETs are applied respectively to the two line taps of the transformer. The amplitude of the sine wave of the RF output signal depends on a variable voltage adjustment (e.g., 0-40V) provided from each respective DC power supply 72A-72D to the center tap of each transformer input. This variable voltage adjustment provided by each respective DC power supply 72A-72D is also a control signal and is used in conjunction with the PWM control signals 91, 93 to control the input of each RF amplifier 68A-68D, and ultimately the RF output signals. Each transformer output provides a gain to the transformer input voltage. In one example, this gain is non-linear. For example, if one DC power supply 72 provides 20V to the center tap, the output sine wave amplitude may increase by two times that input value, i.e., 40V. The RF amplifiers 68A-68D may have configurations other than those described herein. The RFA and RFB output signals are managed by the relay section 66, which steers the signal delivery to the patient for any of the aforementioned electrode configurations.

Sensors and control algorithms determine how the PWM signals 91, 93 behave and how the voltage adjustments from the DC power supplies 72 are set. For example if the patient's impedance changes for any reason, the impedance data is communicated to the controller 60 and a lookup table, which is stored in memory in the controller 60, is checked for the maximum allowable setting to the center tap of the transformer based on the patient's impedance, and limitations for allowable current. In response, a new input voltage is calculated and provided from the DC power supply 72 to the center tap of the transformer. In turn, the push-pull topology amplification is adjusted to limit the output power to a predetermined limit, e.g., 25 Watts (rms current×rms voltage).

The patient-circuit impedance commonly changes while the lesion is in process. In the one example, the patient-circuit impedance for each channel CH1-CH4 is monitored continuously in order to compensate for real-time changes to patient-circuit impedance for each channel CH1-CH4. This facilitates real-time adjustment to the aforementioned center tap input voltage calculations for the DC power supply 72A-72D of each RF amplifier 68A-68D.

The adjustable DC power supply 72A-72D dedicated to each RF amplifier 68A-68D facilitates improved safety and efficacy. Utilizing the patient-circuit impedance measurements for each treatment location, the DC power supply 72A-72D for each RF amplifier 68A-68D may be adjusted to maximize the safety and effectiveness of treatment for each lesion location. Based upon the patient-circuit impedance for each channel CH1-CH4, an upper voltage limit for the DC power supply 72A-72D for each RF amplifier 68A-68D can be calculated thereby limiting that respective maximum current and maximum power for each channel CH1-CH4 to clinically established safe levels.

Temperature sensor data from the treatment site may also be used to control the amount of time the PWM signals 91, 93 are active during a time slice (e.g., the duty cycle) designated for that channel's amplifier to keep the temperature from exceeding an intended value. If the temperature measured for one of the channels CH1-CH4 is rising faster then what the control loop desires, the PWM signals 91, 93 may be halted completely for a percentage of the time slice (e.g., by reducing the duty cycle). This measure may effectively shut down the amplifier output for the channel. The PWM control signals 91, 93 and the variable voltage control signal from the DC power supply 72 are applied in conjunction, at the input of each RF amplifier 68A-68D. The control loop techniques described herein may be utilized for any of the channels CH1-CH4 and may operate according to other manners not specifically recited herein.

It should be understood that treatment parameters other than patient-circuit impedance and temperature may be utilized with the aforementioned techniques. Additionally, any one of, or the combination of patient-circuit impedance and temperature may be utilized to generate control signals. Furthermore, it is contemplated that the control signals based on treatment parameters may be controlled or defined in manners different from the techniques described.

It is to be appreciated that the RF amplifiers 68A-68D are distinguished from the respective DC power supplies 72A-72D. In other words, each channel CH1, CH2, CH3, CH4 has access to not only the respective DC power supply 72A-72D, but also access to the respective RF amplifier 68A-68D.

An RF amplifier output relay 76A-76D is coupled between an output of each respective RF amplifier 68A-68D and the first connection interface 42 of the control console 30, which connects to the cable accessory 32. Each RF amplifier output relay 76A-76D is configured to selectively switch on/off connection between the output of each RF amplifier 68A-68D and the first connection interface 42. For example, switching on each RF amplifier output relay 76A-76D may be performed when the respective channel CH1, CH2, CH3, CH4 is utilized by the control console 30 during the lesion mode, but not in the sensory or motor stimulation modes. The RF amplifier output relays 76A-76D are controlled by switching signals provided by the controller 60 and/or the relay section 66. The RF amplifier output relays 76A-76D may be any suitable type of relays, such as inductive load drivers, reed relays, or the like.

An RF amplifier return relay 78A-78D is coupled between the output of each respective RF amplifier 68A-68D and the second connection interface 44 of the control console 30, which connects to the connector 46 for the ground pad 36. Each RF amplifier return relay 78A-78D is configured to selectively switch on/off connection between the second connection interface 42 and each respective RF amplifier 68A-68D. Just as with the RF amplifier output relays 76A-76D, switching on each RF amplifier return relay 78A-78D may be performed when the respective channel CH1, CH2, CH3, CH4 is utilized by the control console 30 during the lesion mode, but not in the sensory or motor stimulation modes. The RF amplifier return relays 78A-78D are controlled by switching signals provided by the controller 60 and/or the relay section 66. The RF amplifier return relays 78A-78D may be any suitable type of relays, such as inductive load drivers, reed relays, or the like.

Referring to FIG. 6, operation of the amplifier and relay control section 62 is described for the monopolar configuration having four monopolar electrode attachments 43, as shown in the example of FIG. 3. The monopolar electrode attachments 43 are coupled to the first connection interface 42 and the ground pad 36 is coupled to the second connection interface 44. Each channel CH1-CH4 comprises a ground pad relay 80A-80D connected between the second connection interface 44 and each respective RF amplifier return relay 78A-78D. The ground pad relays 80A-80D are activated only for certain configurations requiring a return path from the ground pad 36, such as monopolar configurations. Each ground pad relay 80A-80D is controlled by switching signals provided by the controller 60 and/or the relay section 66 and may be any suitable type. With each ground pad relay 80A-80D closed, a closed circuit is formed for the monopolar configuration as shown in reference to FIG. 3. For example, with reference to one of the channels for simplicity, i.e., CH1 in FIG. 6, the RF output signal is outputted from the RF amplifier 68A, through the RF amplifier output relay 76A, and through the CH1 output on the first connection interface 42, thereby exiting the control console 30. After the RF output signal is passed through the monopolar electrode attachment 43 coupled to CH1, the RF output signal passes through the patient and returns through the ground pad 36. From here, the RF output signal returns through the second connection interface 44 at the control console 30, through the ground pad relay 80A, through the RF amplifier return relay 78A, and eventually back to the RF amplifier 68A for CH1. This process is conducted similarly for each respective channel CH1, CH2, CH3, CH4 having electrode attachments 43 connected thereto for operating in the monopolar configuration.

The relay section 66 may further utilize a ground pad testing relay 82 as part of a neutral electrode monitoring circuit. The ground pad testing relay 82 is coupled between the ground pad 36, i.e., through the second connection interface 44, and the return for each RF amplifier 68A-68D, and provides a redundant connection to the ground pad 36. The ground pad testing relay 82 may comprise any suitable relay, such as a two-circuit relay. The neutral electrode monitoring circuit monitors failures of the ground pad 35 or connections thereto in compliance with International Electrotechnical Commission (IEC) standard 60601-1.

Figure 7:
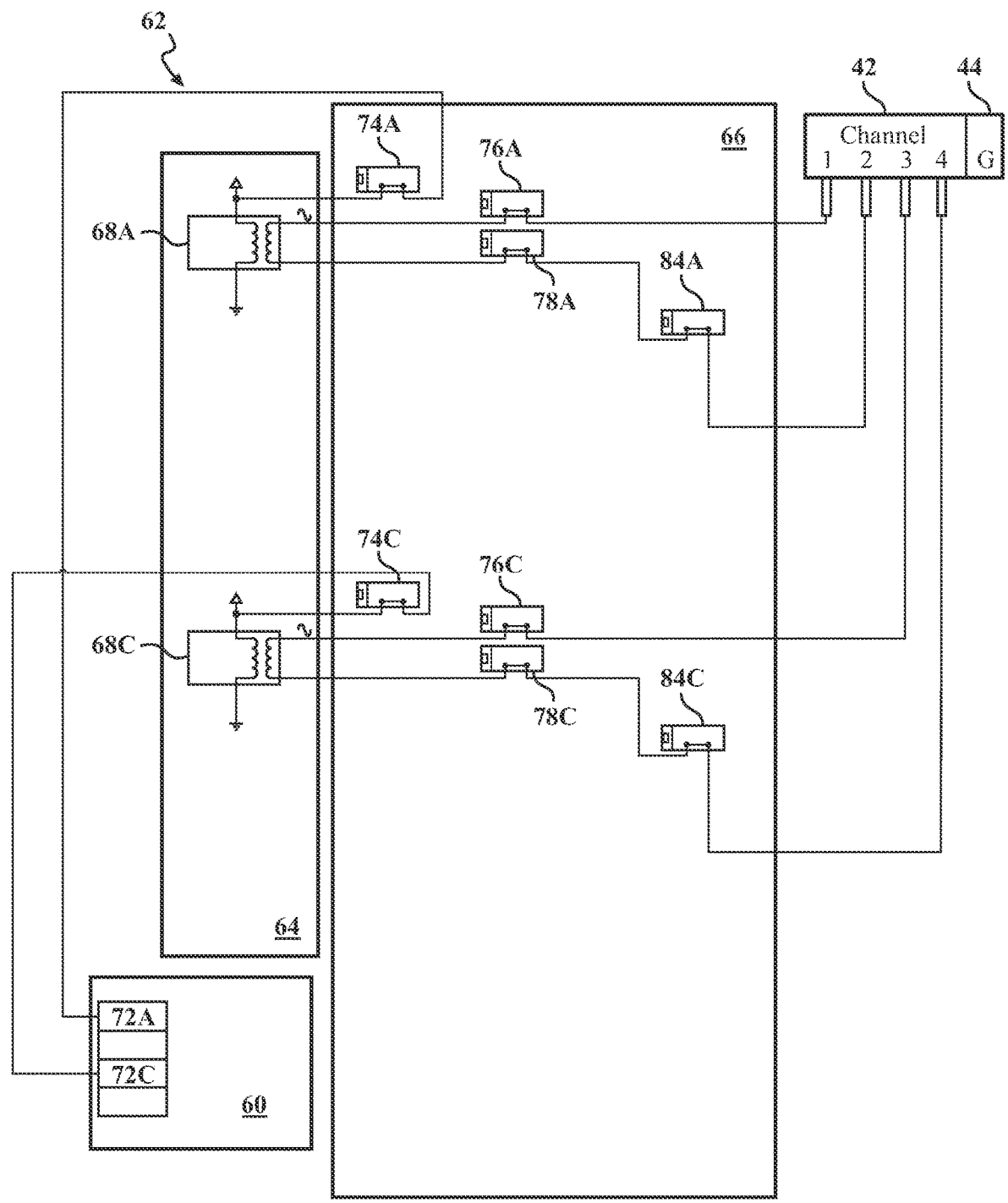
FIG. 7 is a circuit diagram of components of the control console being configured to accommodate monopolar electrode attachments of FIG. 4 operating in the parallel bipolar mode.

Referring to FIG. 7, operation of the amplifier and relay control section 62 is described for the parallel bipolar configuration using four monopolar electrode attachments 43 (i.e., electrodes E1-E4), as shown in the example of FIG. 4. In this example, the four monopolar electrode attachments 43 are coupled to the first connection interface 42, but each pair of monopolar electrodes is operating in a parallel bipolar configuration. In this configuration, a pair of adjacent monopolar electrodes are utilized in conjunction across a first pair of channels CH1/CH2 and a second pair of channels CH3/CH4 to create two bipolar lesions. As will be described below, the control console 30 may detect that each electrode attachment 43 is monopolar, and therefore, able to function in the parallel bipolar configuration. Selection between the monopolar and parallel bipolar configuration for such monopolar electrodes maybe selected using the GUI 52. The ground pad 36 is not required to be utilized in the parallel bipolar configuration, and therefore, the ground pad relays 80A-80D are opened, thereby disconnecting the second connection interface 44 and each respective RF amplifier return relay 78A-78D. For the parallel bipolar configuration, the relay section 66 instead utilizes and activates parallel bipolar relays 84A-84D (only 84A and 84C shown in FIG. 7). Each parallel bipolar relay 84A-84D is connected between the return of the RF amplifier 68A-68D of one channel and crosses-over to the first connection interface 42 connection of an adjacent channel. For example, in FIG. 7, although RF amplifier 68A outputs the RF output signal through CH1, the parallel bipolar relay 84A is closed to connect the return of same the RF amplifier 68A to CH2 at the first connection interface 42. Therefore, the electrical path is closed between the electrodes connected to CH1 and CH2, thereby enabling parallel bipolar energization. In FIG. 7, CH3 and CH4 are utilized to create a second parallel bipolar pair with electrodes coupled to these respective channels. For CH3 and CH4, the parallel bipolar relay 84C operates similar to parallel bipolar relay 84A with respect to CH1 and CH2. As such, in the configuration of FIG. 7, only two DC power supplies 72A, 72B and two RF amplifiers 68A, 68B are utilized in conjunction with four channels CH1, CH2, CH3, CH4 and with four monopolar electrodes.

Figure 8:
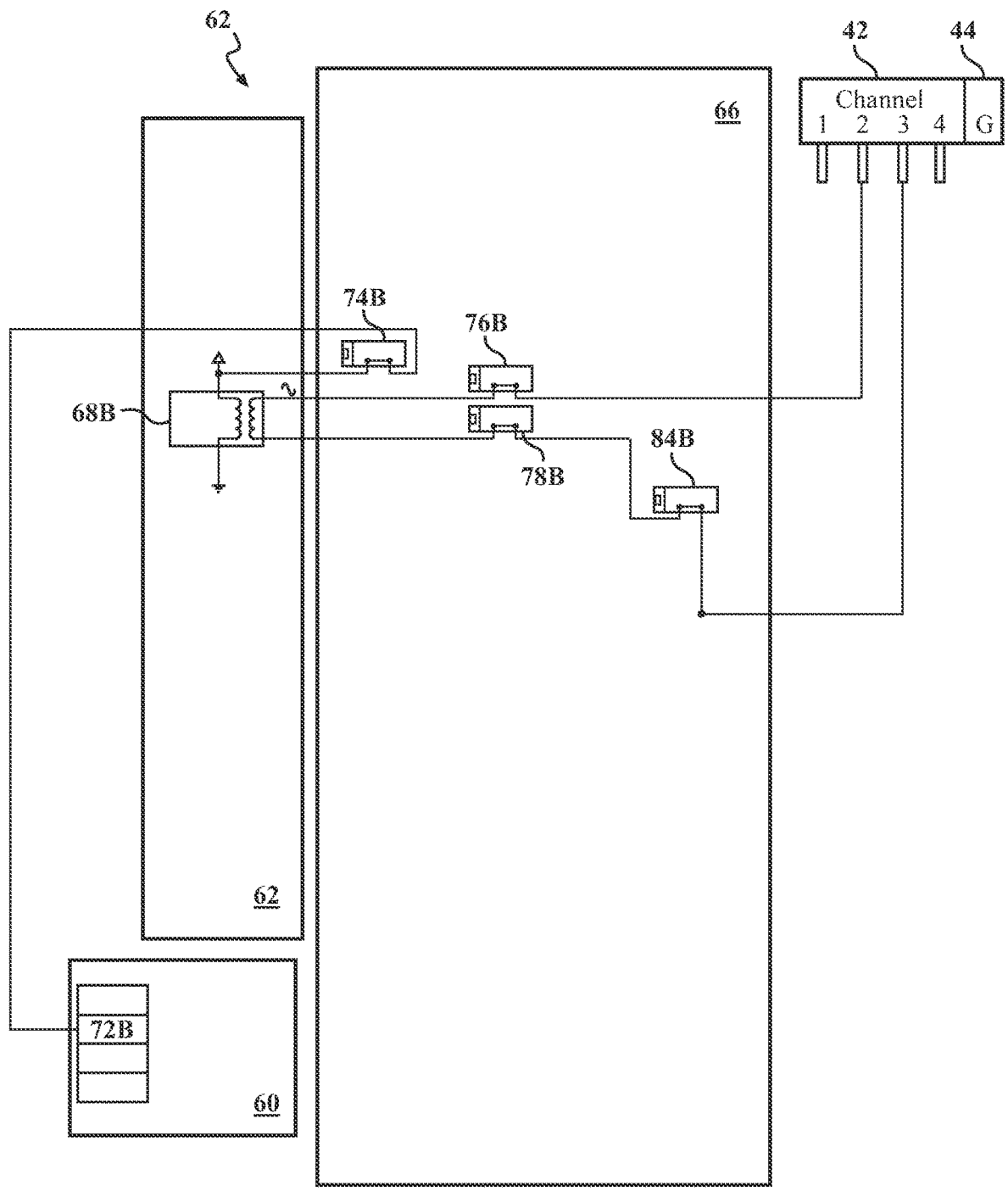
FIG. 8 is a circuit diagram of components of the control console being configured to accommodate monopolar electrode attachments operating in the parallel bipolar mode interleaved between interior channels (CH2/CH3) of the control console.

Referring to FIG. 8, operation of the amplifier and relay control section 62 is described for the parallel bipolar configuration, wherein two electrode monopolar attachments 43 (i.e., E2 and E3) are utilized. Unlike the parallel bipolar example of FIG. 7, which utilizes channels CH1/CH2 or CH3/CH4 for respective pairs, in the example of FIG. 8, the electrode attachments are coupled to channels CH2 and CH3. Thus, the control console 30 and amplifier and relay control section 62 dynamically provides the ability to use other channel pairs besides strictly CH1/CH2 or CH3/CH4 for parallel bipolar. In this configuration, a pair of adjacent monopolar electrodes are utilized in conjunction across a pair of channels CH2/CH3 to create a bipolar lesion. Similar to FIG. 7, parallel bipolar relay 84B is activated (instead of relays 84A and 84C). This enables cross-over to CH3 for return of the RF output signal, thereby enabling parallel bipolar energization with the electrode attachments coupled to CH2 and CH3. It is to be appreciated that the parallel bipolar relays 84A-84D may enable cross-over between other combinations of channels for parallel bipolar configurations, e.g., CH1/CH3, CH2/CH4, CH1/CH4, and these channels may or may not be adjacent to one another. This advantageously provides the control console 30 with the ability to dynamically accommodate various parallel bipolar connections thereby providing added convenience to the user.

Figure 9:
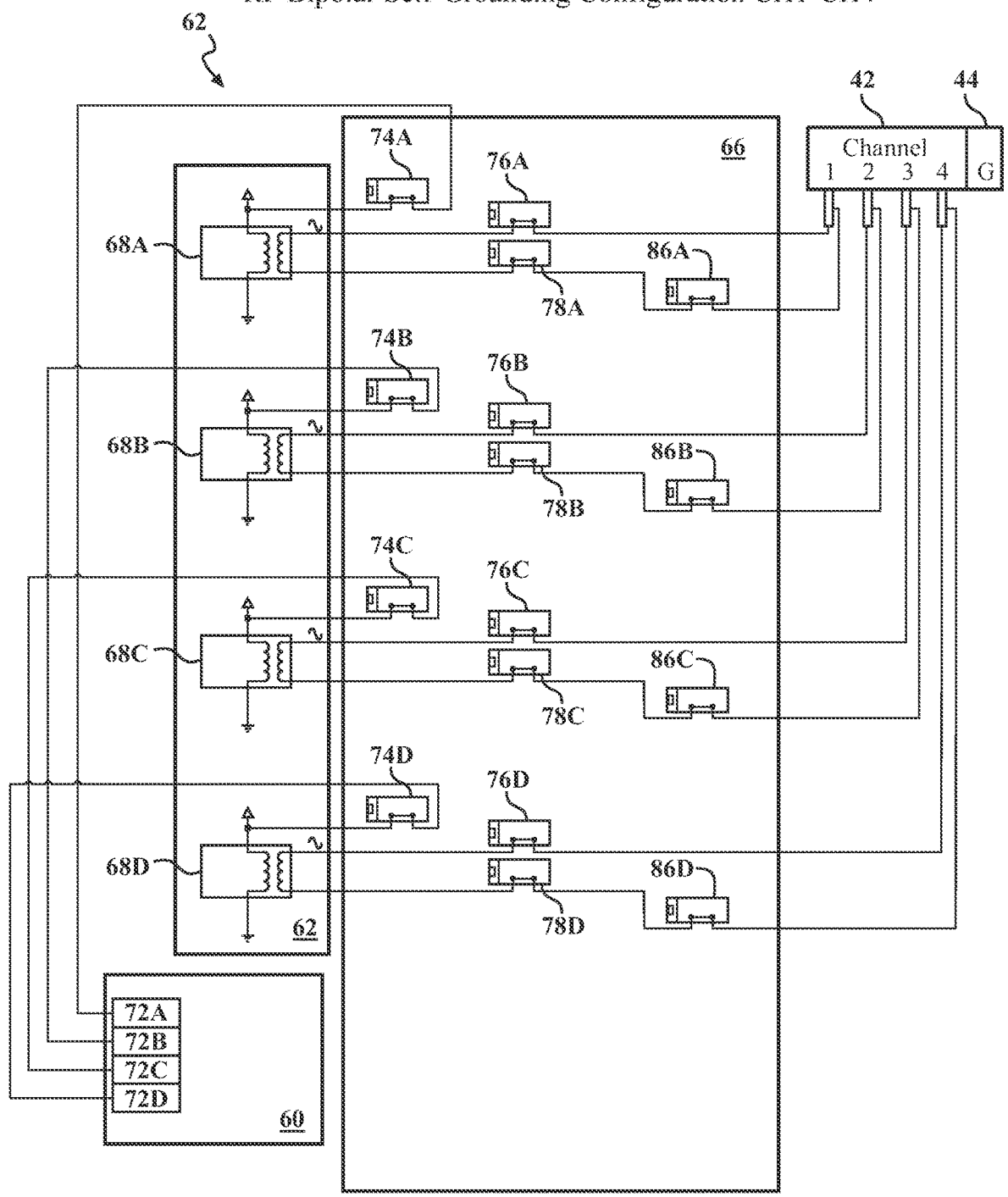
FIG. 9 is a circuit diagram of components of the control console being configured to accommodate bipolar self-grounding electrode attachments of FIG. 5.

Referring to FIG. 9, operation of the amplifier and relay control section 62 is described for the bipolar self-grounding configuration having four separate self-grounding electrode attachments 43, as shown in the example of FIG. 5. The bipolar self-grounding electrode attachments 43 are coupled to the first connection interface 42. The ground pad 36 is not required to be utilized and is therefore not coupled to the second connection interface 44. Each channel CH1-CH4 comprises a self-grounding relay 86A-86D connected between the first connection interface 42 and each respective RF amplifier return relay 78A-78D. More specifically, the self-grounding relay 86A-86D for each channel CH1-CH4 connects to a terminal at the first interface connection 42 for the same respective channel CH1-CH4 for which the self-grounding relay 86A-86D belongs. The self-grounding relays 86A-86D are activated only for certain configurations requiring a return path to the same channel from which the RF signal output was provided. Each self-grounding relay 86A-86D is controlled by switching signals provided by the controller 60 and/or the relay section 66 and may be any suitable type. With each self-grounding relay 86A-86D closed, a closed circuit is formed for the self-grounding bipolar configuration as shown in reference to FIG. 5. For example, with reference to one of the channels for simplicity, i.e., CH1 in FIG. 9, the RF output signal is outputted from the RF amplifier 68A, through the RF amplifier output relay 76A, and through the CH1 output on the first connection interface 42, thereby exiting the control console 30. After the RF output signal is passed to the self-grounding electrode attachment 43 coupled to CH1, the RF output signal, after interacting with the treatment site, passes back through the tip of the same self-grounding electrode attachment 43 and returns through the first interface connection 42 (not the second interface connection 44 for the ground pad 36). From here, the RF output signal returns through the self-grounding relay 86A, through the RF amplifier return relay 78A, and eventually back to the RF amplifier 68A for CH1. This process is conducted similarly for each respective channel CH1, CH2, CH3, CH4 having electrode attachments 43 connected thereto for operating in the self-grounding configuration.

Those skilled in the art appreciate that FIGS. 6-9 are intended to provide certain examples of the monopolar, parallel bipolar, or self-grounding bipolar configurations. Of course, depending on the types of electrode configurations utilized, whether simultaneously or separately, additional or alternative relays other than those described herein and shown in the figures may be utilized to implement each of the monopolar, parallel bipolar, or self-grounding bipolar configurations. In other words, not every combination of the monopolar, parallel bipolar, and self-grounding bipolar configurations are shown throughout the figures or described herein for simplicity and the configuration of the relays may be understood from the combined teachings of FIGS. 6-9.

For the examples described, it is to be appreciated that the RF output signal, although described in singular form, may be indeed a plurality of RF output signals from each respective RF amplifier 68A-68D. Furthermore, these one or more RF output signals for each respective RF amplifier 68A-68D may be similar, i.e., repeated, or may be different from one another. Additionally, the RF amplifiers 68A-68D may produce RF output signals that are the same as or different from one another. In addition, for simplicity in description, the RF output signal has been described as returning to each respective RF amplifier 68A-68D. However, it is to be understood that characteristics of each respective RF output signal may be modified in response to application of the RF output signal to the patient P treatment site. Thus, the returning RF output signal may be different from the original RF output signal.

With the overview of the electrosurgical system 20 being described, specific features, methods, and techniques of the electrosurgical system 20 will now be detailed.

II. Multiple Amplifier Time Slicing Techniques

As shown in FIGS. 6-9, the control console 30 provides multiple RF amplifiers 68A-68D. The multiple RF amplifiers 68A-68D each comprise independent output level control provided by the DC power supplies 72A-72D. Fully independent control of each channel CH1-CH4 is made possible by this configuration. Each RF amplifier 68A-68D is powered by its own dedicated and adjustable DC power supply 72A-72D. The dedicated adjustable power supply enables each channel CH1-CH4 to have its RF Amplifier 68A-68B voltage level to be optimized as a function of the clinical condition present at its individual treatment region.

This multiple RF amplifier 68A-68D configuration represents an improvement over a single amplifier simultaneously applied to multiple channels. Furthermore, utilizing variable control signals being implemented by, e.g., the PWM signals 91, 93 and the variable voltage signal from each DC power supply 72A-72D to each RF amplifier 68A-68D, enables a technique to provide non-simultaneous energy delivery time-slicing for the multiple RF amplifiers 68A-68D. This technique offers a significant advantage over a single amplifier with RF output relays that must be repeatedly switched in order achieve non-simultaneous time-slice output to multiple channels. Furthermore, single amplifier configurations do not provide significant time to adjust power supplies to the single amplifier and singe amplifier configurations are not equipped to handle the switching speed required for self-grounding bipolar electrode attachments 43, as described herein.

In one example, the RF output relays 76, 78, 80, 84, 86 (FIGS. 6-9) may be configured prior to the initiation of active RF output. These relays 76, 78, 80, 84, 86 on the output side of the RF amplifiers 68A-68D are typically prone to relatively slow response times. Ideally, it is preferred that these relays 76, 78, 80, 84, 86 are not reconfigured over the course of the RF treatment. However, there may be situations where the relays 76, 78, 80, 84, 86 are configured during the course of treatment, such as to avoid unwanted return paths through certain channels CH1-CH4. These relays 76, 78, 80, 84, 86 may be controllable free of restriction from activation of the corresponding RF amplifier 68A-68D. Switching of the control signals at the input side of the RF amplifiers 68A-68D may be accomplished using signal level control devices implemented by the controller 60, such as FETs, thereby providing near instantaneous switching without requiring the use of relays 76, 78, 80, 84, 86 for switching. Such switching may be accomplished using techniques such PWM to drive the FETs which steer control signals to the RF amplifiers 68A-68D. The controller 60 can switch and adjust the DC supply voltages and times for the DC power supplies 72A-72D on the fly between the multiple RF amplifiers 68A-68D at much higher rates than previously possible. For example, instead of utilizing 125 millisecond time slots for each the four channels CH1-CH4 leading to each channel CH1-CH4 cycling RF on for 125 milliseconds and then off for 375 milliseconds, much shorter time slots and much higher switching rates are feasible.

Motor nerve sensitivity to electrical activity is greatest at approximately 2 Hz and decreases as the stimulus frequency gets more distant from 2 Hz in the frequency domain. Sensory nerve sensitivity to electrical activity is greatest at approximately 50 Hz and decreases as the stimulus frequency gets more distant from 50 Hz in the frequency domain. Switching of the input control signals between RF amplifiers 68A-68D at significantly higher rates are easily realizable using the techniques described herein. By switching between channels CH1-CH4 at rates above 2 Hz, the techniques described herein diminish the likelihood of unwanted inadvertent neuromuscular stimulation occurring as a result of the nerve lesioning process. By switching between channels CH1-CH4 at rates well above 50 Hz, the techniques described herein diminish the likelihood of unwanted stimulation of patient motor or sensory nerves.

A further advantage of this method is that the relatively long off-time cycling off-time of each channel CH1-CH4 (e.g., 375 milliseconds) is reduced thereby mitigating the occasional challenge in getting difficult to heat-up lesion locations up to treatment temperature in a timely manner that cost effective patient treatment demands.

Accordingly, in one example, the control console 30, being configured with a plurality of the RF amplifiers 68A-68D each being dedicated to deliver energy (e.g., RF output signals) to a corresponding one of the channels CH1-CH4, enables the controller 60 to generate control signals to separately and independently control the input of each of the RF amplifiers 68A-68D and to sequentially apply the control signals to each RF amplifier 68A-68D, one at a time, to enable the RF amplifiers 68A-68D to generate the RF output signals for delivering energy to the corresponding channel CH1-CH4.

Figure 10:
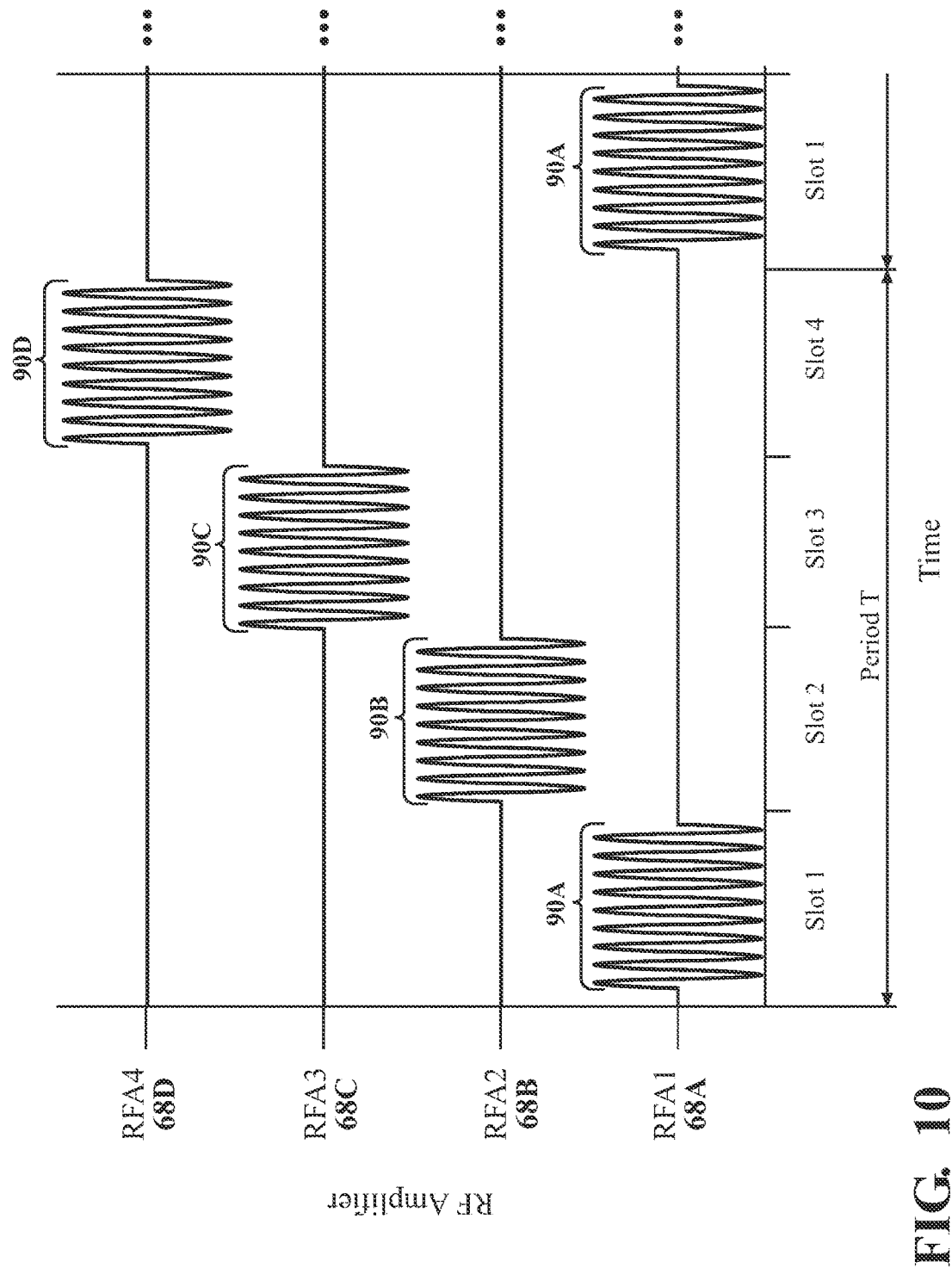
FIG. 10 is a chart illustrating application of input control signals to multiple RF amplifiers in the control console in relation to FIG. 6 wherein monopolar electrode attachments are operating in the monopolar mode.

Referring to FIG. 10, application of respective the PWM control signals, 91A-91D and 93A-93D, to the input of each of the RF amplifier 68A-68D is illustrated. The controller 60 is configured to sequentially apply the control signals 91, 93 to each RF amplifier 68A-68D during sequential time slots each being reserved for a different one of the RF amplifiers 68A-68D. In FIG. 10, a diagram illustrating this sequential application of control signals 91, 93 is provided for one example, and more specifically for the four-monopolar electrode configuration example shown in FIG. 3. Although energization of electrodes E1-E4 from the RF output signals provided from the RF amplifiers 68A-68D is expected, FIG. 10 does not illustrate application of these RF output signal at each electrode attachment 43. Instead, the diagram of FIG. 10 relates to the application of control signals 91, 93 to the input of the RF amplifiers 68A-68D in order to generate the respective RF output signals.

As shown in FIG. 10, the time slots are identified as slots 1-4. Time slot 1 is reserved for RF amplifier 68A, time slot 2 is reserved for RF amplifier 68B, time slot 3 is reserved for RF amplifier 68C, and time slot 4 is reserved for RF amplifier 68D. Control signals 91A, 93A separately and independently control RF amplifier 68A during time slot 1, control signals 91B, 93B separately and independently control RF amplifier 68B during time slot 2, control signals 91C, 93C separately and independently control RF amplifier 68C during time slot 3, and control signals 91D, 93D separately and independently control RF amplifier 68D during time slot 4. In this example, the time slots 1-4 are divided equally among the RF amplifiers 68A-68D.

As shown, these respective control signals 91, 93 are applied sequentially and one at a time for each RF amplifier 68A-68D. The controller 60 stops application of the control signals 91, 93 for any given RF amplifier 68A-68D during time slots reserved for other RF amplifiers. For example, the controller 60 stops application of the control signals 91A, 93A to RF amplifier 68A during time slots 2-4, which are reserved for RF amplifiers 68B-68D. Thus, the RF amplifiers 68A-68D are controlled non-simultaneously. In turn, energy delivery among the channels CH1-CH4 is non-simultaneous.

A period T is defined by a sum of the time slots 1-4. In other words, the time slots 1-4, when combined, define the period T. The period T may be represented in milliseconds or seconds. As shown in FIG. 10, this sequence may be repeated as necessary during treatment. Once the sequence resets, a new period T is initiated.

Although four time slots are utilized in this example for the four different RF amplifiers 68A-68D, it should be understood that any suitable number of time slots may be utilized and that the number of time slots need not be identical to the number of RF amplifiers 68A-68D. For instance, the time slots may each be divided in two, thereby doubling the number of time slots for each RF amplifier 68A-68D during the period T. Furthermore, the time slots need not be divided equally among the RF amplifiers 68A-68D. For instance, RF amplifiers 68A and 68B may each be allocated time slots that comprise one-sixth of the period T, while RF amplifiers 68C and 68D may each be allocated time slots that comprise one-third of the period T. Furthermore, the respective control signals 91, 93 may be applied once or many times for any given time slot for any given RF amplifier 68A-68D. To maximize efficiency, the respective control signals 91, 93 may occupy the entirety of each respective time slot. However, in some instances, the respective control signals 91, 93 alternatively may occupy less than the entirety of each respective time slot for any given RF amplifier 68A-68D. Thus, the control signals 91, 93 may have an adjustable duty cycle.

Furthermore, the diagram of FIG. 10 may be different depending upon the various factors. For example, the control signals 91, 93 shown in FIG. 10 are nearly identical for each RF amplifier 68A-68D. However, some or all of the control signals 91, 93 alternatively may be different from one another, e.g., voltage, amplitude, frequency, phase, duration, etc. Additionally, the sequence shown in FIG. 10 is ordered based on the RF amplifier 68A-68D number. Alternatively, the sequence of control signal 91, 93 application may be ordered differently, e.g., 68D, 68A, 68C, 68B, such that adjacent RF amplifiers 68A-68D need not be controlled in order. Furthermore, control signals provided from the DC power supply 72 may be sequentially time-sliced as shown similarly to the time slicing of the PWM signals 91, 93 in FIGS. 10-12.

Figure 11:
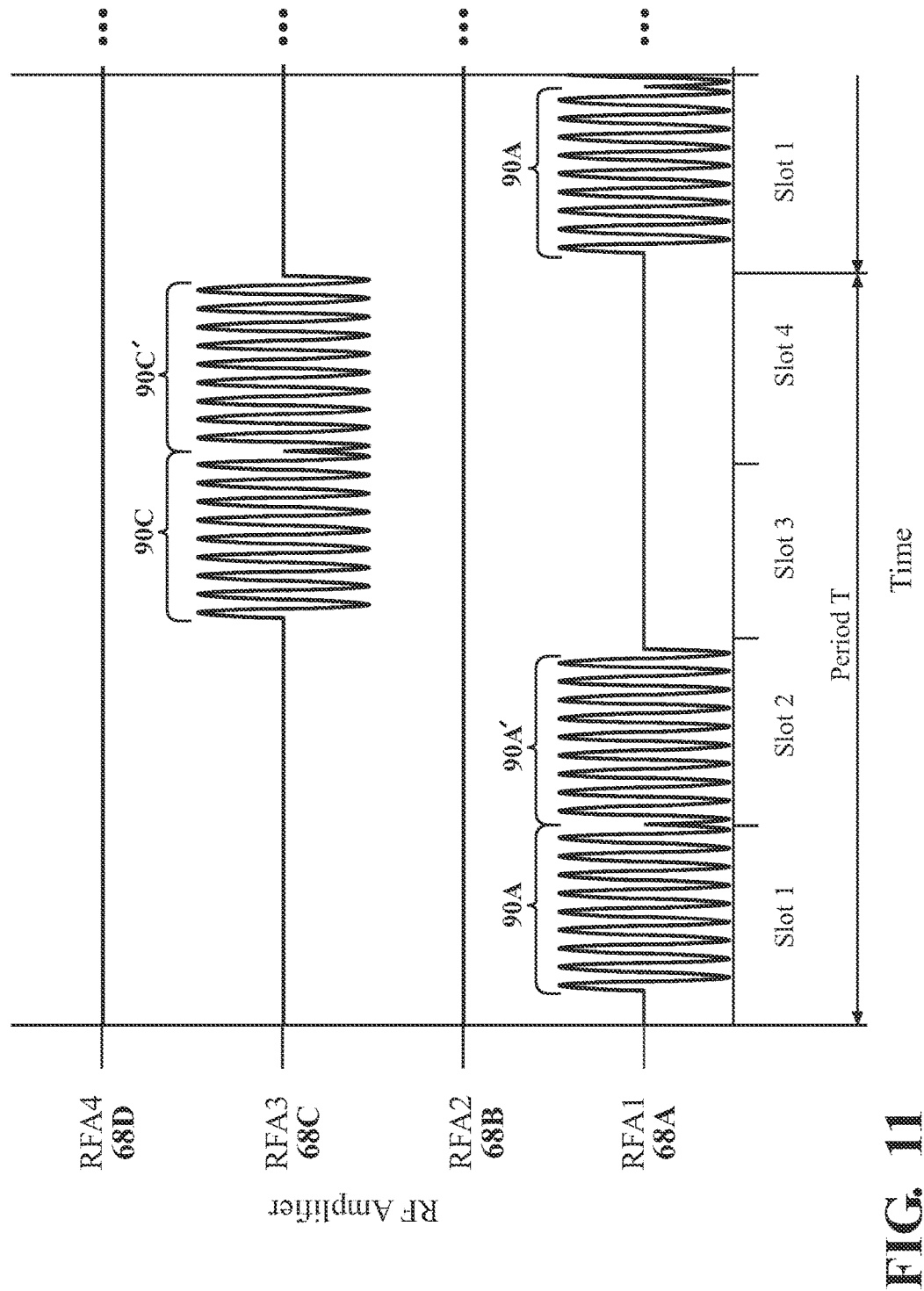
FIG. 11 is a chart illustrating application of input control signals to multiple RF amplifiers in the control console in relation to FIG. 7 wherein monopolar electrode attachments are operating in the parallel bipolar mode.

Moreover, the control signals 91-93 diagram will be different for the parallel bipolar configuration. For instance, FIG. 11 illustrates one example with reference to the parallel bipolar configuration of FIG. 4, time slots 1 and 2 are reserved for RF amplifier 68A and time slots 3 and 4 are reserved for RF amplifier 68C. Control signals 91A, 93A separately and independently control RF amplifier 68A during time slot 1 to generate the RF output signal for parallel bipolar energization. Control signals 91A, 93A further control RF amplifier 68A during time slot 2, wherein the RF output signal is returned to the RF amplifier 68A. Return of the RF output signal from the parallel bipolar pair is accomplished by switching of the relays in on the relay section 66 to establish the proper return path. Similarly, control signals 91C, 93C separately and independently control RF amplifier 68C during time slots 3 and 4 to enable the RF amplifier 68C to generate the RF output signal for energization of the second parallel bipolar pair. The RF output signal is returned to RF amplifier 68C in a similar manner. In this example, the time slots 1-4 are divided equally among the RF amplifiers 68A, 68C. Other arrangements for control signal 91, 93 application for the parallel bipolar configuration are possible in accordance with the variations described above.

Figure 12:
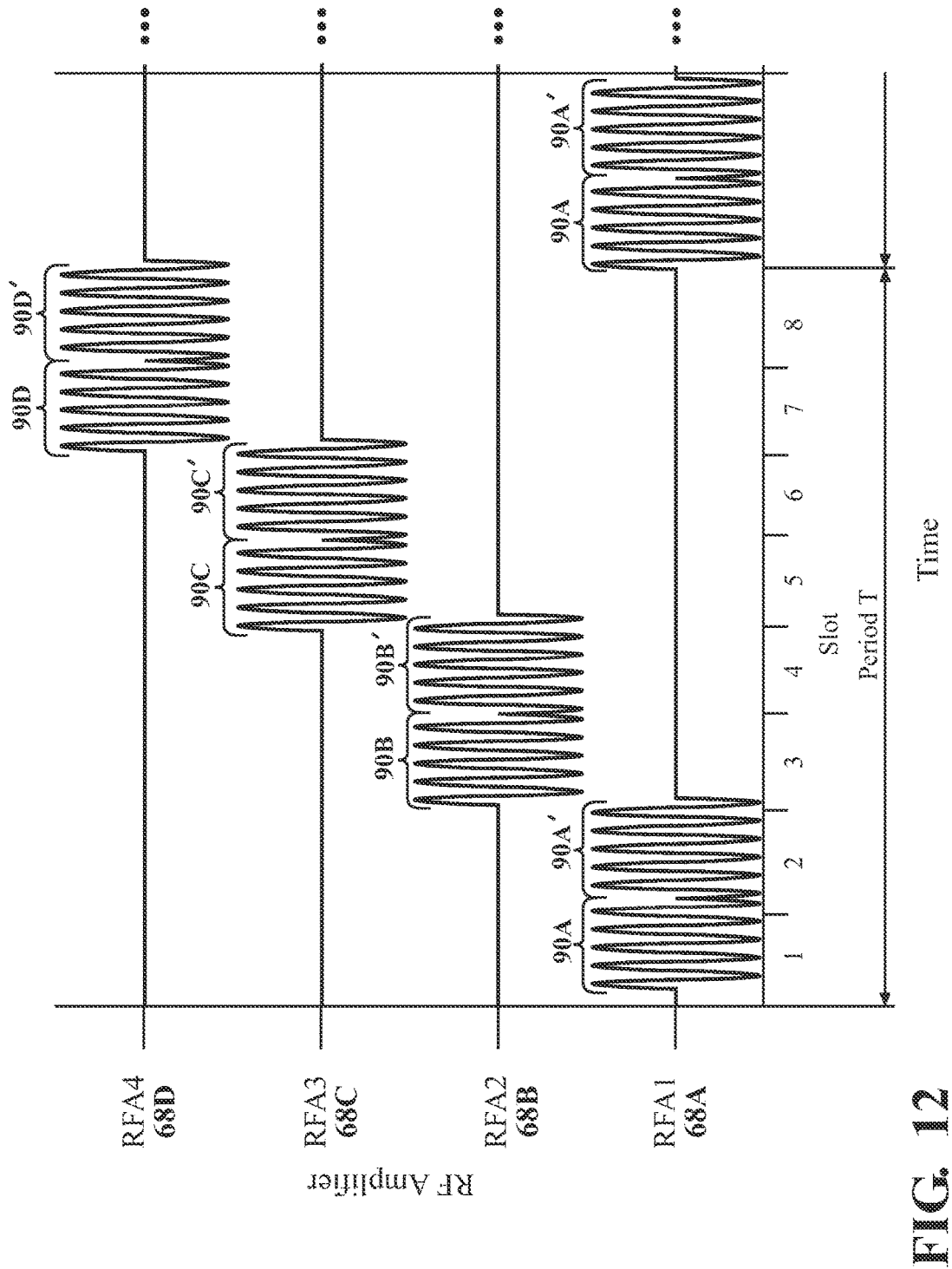
FIG. 12 is a chart illustrating application of input control signals to multiple RF amplifiers in the control console in relation to FIG. 9 for operation of bipolar self-grounding electrode attachments.

FIG. 12 provides a control signal 91, 93 diagram for the self-grounding bipolar configuration of FIG. 5. Here, the time slots are doubled to accommodate fast switching for the self-grounding configuration. Time slots 1 and 2 are reserved for RF amplifier 68A, time slots 3 and 4 are reserved for RF amplifier 68B, time slots 5 and 6 are reserved for RF amplifier 68C, and time slots 7 and 8 are reserved for RF amplifier 68D. Control signals 91A, 93A separately and independently control RF amplifier 68A during time slots 1 and 2 to enable RF amplifier 68A to generate the RF output signal for self-grounding bipolar energization. The RF output signal is sent to the self-grounding bipolar electrode during time slot 1 and returned from the self-grounding bipolar electrode during time slot 2. Return of the RF output signal from the self-grounding bipolar electrode is accomplished by switching of the relays in on the relay section 66 to establish the proper return path. The control signals 91A, 93A are continuously applied during these two slots. This process is repeated for the remaining RF amplifiers 68B-68D. In this example, the time slots 1-8 are divided equally among the RF amplifiers 68A-68D. Other arrangements for control signal 91, 93 application for the self-grounding bipolar configuration are possible in accordance with the variations described above. Furthermore, it is to be appreciated that the control signals may be different from the control signals as shown in FIGS. 10-12 and may also be different from one another for any given one of the RF amplifier 68A-68D, and may be different among the various RF amplifiers 68A-68D.

In accordance with the switching techniques described herein, each channel CH1-CH4 has an output that cycles at a frequency of F Hertz, where F equals 1/T, wherein T is the described period. The frequency F is greater than a motor stimulus sensitivity of 2 Hertz and/or greater than a sensory stimulation sensitivity of 50 Hertz. However, where anesthesia is applied to the target site, the need to provide frequencies greater than motor or sensor stimulation sensitivity may be obviated. In one specific example, the frequency F is within a range defined from 12.5 Hertz to 2,500 Hertz and the period T is within a range defined from 0.0004 seconds to 0.08 seconds. For example, time slots of 100 microseconds for four channels CH1-CH4 results in the period T being 400 microseconds and the channel cycling frequency F being 2,500 Hertz. Time slots of 0.02 seconds for four channels CH1-CH4 results in the period T being 0.08 seconds and the channel cycling frequency F being 12.5 Hertz. The frequency of 12.5 Hz is above motor stimulus sensitivity of 2 Hertz and the frequency of 2,500 Hertz is above the sensory stimulation stimulus sensitivity of 50 Hz. Therefore, the likelihood of undesirable inadvertent neuromuscular motor and sensory stimulation of the patient is avoided. It is to be appreciated that the frequency F may be below or beyond the described range while still avoiding inadvertent neuromuscular motor and sensory stimulation. Furthermore, the calculations described are based on four channels CH1-CH4. Of course, with more or less channels, the calculations may vary from those described. The frequency F and period T may be other values depending on the configuration utilized.

III. Cable Accessory Examples

The cable accessory 32 has been introduced in sections above and examples of this cable accessory 32 are described herein in greater detail. The cable accessory 32 is utilized to interconnect one or more electrode attachments 43 and the control console 30. The control console 30 is configured to energize one or more of the electrode attachments 43 through one or more channels CH1-CH4 to perform RF nerve ablation.

Again, these electrode attachments 43 may comprise monopolar electrodes, monopolar electrodes utilized in the parallel bipolar configuration, or self-grounding bipolar electrodes. There are various combinations of these electrode attachments 43 that may be connected to the control console 30. Examples of these combinations include, for example, up to 4 monopolar electrodes, 2 parallel bipolar electrode pairs, 4 bipolar self-grounding electrodes, 2 monopolar electrodes and 1 parallel bipolar electrode pair, 2 monopolar electrodes and 2 bipolar self-grounding electrodes, 1 parallel bipolar electrode pair and 2 bipolar self-grounding electrodes.

Connection of these electrode attachments 43 may be to, or between, various combinations of the channels CH1-CH4. The cable accessory 32 alleviates burdensome connection and disconnection of electrode attachments 43 between channels CH1-CH4 each time the combination of electrode attachments 43 is changed, e.g., between uses. For example, as shown in FIG. 7, parallel bipolar is possible between CH1/CH2, or CH3/CH4 and also between CH2/CH3, as shown in FIG. 8. Parallel bipolar configuration may also be interleaved between CH1/CH3 and CH2/CH4. The various types of electrode attachments 43 and channel CH1-CH4 connection configurations are all supported by the same cable accessory 32. The cable accessory 32 and system architecture of the control console 30 enables enhanced system capabilities identified above.

As will be described below, the electrode attachments 43 feature an identification feature within the authentication section of their embedded electronics. The control console 30 is able to authenticate the attached electrode attachment 43 as an approved accessory and identify the electrode type (e.g., monopolar, self-grounding bipolar, etc.). The control console 30, cable accessory 32, and automatic electrode identification enable true "plug and play" functionality. Without the need for changing attachment cables, it is possible for the control console 30 to automatically adapt to the electrode attachments 43, simplifying use thereby reducing the likelihood of use errors.

Figure 13:
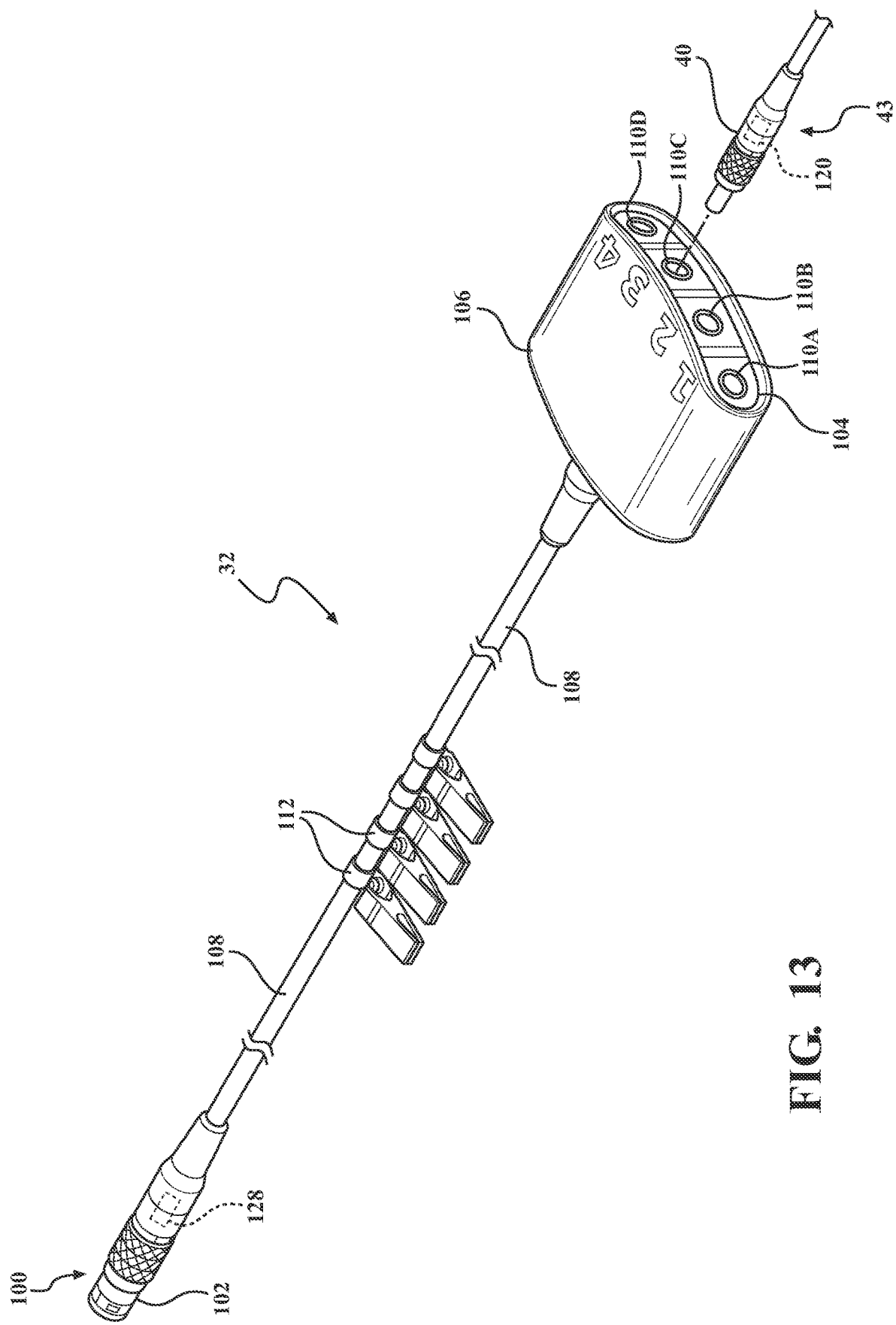
FIG. 13 is a perspective view of the cable accessory in the example of FIG. 1.

The cable accessory 32, according to one example, is shown in FIG. 13. The cable accessory 32 comprises a first interface 100 configured to couple to the control console 30. The first interface 100 connects to the first connection interface 42 of the control console 30, as shown in FIG. 1. The first interface 100, as shown in FIG. 13 comprises an electrical connector 102. In one example, the first interface 100 comprises solely this single connector 102 to simplify connection to the control console 30. In this example, all circuitry that may connect to the first connection interface 42 of the control console 30 is routed through this single connector 102. The connector 102 may be male/female. The first interface 100 may interface with the first connection interface 42 of the control console 30 using any other suitable connection means besides the connector 102 shown.

The cable accessory 32 further comprises a second interface 104 at an opposing end. The second interface 104 is configured to couple to the electrode attachments 43, such as monopolar electrode attachments 43 and/or the bipolar self-grounding electrode attachments 43. In FIG. 13, the second interface 104 is configured to interface with up to four different electrode attachments 43 by providing a plurality of electrical connectors 110A-110D. Each electrical connector 110A-110D is configured to couple to one monopolar electrode attachment 43 or one bipolar self-grounding electrode attachment 43, depending on which electrode attachment 43 is coupled to the electrical connector 110A-110D. The connectors 110A-110D are configured to mechanically and electrically receive the connector 40 of the electrode attachment 43 to provide a secure mechanical and electrical connection. For simplicity, in FIG. 13, one electrode attachment 43 is shown interfacing with electrical connector 110C of the second interface 104, although up to four electrode attachments 43 may be utilized in this example.

In FIG. 13, the cable accessory 32 comprises a housing 106 for storing, e.g., circuitry, wiring, cables, or terminals between the second interface 104 and the first interface 100. The housing 106 may also be provided for aesthetic purposes and for also providing indicia for convenience of the user. An electrical cable 108 is coupled between the housing 106 and the first interface 100. In this example, the second interface 104 is integrated to the housing 106, as shown in FIG. 13. This configuration enables an easily accessible port to couple any of the electrode attachments 43 to the cable accessory 32 at a distance far from the control console 30. As a result, the length of the cables 38 of the electrode attachments 43 potentially may be reduced. It is to be appreciated that in other examples, the first interface 100 may also be integrated into housing 106 thereby reducing the length of the electrical cable 108 or eliminating the electrical cable 108 altogether. In other examples, the cable accessory 32 may be implemented without the housing 106. Instead, the second interface 104 may be bundled together using cable management means. Other configurations between the first interface 100 and second interface 104 are contemplated.

As shown in FIG. 13, the cable accessory 32 may comprise cable management means, such as clips 112 attached to the cable 108. The clips 112 may be slidable along the length of the cable 108 and attachable to objects in the sterile field or outside the sterile field, depending on the location of the cable accessory 32. For instance, the clips 112 may attach directly to a surgical drape to make the second interface 104 accessible or the clips 112 may attach to a feature to secure the cable accessory 32 in place. Any suitable cable management means besides the clips 112 are contemplated.

Figure 14:
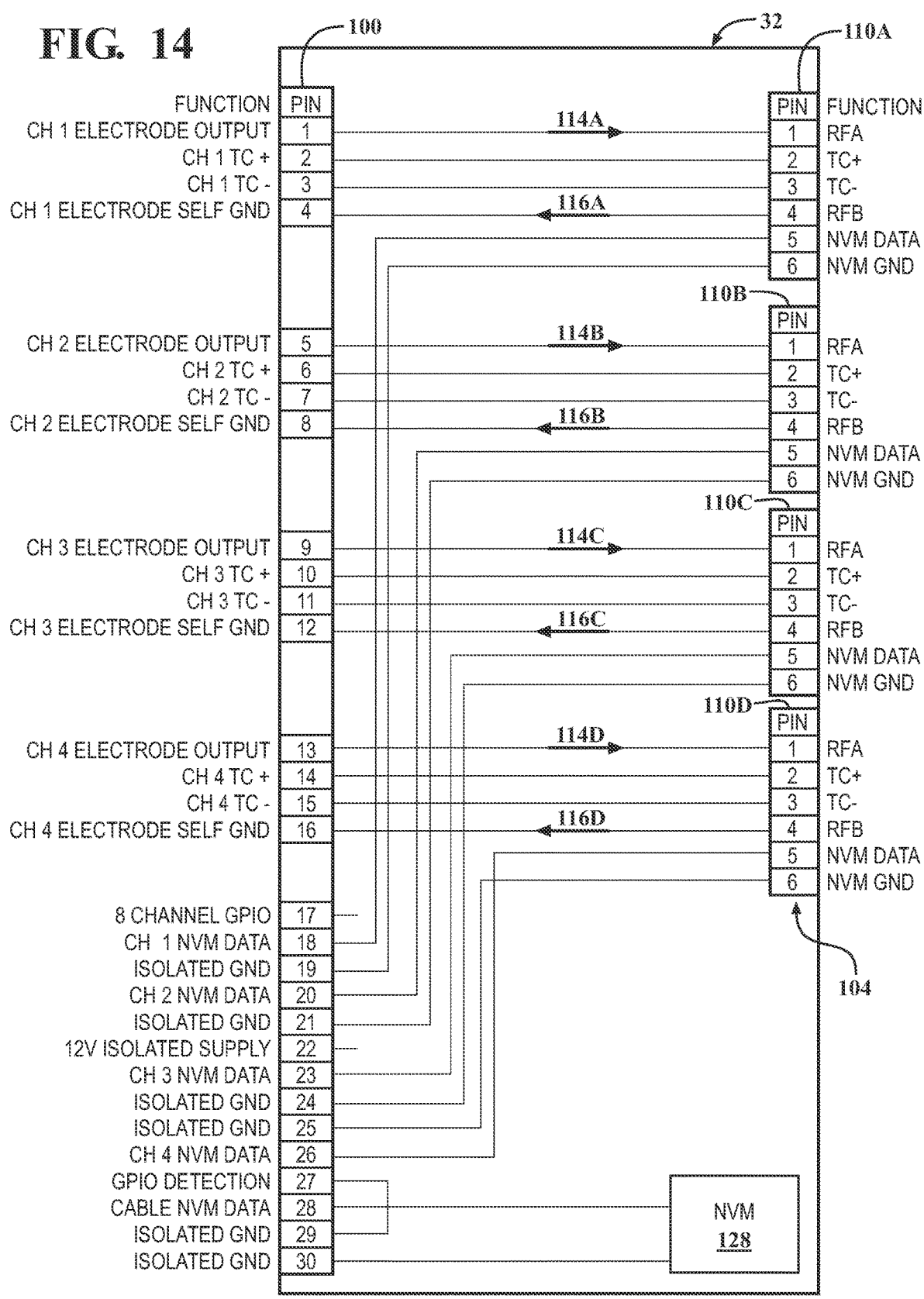
FIG. 14 is a diagram of circuitry of the cable accessory according to one example wherein the cable accessory is passively utilized.

Internal circuitry of the cable accessory 32 according to one example is illustrated in FIG. 14. In this example, the cable accessory 32 is passive, meaning that the cable accessory 32 is not actively powered by a power supply, e.g., to energize active electrical or electronic components therein. Instead, the cable accessory 32 is configured to passively provide the appropriate electrical paths as required by the control console 30.

In FIG. 14, the first interface 100 is represented on the left edge of a box representing the cable accessory 32 and the four separate connectors 110A-110D of the second interface 104 are represented on the right edge of the box representing the cable accessory 32. In this example, the first interface 100 comprises 30 conductive terminals (e.g., pins) and each of the electrical connectors 110A-110D of the second interface 104 comprises an identical number of conductive terminals, which in this example is 6. It is to be appreciated that the first interface 100 and each electrical connectors 110A-110D of the second interface 104 may comprise any suitable number of electrical terminals or pins. Additionally, the pin designation for the first interface 100 and connectors 110A-110D may be different from the pin designations as shown in FIG. 14.

In this example, output circuit paths 114A-114D are each coupled between the first and second interfaces 100, 104 to accommodate signal output from one channel CH1-CH4 of the control console 30 to the respective monopolar electrode attachment 43 or to the bipolar self-grounding electrode attachment 43, depending on which electrode attachment 43 is coupled to the second interface 104. More specifically, for each channel CH1-CH4, each output circuit path 114A-114 is defined between pin 1 (RFA) of each connector 110A-110D of the second interface 104 and pins 1, 5, 9 and 16 (CH_Electrode Output) of the first interface 100, respectively. The output circuit paths 114A-114D may be utilized to transmit the RF output signal for monopolar, parallel bipolar, or bipolar self-grounding configurations.

To accommodate bipolar self-grounding electrode attachments 43, the cable accessory 32 advantageously provides return circuit paths 116A-116D each coupled between the first and second interfaces 100, 104 to accommodate signal return specifically from the bipolar self-grounding electrode attachment 43 to the respective channel of the control console 30 that provided the RF output signal. More specifically, for each channel CH1-CH4, this return circuit path 116A-116 is defined between pin 4 (RFB) of each connector 110A-110D of the second interface 104 and pins 4, 8, 12 and 13 (CH_Electrode Self Gnd) of the first interface 100, respectively.

The return circuit paths 116A-116D are generally not required to be utilized to return the RF output signal for monopolar and parallel bipolar configurations. Thus, these return circuit paths 116A-116D are dedicated for bipolar self-grounding configurations. For example, as explained in previous sections, the ground pad 36 absorbs the RF output signal for monopolar operation, and therefore, the RF output signal is returned to the control console 30 through the ground pad 36 assembly and not returned through the cable accessory 32. It is to be appreciated that although the terms "output" and "return" are utilized herein to describe the circuit paths 114, 116, the signal passing through these paths may be an AC signal, which may alternate current flow direction through any given one of these paths 114, 116. Thus, the signal may be return through the output circuit path 114 and/or may be outputted through the return circuit path 116. Thus, the terms "output" and "return" are utilized for simplicity and are not intended to limit current flow direction.

For parallel bipolar mode, wherein two monopolar electrode attachments 43 are utilized in tandem, the RF output signal is returned through pin 1 (RFA) of another connector 110A-110D of the second interface 104. To illustrate one example for parallel bipolar, and with reference to FIG. 14, the RF output signal may be outputted through circuit path 114B of CH2 to a first of the two monopolar electrode attachments 43. The RF output signal exits pin 1 (RFA) of second interface connector 110B, passes through the target site and returns through pin 1 (RFA) of the second interface connector 110A. Then, the RF output signal passes back to the first interface (pin 1) along circuit path 114A. Thus, although the term "output" has been used to describe output circuits 114A-114D, it is to be appreciated that these circuits 114A-114D may be utilized for signal output or for signal return depending on whether the parallel bipolar configuration is utilized. Notably, this return circuit path (e.g., RFA, circuit 114) for parallel bipolar is different from the return circuit path 116 for the self-grounding bipolar configuration.

In FIG. 14, each second interface connector 110A-110D further comprises a pair of terminals (pin 2, TC+ and pin 3, TC−) for coupling to a thermocouple (not shown) of the electrode attachment. More specifically, for each channel CH1-CH4, a circuit path is defined between pins 2 and 3 (TC+, TC−) of each connector 110A-110D and pins of the first interface 100. Examples of such thermocouples are disclosed in U.S. Pat. No. 8,852,182, granted on Oct. 7, 2014 and entitled "Electrode Assembly with Separate Bipolar Cannula and Supply Electrode," the disclosure of which is hereby incorporated by reference in its entirety. Through the cable accessory 32, the controller 60 sends signals to and returns signals from the thermocouples of each electrode E1-E4. The returned signals are analyzed by the controller 60 for temperature measurement and temperature feedback loops.

Referring back to FIGS. 2 and 13, the electrode attachments 43 comprise a memory device 120, such as a non-volatile memory device (NVM) or erasable programmable read-only memory (EPROM). This memory device 120 may be at any suitable location with respect to the electrode attachment 43, such as within the electrode assembly 34, the cable 38, or the connector 40. In the example shown in FIG. 13, the memory device 120 is within the connector 40 to provide a short electrical path between the memory device 120 and the control console 30. As will be explain in a later section, the memory device 120 of each electrode assembly 43 comprises data stored thereon relating to the electrode assembly 43, such as identification, usage, and authorization/authentication data.

To facilitate transmission of commands for reading data from and/or writing data to the memory device 120 of each electrode attachment 43 connected to the cable accessory 32, each second interface connector 110A-110D further comprises a pair of terminals (pin 5, NVM data and pin 6, NVM ground) for coupling to the memory device 120 of the electrode attachment 43. More specifically, for each channel CH1-CH4, a circuit path is defined between pins 5 and 6 (NVM data, NVM ground) of each connector 110A-110D and pins of the first interface 100. It is desired that this memory device 120 retrieve stored information even after being cycled off and on via the NVM data signal from the control console 30.

Referring to FIGS. 2, 13 and 14, the cable accessory 32 may also comprise a memory device 128, such as NVM or EPROM. This memory device 128 may be at any suitable location with respect to the cable accessory 32, such as within the housing 106, the cable 108, or the connector 102. In the example shown in FIG. 13, the memory device 128 is within the connector 102 at the first interface 100 to provide a short electrical path between the memory device 128 and the control console 30. The memory device 128 of the cable accessory 32 also comprises data stored thereon relating to the cable accessory 32, such as identification, usage, and authorization/authentication data. For example, the memory device 128 may be configured to store identification data associated with the one or more electrode attachments 43 coupled to the second interface 104. The memory device 128 may be configured to store usage data associated with usage of the cable accessory 32 with the control console 30 and/or usage of the cable accessory 32 with the one or more electrode attachments 43. Additionally or alternatively, the memory device 128 is configured to store authentication data associated with authorization of use of the electrode attachment 43 with the cable accessory 32, use of the electrode attachment 43 with the control console 30, and/or use of the cable accessory 32 with the control console 30. Additional details about such data in the memory device 128 are described in later sections.

To facilitate transmission of commands for reading data from and/or writing data to the memory device 128 of the cable accessory 32, the first interface 100 comprises a pair of terminals (pin 28, Cable NVM data and pin 30, Isolated Ground) for coupling the memory device 128 to the controller 60 once the first interface 100 connects to control console 30.

The cable accessory 32 of FIG. 14 provides an additional feature wherein pin 27 (GPIO detection) and pin 29 (isolated ground) are shorted together within the cable accessory 32. This shorting may be implemented by a shorting conductor located anywhere between the first and second interfaces 100, 104. Shorting of these pins enables the controller 60 of the control console 30 to close a circuit internal to the control console 30 once the first interface 100 connects to the first connection interface 42 of the control console 30. Circuitry internal to the control console 30 may include pull-up resistors, and the like, that enable certain signals to be detected upon closure of a circuit accomplished via the shorted pins. The detected signal may be recognized by the controller 60, and in response, the controller 60 is configured to recognize that the cable accessory 32 is indeed coupled to the control console 30. It is to be appreciated that the control console 30 may recognize that the cable accessory 32 is coupled thereto using other means, such as active communication, data transmission, proximity detection, or the like.

Another example of the cable accessory 32' will now be described with respect to FIG. 15, wherein components or features similar to the cable accessory of FIG. 14 are not repeated for simplicity.

Figure 15:
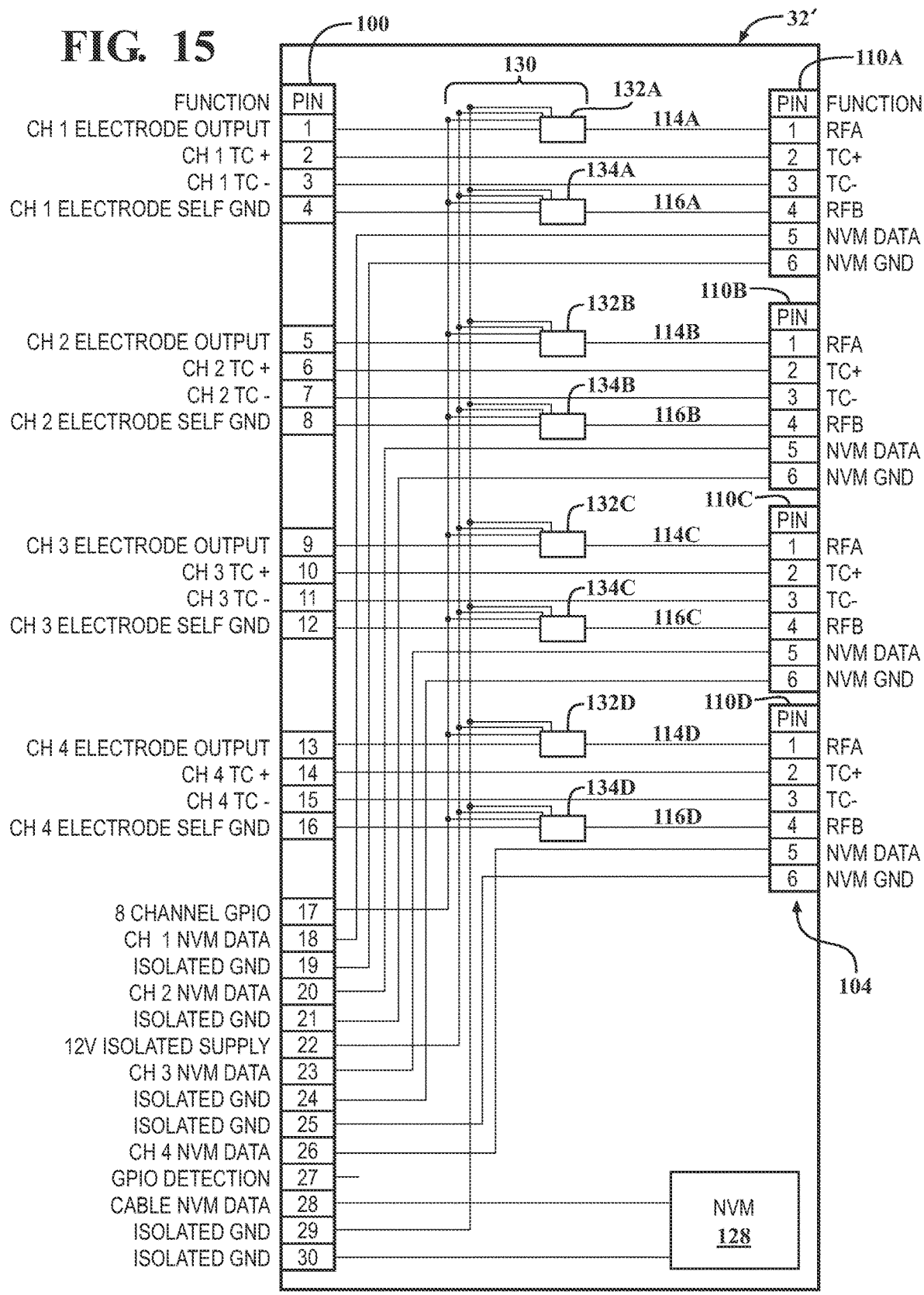
FIG. 15 is a diagram of circuitry of the cable accessory according to another example wherein the cable accessory is actively operable.

Internal circuitry of this example of the cable accessory 32' is illustrated in FIG. 15. In this example, the cable accessory 32' is active, meaning that the cable accessory 32' has access to a power supply, e.g., to energize active electrical or electronic components therein, as will be described. In other words, the cable accessory 32' is configured to provide the appropriate electrical paths as required by the control console 30 by energizing certain components using the supplied power.

The cable accessory 32' in FIG. 15 comprises circuitry coupled between the first and second interfaces 100, 104 similar to that of FIG. 14, but wherein a switch arrangement 130 is further coupled between the first and second interfaces 100, 104. The switch arrangement 130 is controllable to select one or more of a plurality of electrical path configurations between the first and second interfaces 100, 104 to thereby accommodate interconnection between one or more of the described electrode attachments 43 and one or more channels CH1-CH4 of the control console 20.

In FIG. 15, the switch arrangement 130 comprises a first relay 132A-132D disposed in series with each first (output) circuit path 114A-114D to open and close each respective first circuit path 114A-114D. The switch arrangement 130 further comprises a second relay 134A-134D disposed in series with each second (return) circuit path 116A-116D to open and close each respective second circuit path 116A-116D. In some examples, only the first relays 132A-132D may be provided, and not the second relays 134A-134D. In other examples, only the second relays 134A-134D may be provided, and not the first relays 132A-132D. In other examples, to reduce circuitry, a common first relay unit may encompass the functionality of the all the first relays 132A-132D and a second common second relay unit may encompass the functionality of all second relays 134A-134D.

The switch arrangement 130 may be disposed at any suitable location between the first and second interfaces 100, 104. In one example, the switch arrangement 130 is disposed in the housing 106 of the cable accessory 32 to accommodate the first and second relays 132A-132D, 134A-134D.

Figure 16:
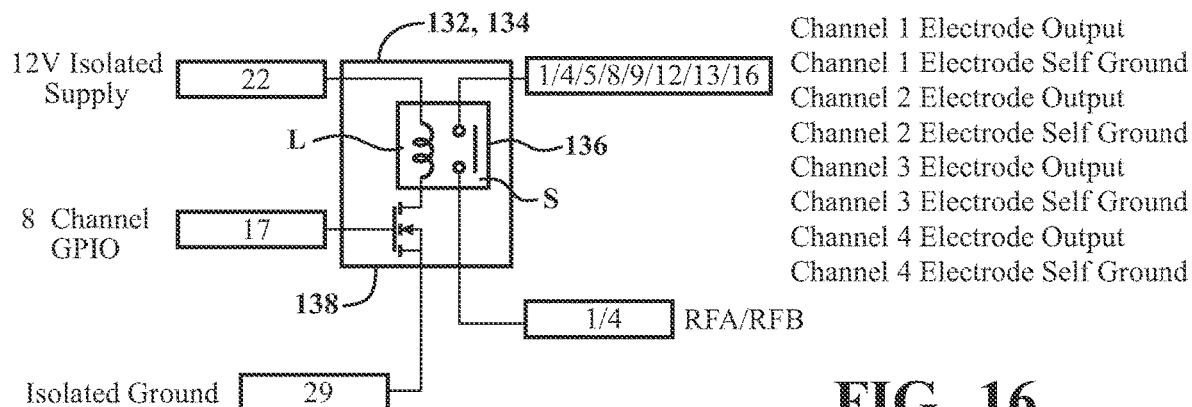
FIG. 16 is a diagram of circuitry of a relay within the actively operated cable accessory of FIG. 15.

As shown in FIG. 15, each of the first and second relays 132A-132D, 134A-134D are connected to the first interface 100 at pin 17 (8 channel GPIO), pin 22 (12V power supply) and pin 29 (Isolated ground). Again, the pin numbers may be different from the pin numbers shown in FIG. 15. In one example, as shown in FIG. 16, showing one example of the internal circuitry, the first and second relays 132A-132D, 134A-134D may each comprise a relay circuit 136, which in this example is an inductor L relay circuit. In the relay circuit 136 is the inductor L, which is configured to magnetically open/close switch S. Each relay 132, 134 comprises a field effect transistor (FET) 138, such as a MOSFET. The 8 channel GPIO pin is provided to energize a gate of the transistor 138. A high side of the inductor L is coupled to the 12V isolated power supply, which is continuously provided by the controller 60. A low side of the inductor L is coupled to the source of the FET 138. A drain of the FET 138 is coupled to the isolated ground for returning electrical current back to the controller 60 in the control console 30. For the first relays 132A-132D, the switch S opens/closes the circuit between the respective channel CH1-CH4 electrode output pin (1, 5, 9, 13) at the first interface 100 and the RFA pin (1) at each respective second interface connector 110A-110D. For the second relays 134A-134D, the switch S opens/closes the circuit between the respective channel CH1-CH4 electrode self-ground pin (4, 8, 12, 16) at the first interface 100 and the RFB pin (4) at each respective second interface connector 110A-110D. When the controller 60 determines that the relay 132, 134 should be closed/opened, the controller 60 controls the 8-Channel GPIO pin at the gate of the FET 138 to energize/de-energize the inductor L, in turn closing/opening the switch S, thereby closing/opening the circuit to enable signal steering. Those skilled in the art appreciate that various other relay configurations are possible besides those described specifically herein.

Using these techniques, the controller 60 is configured to control the switch arrangement 130 to select various electrical path configurations based on the type electrode attachment 43 being utilized (e.g., monopolar, self-grounding bipolar) and the mode that the electrode attachment(s) 43 are being utilized in (e.g., monopolar, parallel bipolar etc.). For instance, the switch arrangement 130 may be controlled to mimic any of the relay configurations described in relation to FIGS. 6-9. For instance, the switch arrangement 130 may be controlled to select an electrical path configuration adapted to interconnect a monopolar electrode attachment 43 and one channel of the control console. With respect to CH1, this may be accomplished, for example by switching on the first relay 132A and switching off the second relay 134A of CH1. In instances where two monopolar electrodes operating in a parallel bipolar mode are connected to second interface connectors, e.g., 110A, 110B (CH1/CH2), the switch configuration 130 may be controlled to switch on first relays 132A, 132B while switching off second relays 134A, 134B. Where the electrode attachment 43 comprises a bipolar self-grounding electrode, connected to CH1, for example, the switch configuration 130 may switch on the first and second relays 132A, 132B of CH1. These techniques may be performed alternative to or in addition to switching of the relays in on the relay section 66, as shown in FIGS. 6-9.

Figure 17:
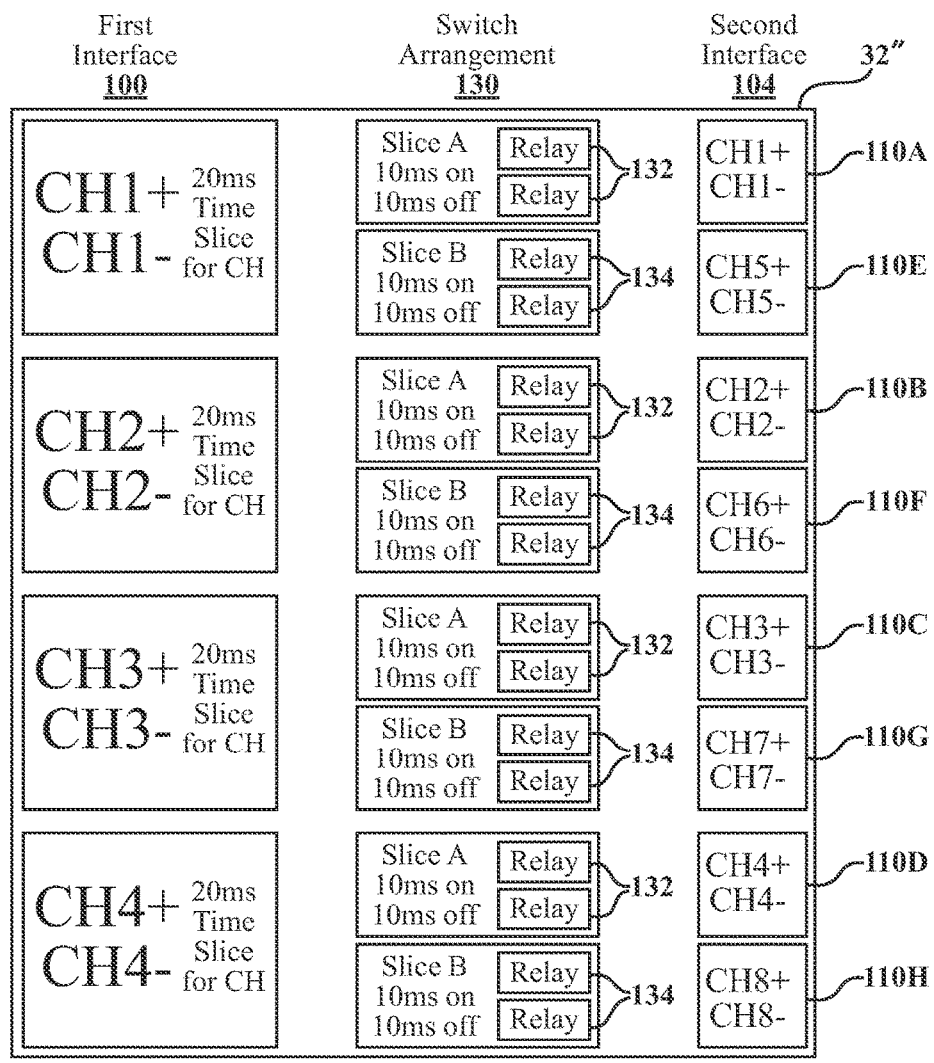
FIG. 17 is a block diagram of another example of the cable accessory being actively operable in accordance with a time slicing technique applied to relays of the cable accessory.
Figure 18:
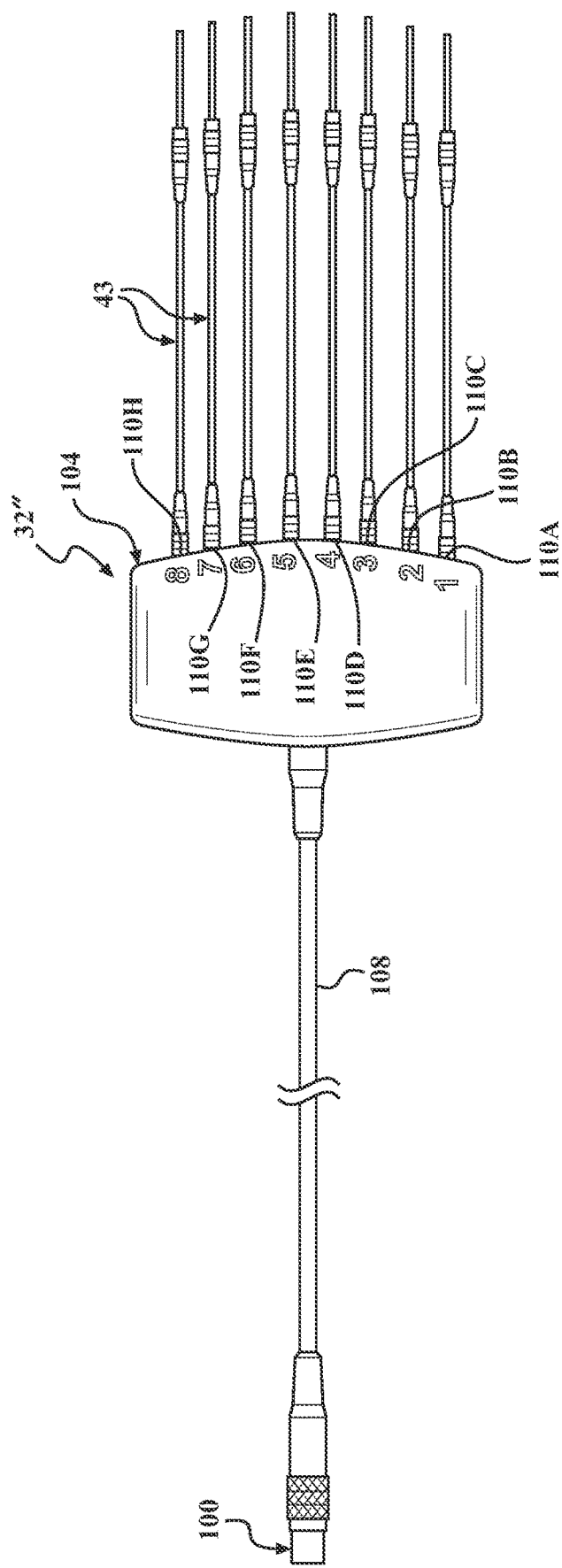
FIG. 18 is a top view of the cable accessory of the example of FIG. 17.

In yet another example of the cable accessory 32", and referring to FIGS. 17 and 18, the first and second relays 132, 134 are subjected to time-slicing and/or sequential control by the controller 60 to enable an increase in the channeling capability of the cable accessory 32. In this example, four channels CH1-CH4 from the control console 30 are still utilized, but the first and second relays 132, 134 are doubled for each channel CH1-CH4. Mainly, two first relays 132 are associated with CH1+ (i.e., CH1 electrode output, pin 1) and two second relays 134 are associated with CH– (i.e., CH1 Electrode self-ground, pin 4). The circuit from CH1+ and CH1– may be spliced to connect to the two first relays 132 and the two second relays 134. The same configuration is presented for CH2-CH4 in FIG. 17.

By providing this configuration, the cable accessory 32 doubles the second interface connectors 110, thereby providing eight separate connectors 110A-110H at the second interface 104, as shown in FIG. 18. Mainly, as shown in FIG. 17, CH1 is doubled to create CH1 and CH5 outputs, CH2 is doubled to create CH2 and CH6 outputs, and so on. This enables the cable accessory 32" and ultimately the electrosurgical system 20 to accommodate twice as many the electrode attachments 43. With shared electrical paths, via splicing of respective CH1-CH4+/−, the configuration of FIG. 17 is enabled by time slicing and sequentially activating and deactivating certain ones of the first and second relays 132, 134. In one example, RF amplifiers 68A-68D for CH1-CH4 are sequentially and non-simultaneously activated for 20 ms time slices. Then, sequentially and non-simultaneously time slicing occurs with respect to the relays 132, 134 of the switching arrangement 130.

For instance, where CH1 and CH5 have monopolar electrode attachments 43, one of the first relays 132 for CH1 is switched on for one portion (e.g., 10 ms—Slice A) of the main CH1 time slice (20 ms), while one of the second relays 134 for CH5 is switched on for the other portion (e.g., the other 10 ms—Slice B) of the main CH1 time slice.

Where CH1 and CH5 have connected among them two monopolar electrode attachments 43 operating in the parallel bipolar configuration, one of the first relays 132 for CH1 and one of the second relays 134 for CH5 are switched on for one portion (e.g., 10 ms) of the main CH1 time slice, while the other first relay 132 for CH1 and the other second relay 134 for CH5 are switched on for the other portion (e.g., the other 10 ms) of the main CH1 time slice.

Where bipolar self-grounding electrode attachments 43 are connected to CH1 and CH5, both the first relays 132 for CH1 are switched on for one portion (e.g., 10 ms) of the main CH1 time slice, while both of the second relays 134 for CH5 are switched on for the other portion (e.g., the other 10 ms) of the main CH1 time slice.

The technique described with respect to CH1/CH5 may be performed equally with respect to the remaining channels CH2/CH6, CH3/CH7, CH4/CH8 in FIG. 17. Furthermore, any type of time slicing configuration or timing may be utilized, including, but not limited to those configurations described in section II above. Again, these techniques may be performed alternative to or in addition to switching of the relays in on the relay section 66, as shown in FIGS. 6-9. Furthermore, methods for operating the cable accessories 32, 32' 32" are supported herein by virtue of the functionality of the same.

IV. Stimulation and Impedance Verification and Calibration Techniques

Figure 19:
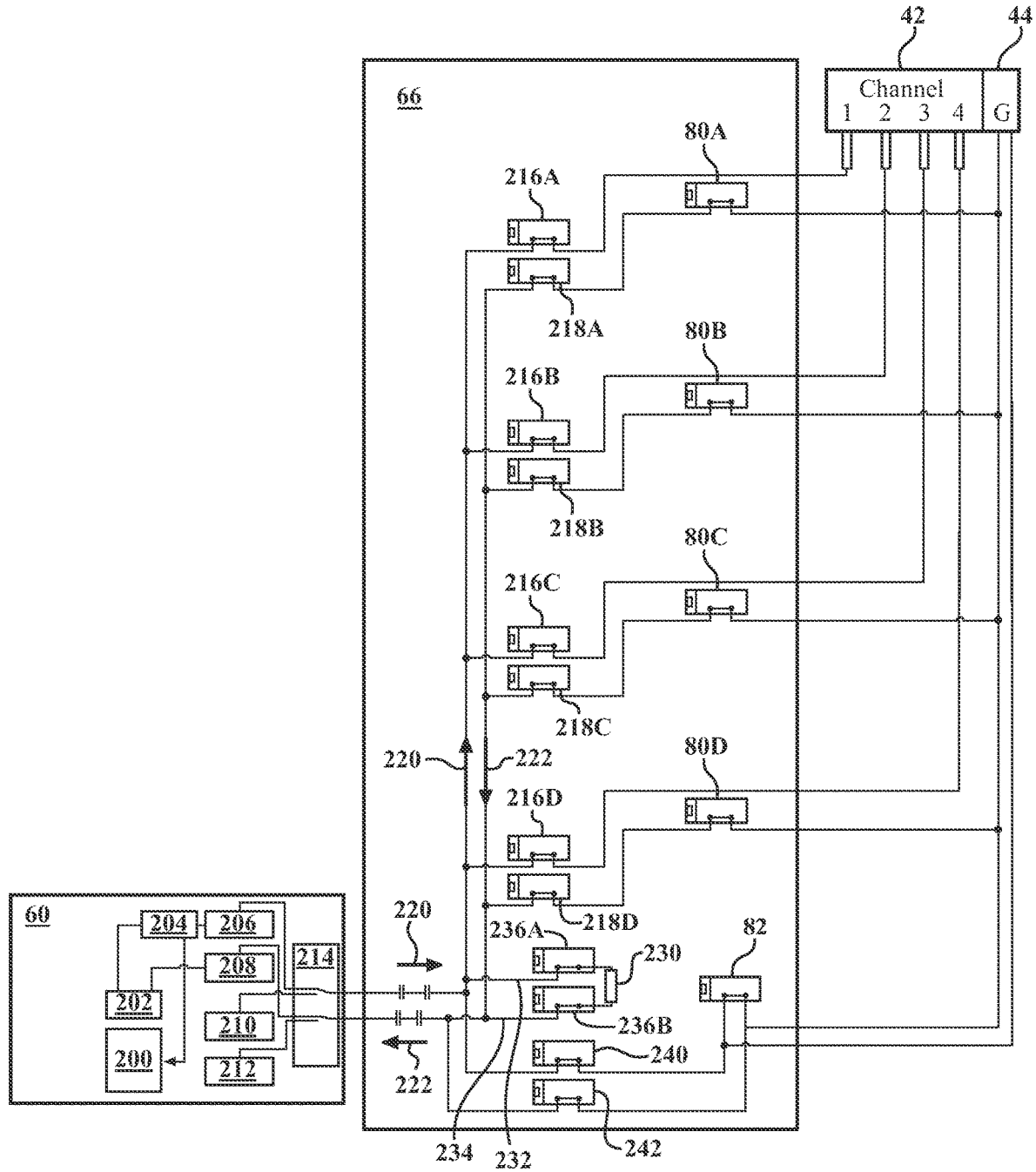
FIG. 19 is a circuit diagram of components of the control console being configured to enable stimulation and impedance verification and calibration according to one example.

With reference to FIG. 19, provided are techniques for verification and/or calibration of the stimulation and impedance signals provided by the control console 30. As described above, these stimulation signals comprise a sensory stimulation signal and a motor stimulation signal.

This technique will be described in reference to FIG. 19, by first introducing of components of the controller 60 and the relay section 66, which are shown to enable the technique. The controller 60 comprises and/or implements a microcontroller 200, a digital-to-analog converter (DAC) 202, a sensing circuit 204, a stimulation (motor or sensory) generator (shown by 206 representing STIM V(+) and 208 representing STIM (V−)), an impedance generator (shown by 210 representing impedance Z(+) and 212 representing impedance Z(−)), and a multiplexing circuit 214. In one example, the microcontroller 200 is an impedance converter network analyzer IC. However, the microcontroller 200 may have other configurations.

The stimulation generator 206, 208 is configured to respectively output and return the stimulation signal. The impedance generator 210, 212, respectively, is configured to output and return the impedance signal. The controller 60 or microcontroller 200 controls the stimulation generator 206, 208 and the impedance generator 210, 212 for generating the respective stimulation and impedance signals.

In one example, the stimulation signal is a biphasic DC signal and the impedance signal is an AC signal. In one example, stimulation signal has an amplitude that is adjustable from +/−0.0 volts to +/−10.0 volts maximum, via the DAC 202. The impedance measurement signal is a controlled output impedance AC signal with frequency of 30 KHz, and with amplitude of 0.5 volts, for example. The controller 60 or microcontroller 200 interfaces to a Serial Peripheral Interface (SPI) bus addressable the DAC 202. The DAC 202 is configured to provide a software controlled output waveform with amplitude limits of +/−10 volts DC.

Software on the controller 60 or microcontroller 200 directly controls the operation of the DAC 202, thereby enabling the generation of the sensory nerve and motor nerve stimulation signals. The output of the DAC 202 is routed through a buffer amplifier in order to improve waveform slew-rate and provide current-limit control. The buffered output from the DAC 202 is then routed through circuit 214 for the purposes of multiplexing the stimulation waveform signal with the impedance measurement signal.

The sensing circuit 204 is provided for the stimulation signals and in one example is implemented by the microcontroller 200 and a current sensing resistor. The microcontroller 200 is provided as a second sensing circuit in relation to the impedance signals, as will be described below.

Additional components of the relay section 66 are also shown in FIG. 19 to implement the technique. Specifically, the relay section 55 comprises a stimulation/impedance output relay 216A-216D is coupled between the controller 60 and the first connection interface 42 of the control console 30, which connects to the cable accessory 32, if applicable. Each stimulation/impedance output relay 216A-216D is configured to selectively switch on/off connection between the controller 60 and the first connection interface 42. For example, switching on each stimulation/impedance output relay 216A-216D may be performed when the respective channel CH1, CH2, CH3, CH4 is utilized by the control console 30 during the sensory or motor stimulation signal delivery and/or impedance measurement, but not during RF output. The stimulation/impedance output relays 216A-216D are controlled by switching signals provided by the controller 60 and/or the relay section 66. The stimulation/impedance output relays 216A-216D may be any suitable type of relays, such as inductive load drivers, reed relays, or the like.

A stimulation/impedance return relay 218A-218D is coupled between the controller 60 and the second connection interface 44 of the control console 30, which connects to the connector 46 for the ground pad 36. Each stimulation/impedance return relay 218A-218D is configured to selectively switch on/off connection between the second connection interface 42 and the controller 60. Just as with the stimulation/impedance output relays 216A-216D, switching on each stimulation/impedance return relay 218A-218D may be performed when the respective channel CH1, CH2, CH3, CH4 is utilized by the control console 30 during the sensory or motor stimulation signal delivery and/or impedance measurement, but not during RF output. The stimulation/impedance return relays 218A-218D are controlled by switching signals provided by the controller 60 and/or the relay section 66. The stimulation/impedance return relays 218A-218D may be any suitable type of relays.

The ground pad relay 80A-80D for each channel CH1-CH4, described above is also utilized for this technique. The ground pad relays 80A-80D are activated because a return path from the ground pad 36 is needed during sensory or motor stimulation signal delivery and/or impedance measurement. With each ground pad relay 80A-80D closed, a closed circuit is formed during sensory or motor stimulation modes and/or impedance measurement.

By switching on these relays 216, 218, 80 for each channel CH1-CH4, an output circuit path 220 is defined between the stimulation generator 206, STIM (V+) and the first connection interface 42 to enable sending of the stimulation signals from the stimulation generator 206 to the one or more electrode attachments 43 through the first connection interface 42. Similarly, a return circuit path 222 is defined between the second connection interface 44 and the stimulation generator 208, STIM (V−) to enable return of the stimulation signals to the stimulation generator 208 from the one or more electrode attachments 43, through the ground pad 36, and through the second connection interface 44. This process is conducted similarly for each respective channel CH1, CH2, CH3, CH4 having electrode attachments 43 connected thereto for operating in the stimulation modes.

The output circuit path 220 further enables sending of the impedance signals from the impedance generator 210, impedance Z(+), to the one or more electrode attachments 43 through the first connection interface 42. Similarly, the return circuit path 222 enables return of the impedance signals to the impedance generator 212, impedance Z(−) from the one or more electrode attachments 43, through the ground pad 36, and through the second connection interface 44. This process is conducted similarly for each respective channel CH1, CH2, CH3, CH4 having electrode attachments 43 connected thereto for receiving impedance signals.

It is to be appreciated that although the terms "output" and "return" are utilized herein to describe the circuit paths 220, 222, the signal passing through these paths is may be an AC signal, which may alternate current flow direction through any given one of these paths 220, 222. Thus, the signal may be return through the output circuit path 220 and/or may be outputted through the return circuit path 222. Thus, the terms "output" and "return" are utilized for simplicity and are not intended to limit current flow direction.

Since the ground pad 36 is connected to the control console 30 for this technique, the relay section 66 utilizes the ground pad testing relay 82. As described, low impedance situations trigger actuation of the ground pad testing relay 82.

Further provided on the relay section 66 is a calibration element 230. In one example, the calibration element 230 is a calibration resistor, such as precision resistor. In one example, the calibration resistor has a rating of 246 Ohms with a low tolerance, e.g., ±0.1%. The calibration element 230 may be other types besides a resistor. For example, the calibration element 230 may be other passive electrical components, such as calibration capacitor. Alternatively, the calibration element 230 may be a network of electrical components. Furthermore, the calibration element 230 may be an active calibration device.

A calibration output circuit path 232 is defined between one end of the calibration element 230 and the output circuit path 220. A calibration return circuit path 234 is defined between the other end of the calibration element 230 and the return circuit path 222. At least one calibration relay 236 is coupled between the calibration element 230 and the output circuit path 220 or between the calibration element 230 and the return circuit path 222. In FIG. 19, two calibration relays 236A, 236B are provided in series with respect to these respective calibration circuit paths 232, 234. Although only one calibration relay 236 may be utilized, two calibration relays 236A, 236B may be provided for redundancy purposes to ensure proper connection or disconnection of the calibration element 230. The calibration relay 236 is controlled by switching signals provided by the controller 60 and/or the relay section 66. The calibration relay 236 may be any suitable type of relay.

With continued reference to FIG. 19, the relay section 66 further comprises a ground pad stimulation/impedance output relay 240 and a ground pad stimulation/impedance return relay 242. The ground pad stimulation/impedance output relay 240 is coupled between the output circuit path 220 and one end of the ground pad testing relay 82. The ground pad stimulation/impedance return relay 242 is coupled between the other end of the ground pad testing relay 82 and the return circuit path 222. These output and return relays 240, 242 are switched on to measure impedance with respect to the ground pad 36, and are generally switched off when the stimulation/impedance output and return relays 216, 218 are switched on.

With the aforementioned components introduced, techniques for stimulation and impedance calibration and verification will now be described. This calibration/verification technique, according to one example, is performed during a self-test program that is executed by the control console 30. The self-test may be performed at any suitable time, such as at boot-up of the control console 30. Alternatively, the self-test may be performed during operation of the control console 30.

First, with respect to verification and calibration for impedance, the output and return relays 240, 242 associated with the calibration element 230 are switched on. In one example, the stimulation/impedance output and return relays 216, 218 are switched off during this process. Thus, in this example, the calibration element 230 is used for this calibration step not for impedance measurement with respect to the patient-circuit. In an alternative example, the stimulation/impedance output and return relays 216, 218 are switched on such that impedance calibration and verification may occur on-the-fly during patient-circuit impedance measurement.

The controller 60 controls the multiplexing circuit 214 to enable the multiplexing circuit 214 to selectively couple the impedance generator 210, 212 to the output and return circuit paths 220, 222. The controller 60 confirms proper connection of the calibration element 230 to the circuit by techniques, such as sending a test signal through the calibration element 230 and analyzing the test signal.

Once the calibration element 230 is confirmed to be properly connected, the impedance generator 210 outputs the impedance signal at the command of the controller 60 or microcontroller 200. The impedance signal passes through the output circuit path 220 and calibration output circuit path 232. The calibration element 230 receives the impedance signal. In instances where the calibration element 230 is the precision resistor, the precision resistor receives the impedance signal by enabling electrical current of the impedance signal to pass through the precision resistor. After passing through the calibration element 230, the impedance signal passes through the through calibration return circuit path 234 and the return circuit path 222 and returns through the multiplexing circuit 214 back to the impedance generator 212.

Return of the impedance signal produces readings or measurements that may be analyzed. The sensing circuit for impedance, which is implemented by microcontroller 200, is configured to analyze readings associated with the returned impedance signal to assess whether the impedance load is purely resistive in view of the precise resistance of the calibration element 230 or whether the impedance load further comprises inductive and capacitive components. If the impedance load is not purely resistive, the sensing circuit for impedance (e.g., microcontroller 200) is calibrated to compensate for the detected inductive and capacitive components. The microcontroller 200 may be configured to calibrate itself internally or a different component on the controller 60 may command calibration of the microcontroller 200. In one example, calibration involves adjusting a sensitivity of the sensing circuit of the microcontroller 200. Calibration values may be stored in memory 56 and analyzed to formulate best-guess calibration of the microcontroller 200. It is to be appreciated that impedance sensing circuits other than the microcontroller 200 may be implemented without departing from the scope of this technique.

Calibration of the microcontroller 200 results in improved impedance signal measurements that are more purely resistive and accurate. As such, when impedance measurement signals are eventually utilized during motor or sensory stimulation modes, the impedance sensing circuit will be verified and calibrated for proper operation. This allows the patient-circuit impedance to be more precisely measured. The application of both stimulation waveforms and RF energy are restricted to a finite range of patient-circuit impedance values (e.g., 38 ohm to 1800 ohms). Therefore, this technique importantly provides accurate patient-circuit impedance measurement.

Now verification and calibration for motor or sensory stimulation, will be addressed, which in one example occurs after impedance verification and calibration. Here, the output and return relays 240, 242 associated with the calibration element 230 are switched on or remain on. In one example, the stimulation/impedance output and return relays 216, 218 are switched off during this process. Thus, in this example, the calibration element 230 is used for this calibration step not for patient stimulation. In an alternative example, the stimulation/impedance output and return relays 216, 218 are switched on such that stimulation calibration and verification may occur on-the-fly during motor or sensory stimulation of the patient.

Notably, the same calibration element 230 is utilized for both the impedance and the stimulation verification/calibration. The controller 60 controls the multiplexing circuit 214 to enable the multiplexing circuit 214 to selectively switch from the impedance generator 210, 212 to the stimulation generator 206, 208, to enable connection between the stimulation generator 206, 208 and the output and return circuit paths 220, 222. Thus, multiplexing the impedance signal and the stimulation signal occurs in order to accomplish stimulation current sense calibration. The utility of the impedance measurement function is improved through the use of this selectable circuit path through the calibration element 230 for stimulation verification. Testing proper connection of the calibration element 230 may be repeated or may be assumed based on successful testing during impedance calibration and verification.

The stimulation generator 206 outputs the stimulation signal at the command of the controller 60 or microcontroller 200. The stimulation signal passes through the output circuit path 220 and calibration output circuit path 232. The calibration element 230 receives the stimulation signal. In instances where the calibration element 230 is the precision resistor, the precision resistor receives the stimulation signal by enabling electrical current of the stimulation signal to pass through the precision resistor. After passing through the calibration element 230, the stimulation signal passes through the through calibration return circuit path 234 and the return circuit path 222 and returns through the multiplexing circuit 214 back to the stimulation generator 208.

Return of the stimulation signal produces readings or measurements that may be analyzed. Specifically, the sensing circuit 204 for stimulation, which is implemented in one example by the microcontroller 200 and a current sense resistor. The sensing circuit 204 is configured to analyze readings associated with the returned stimulation signal. In general, the sensing circuit 204 for stimulation is not required to be utilized for impedance because of the inherent difference between the impedance and stimulation signals. In one example, the stimulation signal passes through the current sense resistor of the sensing circuit 204 thereby generating an electrical current reading, which in turn is correlated to a corresponding voltage signal. The controller 60 or the microcontroller 200 asses the voltage signal readings, for example, by comparing the readings to a predetermined value or a predetermined range of values.

If the readings are not as expected, the sensing circuit 204 is calibrated. The microcontroller 200 may be configured to calibrate itself internally or a different component on the controller 60 may command calibration of the microcontroller 200. In one example, calibration entails modifying a sensitivity value of the sensing circuit 204. Calibration of this sensing circuit 204 enables precise confirmation of actual stimulation current value. Calibration values may be stored in memory 56 and analyzed to formulate best-guess calibration of the sensing circuit 204. This stimulation assurance function is able to detect when insufficient current, or no current, is delivered to the patient while performing the stimulation functions. Calibration of the sensing circuit 204 results in more accurate stimulation signal measurement and generation.

The controller 60 or microcontroller 200 may further be configured to analyze the readings to determine whether a stimulation fault has occurred during output of the stimulation signal. This technique advantageously confirms proper delivery of stimulation energy to the patient. This also provides improved ability to detect faults in the electrical stimulation circuitry or stimulation waveform routing circuitry that would otherwise be undetected, thereby decreasing the likelihood that a physician may proceed with a nerve ablation procedure based upon faulty patient feedback.

The controller 60 is configured to communicate with the one or more processors 54 of the control console 30 enabling the communication or display of appropriate communications or messages relating to the status or outcome of the verification and calibration techniques described herein for stimulation and impedance.

The described verification and calibration techniques may be utilized using components other than those described herein and the steps of these techniques may occur in an order or manner different than but functionally equivalent to the order or manner described.

V. Accessory Identification, Odometer and Associated Database

Referring initially to FIG. 2, techniques are described herein relating to processing data stored on the electrode attachments 43 and/or the cable accessory 32 and providing such data for display on the GUI 52.

As described, the control console 30 comprises the display 50, the controller 60, and the one or more processors 54. The control console 30 further comprises the first connection interface 42 configured to either directly receive the cable accessory 32 and electrode attachments 43 or to directly receive the electrode attachments 43 (without the cable accessory 32).

As also described, referring to FIGS. 2, 13 and 14, the electrode attachments 43 each comprise the memory device 120 and the cable accessory 32 comprises the memory device 128. These memory devices 120, 128 may be any suitable type of memory such as NVM or EPROM. The first connection interface 42 facilitates connection between the controller 60 of the control console 30 and the memory devices 120, 128 of these attachments 32, 43, respectively.

In one example, transmission data, or transmissions of commands for reading data from and/or writing data to the memory devices 120, 128 is accomplished by a 1-wire communication protocol. Each memory device 120, 128 may be connected by a 1-wire signal wire (e.g., see FIG. 14, CH_NVM Data, Cable NVM) and a ground wire (e.g., see FIG. 14, isolated ground). The 1-wire signal wire returns to the controller 60 for analysis. Any other communication protocol or technique may be utilized to establish connection between the control console 30 controller 60 and the memory devices 120, 128.

As shown in FIG. 2, these memory devices 120, 128 according to one example, each comprise data associated with the each respective attachment 32, 43. In one example, these memory devices 120, 128 comprise various data fields. In FIG. 2, only a few of these data fields are illustrated, namely, identification data 300, usage data 302 and authentication data 304.

The identification data 300 is data that identifies the respective attachment 32, 43 to the controller 60. Identification data 300 may comprise a data structure with various identifying information about the attachment 32, 43. For example, the identification data 300 may comprise a name field comprising data identifying the type of attachment 32, 43. A part number field may contain part number data of the attachment 32, 43. The serial number of the attachment 32, 43 may be separately stored. These data may be used to inhibit use of the attachment 32, 43. This may be necessary if data received from another source informs the control console 30 that the particular attachment 32, 43 should not be used. A manufacturer field may also be provided that identifies the manufacturer of the attachment 32, 43. A device type data field may contain information regarding the type of attachment 32, 43 (e.g., cable accessory, self-grounding bipolar, monopolar, etc.)

For the electrode attachments 43, the usage data 302 relates to usage of each respective electrode attachment 43. Such usage data 302 may identify usage of the electrode attachment 43 with the control console 30 (and any other control consoles) and/or usage of the electrode attachment 43 with the cable accessory 32 (and any other cable accessories). For the cable accessory 32, usage data 302 identifies usage of the cable accessory 32 with the control console 30 (or any other control console) and/or usage of the cable accessory 32 with electrode attachments 43 coupled thereto.

The usage data 302 regulates the operation of the respective attachment 32, 43. The attachment 32, 43 are reusable and/or sterilizable components. The usage data 302 indicates the number of times the respective attachment 32, 43 can be used before it should be subjected to a maintenance overhaul or discarded. With this usage data 302, the number of times electrodes E1-E4 or electrode attachments 43 have undergone disconnection from the control console 30, and therefore sterilization, can be captured. The usage data 302 may also contain data indicating the maximum overall number of times the respective attachment 32, 43 can be used. Since these respective attachment 32, 43 are designed for multiple uses, the usage data 302 is provided to prevent over use of the respective attachment 32, 43 beyond useable life. For these reasons, the usage data 302 may also be referred to as odometer data.

In one example, the usage data 302 structure contains a series of "n" bits, where "n" is the maximum value able to be counted. Initially all of the data bits are set ("1"). This corresponds to an odometer value of zero. Each time the cable attachment 32, 43 is plugged into the control console 30, the counter is incremented by one and the first non-zero bit encountered in the data structure is cleared by the controller 60. Decoding of the odometer involves the controller 60 counting the number of bits that have been cleared. Usage data 302 may contain other data and may be manipulated using techniques other than those described herein.

In regards to authentication data 304, this is associated with authorization of use of the attachment 32, 43. For example, only authorized cable accessories 32 and electrode attachments 43 may be utilized with authorized control consoles 30, and vice-versa. Similarly, only authorized electrode attachments 43 may be utilized with authorized cable accessories 32, and vice-versa. Authentication data 304 may be utilized in conjunction with the identification data 300. For example, the part number of the attachment 32, 43 may identify the attachment 32, 43 to the control console 30 with regard to a registry. Authentication data 304 may also include data listing the part numbers of the companion components with which the particular components may or may not be used. Another function of the authentication data 304 may be to identify the attachment 32, 43 type to the control console 30. For example, the self-grounding electrode attachment 43 has different operating requirements than a monopolar attachment 43, which requires the use of the ground pad 36. Various other configurations of authentication data 304 may be utilized other than those described herein.

Examples of identification data 300, usage data 302, and authentication data 304 as well as other data fields for memory devices of electrode attachments are disclosed in U.S. Pat. No. 8,852,182, granted on Oct. 7, 2014 and entitled "Electrode Assembly with Separate Bipolar Cannula and Supply Electrode," the disclosure of which is hereby incorporated by reference in its entirety. It is to be appreciated that more or less data fields may be provided on the memory devices 120, 128. Examples of such data fields may include hardware versions, operating or control data, physical parameters of the attachment 32, 43 (e.g., electrode length of the attachments 43), and the like.

The control console 30 advantageously provides new techniques for processing and displaying representations of the data 300 and the usage data 302 associated with attachments 32, 43. Mainly, the non-transitory memory 56 of the control console 30 has stored thereon computer executable instructions 58 (hereinafter referred to as software), which is executable by the one or more processors 54. The software 58 may be implemented also in conjunction with the controller 60. The software 58 may implement an operating system of the control console 30 that implements the GUI 52 and user control thereof.

The software 58 reads and stores the identification data 300 and usage data 302 associated with the attachments 32, 43 received at the first connection interface 42 of the control console 30. Advantageously, by storing this data, the control console 30 retains identification data 300 and usage data 302 for attachments 32, 43 that are, or have been, connected to the control console 30 over time. This time may be the life of the control console 30. Thus, this identification data 300 and usage data 302 may be received at different times throughout the life of the control console 30. The memory 56 is configured to retain the identification data 300 and usage data 302 associated while the attachments 32, 43 are connected to the interface 42, and even after the attachments 32, 43 are disconnected from the interface 42.

A database 320 in the memory 56 of the control console 30 may store identification data 300 and usage data 302 for any and all attachments 32, 43 that are or have been connected to the control console 30. This database 320 enables the control console 30 to implement an inventory of the attachments 32, 43 for purposes such as preventative maintenance, inventory management, usage management, error logging, and the like.

The software 58 implements techniques to process the stored identification data 300 and usage data 302. Mainly, the identification data 300 and usage data 302 as read by the controller 60 generally are received piecemeal over time. As such, the software 58 is configured to process the stored identification data 300 and usage data 302 by organizing the identification data 300 and usage data 302 in the cumulative database 320. This may be accomplished by compiling similar types of data, arranging data by timestamps, and categorizing data into certain bins of the database 320. Various other types of advanced processing by the software of the identification data 300 and usage data 302 are contemplated, such as sorting, concatenating, filtering, and the like.

In some examples, the databases 320 for a fleet of control consoles 30 may be complied into a remote database for data mining purposes for a facility, for example. Having the ability to first store this data locally on each control console 30, as provided by the techniques described herein, are an advantageous first step for data mining.

Furthermore, the software 58 is configured to instruct processing of stored identification data 300 and usage data 302 by transforming the stored identification and usage data into text. Mainly, the identification data 300 and usage data 302 as read by the controller 60 generally are not in a form suitable for display. The identification data 300 and usage data 302 may be in a certain digital representation, e.g., binary or ASCII. The identification data 300 and usage data 302 are processed to create text and/or images that are understood by the operating system of the control console 30 and suitable for the GUI 52. For example, the software 58 may instruct additional characters or words to be added to or associated with the identification data 300 and usage data 302 to provide additional meaning. This processing may be according to any suitable technique, such as character-encoding schemes using a table of stored characters or words, and the like. It is to be appreciated that although processing, e.g. organizing and transforming, has been described relative to identification data 300 and usage data 302, any other type of data may be similarly processed.

Referring now to FIGS. 20-23, the software 58 instructs the generation of the digital representation 310 of the processed identification data 300 and usage data 302 for the display 50.

Figure 20:
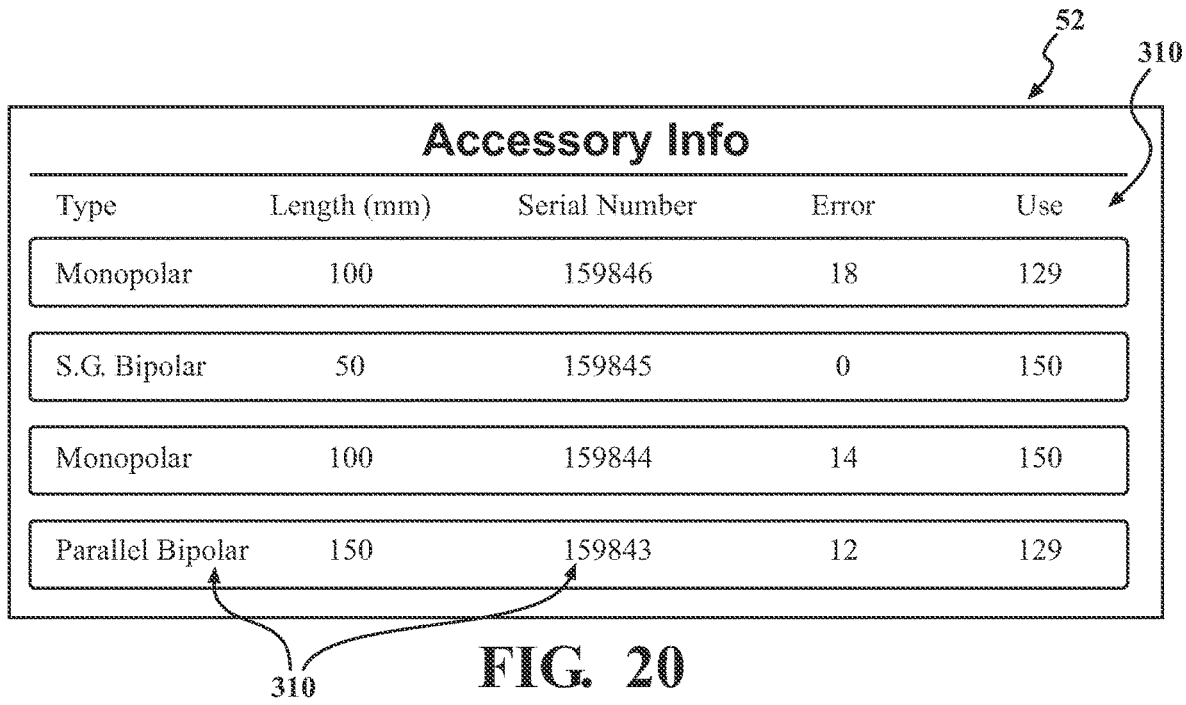
FIG. 20 is a sample view of a graphical user interface displayable on a display of the control console showing identification, usage, and error data for various electrode attachments that are coupled to or have been coupled to the control console, according to one example.

FIG. 20 is a view of one example screen of the GUI 52 displayable on the display 50 of the control console 30 showing data for various electrode attachments 43 that are coupled to or have been coupled to the control console 30. For simplicity, the display 50 itself is not shown, although it is understood that the GUI 52 is displayed thereon. This screen relates specifically to the electrode attachments 43 rather than the cable accessory 32. The screen may be selected by the user interfacing with the GUI 52, using e.g., touch screen or the like.

In FIG. 20, the type of each electrode attachment 43 is displayed showing, e.g., monopolar, self-grounding bipolar, and those electrode attachments 43 operating in parallel bipolar mode. This may be derived from the processed identification data 300. A length of each electrode attachment 43 is also displayed on the digital representation 310 showing a length of the respective electrode E1-E4. Since electrodes E1-E4 may be various lengths, users may not know whether the same or different electrodes E1-E4 have been used. Representing this data provides users with greater insight about whether electrodes E1-E4 may be failing. The processed usage data 302 is utilized to derive usage of each electrode attachment 43 to display with the digital representation 310. Here, the processed usage data 302 is represented as an integer denoting how many times the electrode attachments 43 have been used.

The controller 60 is also configured to detect operating errors 330 associated with the attachments 32, 43. For example, with respect to the electrode attachments 43, electrodes E1-E4 may approach the ground pad 36 too closely. In such situations, low impedance triggers actuation of the ground pad testing relay 82. The controller 60 may either store this error in memory 56 or write error data in the memory device 120 of the respective electrode attachment 43. Various other types of operating errors 330 may associated with the electrode attachments 43. Similar can be said for the cable accessory 32. The control console 30 is configured to associate the operating error 330 with the identification data 300 associated with the respective attachment 32, 43. The software 58 may instruct processing and generation of the digital representation 310 to further include the associated operating error 330 for the display 50. One derivation of the digital representation 310 of the associated operating error 330 is shown in FIG. 20 wherein an integer number of operating errors 330 associated with each electrode attachments 43 is displayed.

Figure 21:
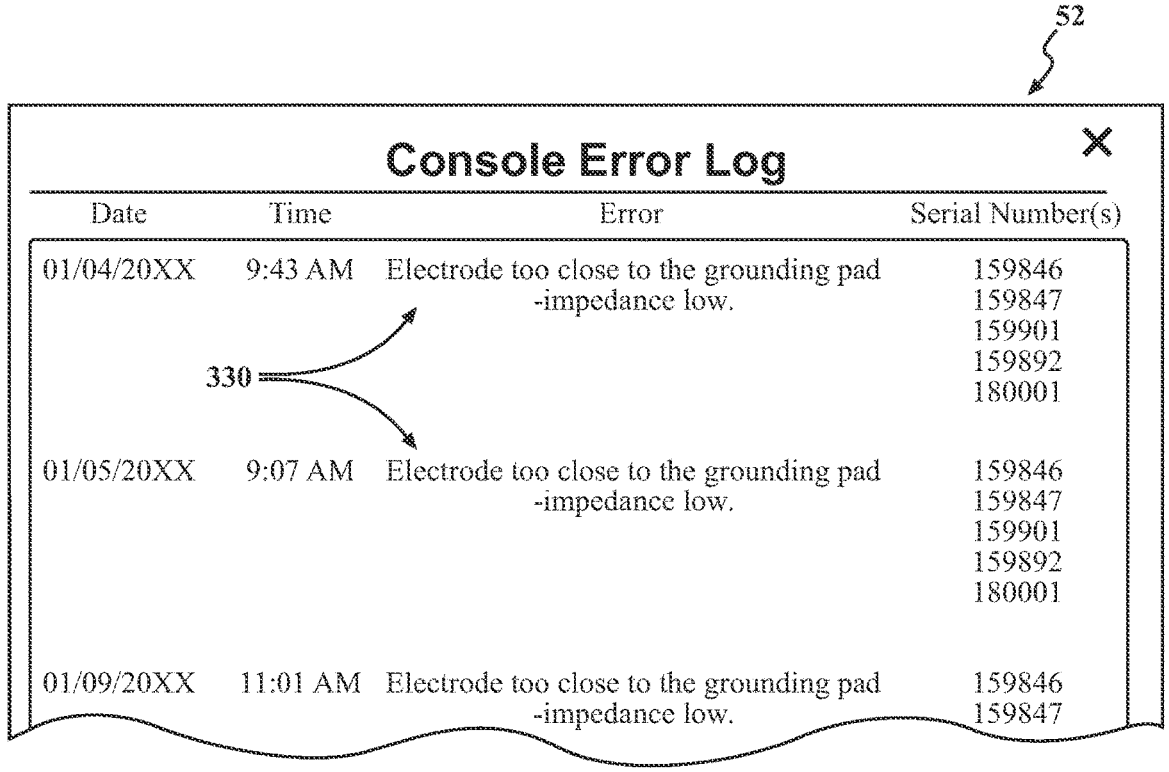
FIG. 21 is a sample view of the graphical user interface showing an error log for the control console with respect to electrode attachments that are coupled to or have been coupled to the control console, according to one example.

FIG. 21 is a view of another example screen of the GUI 52 displayable on the display 50 of the control console 30 showing an error log for the control console 30, as a whole, with respect to electrode attachments 43 that are coupled to or have been coupled to the control console 30. Here, the processed identification data 300 is digitally represented by serial numbers that have been organized during processing by associated operating error 330. The operating errors 330 in this example relate to low impedance from the electrode E1-E4 being too close to the ground pad 36. Of course, other operating errors 330 may be digitally represented. A time stamp is associated with either use of the control console 30 or the triggering of the operating error 330. The log keeps track of any of such operating errors 330 to enable a user of the control console 30 to access this data about the control console 30 quickly. The GUI 52 may provide any other suitable type of data about the control console 30 other than that shown in FIG. 21.

The GUI 52 further provides the ability to select data about any given attachment 43, 32 that has been connected to the control console 30. The aforementioned processing of the identification data 300 and usage data 302 enables dynamic and quick transition between these various GUI 52 screens showing different layers of data.

Figure 22:
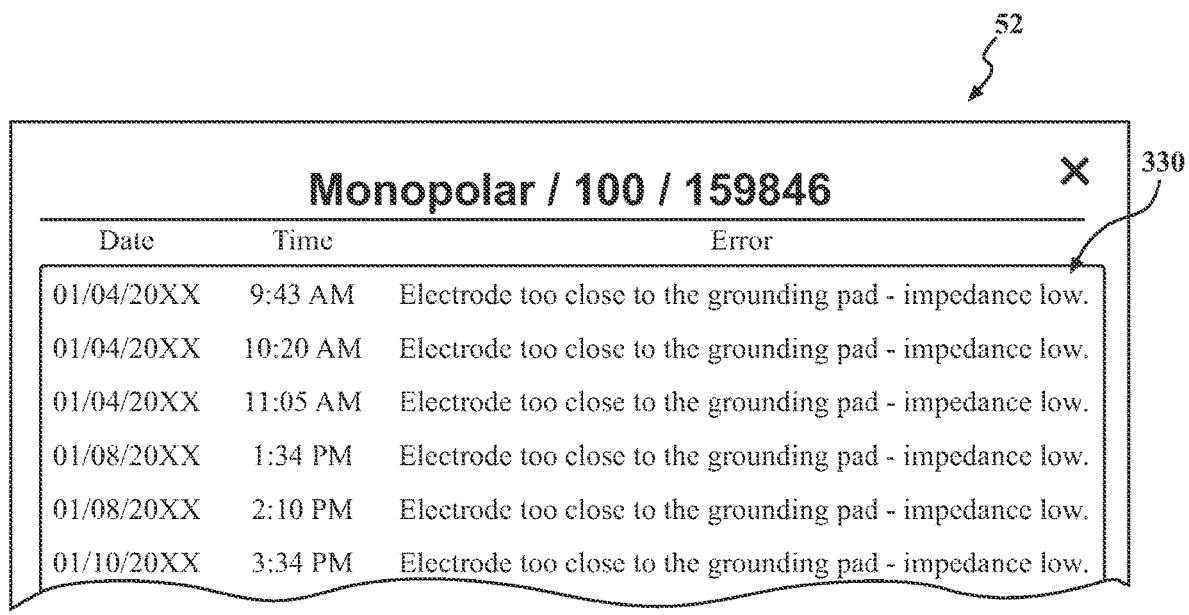
FIG. 22 is a sample view of the graphical user interface showing an error log for a selected electrode attachment that is coupled to or has been coupled to the control console, according to one example.

In the example of FIG. 22, the digital representation 310 provides data for one electrode attachment 43, namely, a monopolar electrode attachment having 100 mm length and a serial number derived from the processed identification data 300. Again, the selected electrode attachment 43 either is coupled to or has been coupled to the control console 30. Contrary to the error log of the control console 30 shown in FIG. 21, the error log in FIG. 22 is provided solely for this respective electrode attachment 43. The operating errors 330 in this example again relate to low impedance from the electrode of this electrode attachment 43 being too close to the ground pad 36. Of course, other operating errors 330 for the electrode attachment 43 may be digitally represented. A time stamp associated with either use of the electrode attachment 43 or the triggering of the operating error 330 is also displayed. The log keeps track of any of such operating errors 330 to quickly enable a user of the control console 30 to access data about any single electrode attachment 43. The GUI 52 may provide any other suitable type of data associated with any given electrode attachment 43 other than that shown in FIG. 22. Furthermore, the log of FIG. 22 may be provided for the cable accessory 32 as well.

Figure 23:
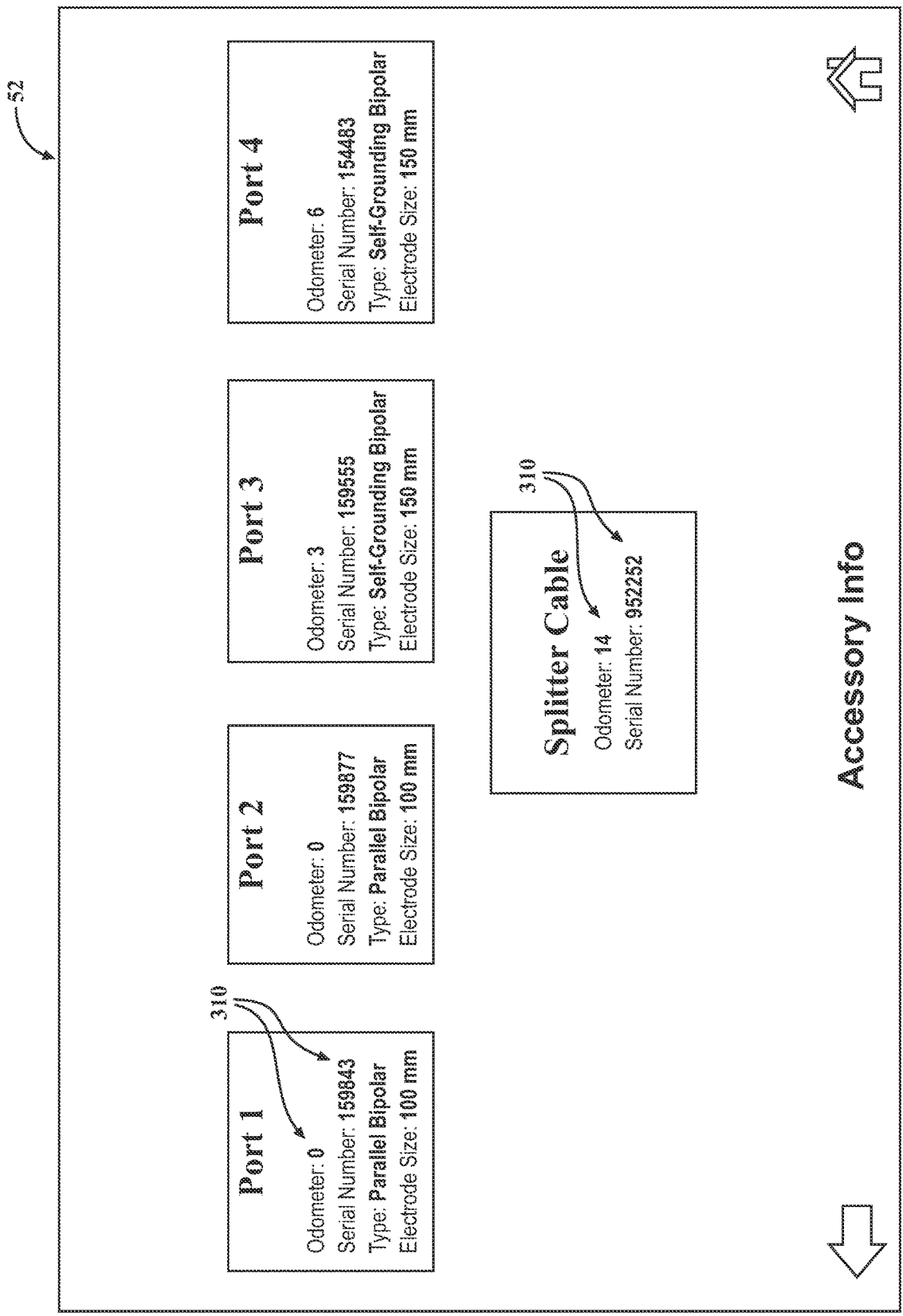
FIG. 23 is a sample view of the graphical user interface showing a summary of the cable accessory and respective electrode attachments coupled to the cable accessory, according to one example.

FIG. 23 is yet another example screen shot of the GUI 52 showing a selectable summary page for the cable accessory 32. Again, this may be for a currently connected cable accessory 32 or a cable accessory 32 that has been previously connected to the control console 30. The identification data 300 and usage data 302 of the cable accessory 32 have been processed into the digital representation 310 respectively showing the serial number and usage (odometer) of the cable accessory 32. Further displayed is processed data for electrode attachments 43 that are connected to the cable accessory 32 (e.g., at the second interface 104 of the cable accessory 32). Namely, the identification data 300 and usage data 302 of each electrode attachment 43 has been processed into the digital representation 310 respectively showing the serial number, type, length, and usage (odometer) of each electrode attachment 43. The GUI 52 may enable nested selection within screens. For example, in FIG. 23, each port of the cable accessory 32 may be selected to show further information about each respective electrode attachment 43 beyond that shown in FIG. 23. The GUI 52 may provide any other suitable type of data associated with the cable accessory 32 or connected electrode attachments 43 other than that shown in FIG. 23. Furthermore, the log of FIG. 22 may be provided for the cable accessory 32 as well.

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

Embodiments of the disclosure can be described with reference to the following numbered CLAUSES, with specific features laid out in the dependent clauses:

I. A cable accessory configured to interconnect a monopolar electrode attachment and/or a bipolar self-grounding electrode attachment to a control console, the control console being configured to energize one or more of the electrode attachments through one or more channels to perform radio frequency (RF) nerve ablation, the cable accessory comprising:
a first interface configured to couple to the control console;
a second interface configured to couple to the monopolar electrode attachment and/or the bipolar self-grounding electrode attachment;
an output circuit path coupled between the first and second interfaces to accommodate signal output from one channel of the control console to the monopolar electrode attachment or to the bipolar self-grounding electrode attachment, depending on which electrode attachment is coupled to the second interface;
a first return circuit path coupled between the first and second interfaces to accommodate signal return from the bipolar self-grounding electrode attachment to the one channel of the control console.

II. The cable accessory of clause I wherein the first interface comprises a single electrical connector coupled the output circuit path and the first return circuit path.

III. The cable accessory of any one of clauses I and II wherein the second interface comprises a plurality of electrical connectors each being configured to couple to one monopolar electrode attachment or one bipolar self-grounding electrode attachment, depending on which electrode attachment is coupled to the electrical connector.

IV. The cable accessory of clause III wherein each of the electrical connectors of the second interface comprises an identical number of conductive terminals.

V. The cable accessory of any one of clauses III and IV wherein each electrical connector of the second interface comprises:
one terminal coupled to the output circuit path to accommodate the signal output;
one terminal coupled to the first return circuit path to accommodate signal return from the bipolar self-grounding electrode attachment;
a pair of terminals for coupling to a thermocouple of the electrode attachment; and
a pair of terminals for coupling to a non-volatile memory of the electrode attachment.

VI. The cable accessory of any one of clauses I-V further comprising a housing and an electrical cable coupled between the housing and the first interface, and wherein the second interface is integrated to the housing.

VII. The cable accessory of any one of clauses I-VI further being configured to interconnect two monopolar electrode attachments in a parallel bipolar mode to the control console, and wherein:
the second interface is configured to couple to the two monopolar electrode attachments;
the output circuit path is configured to accommodate signal output from one channel of the control console to a first of the two monopolar electrode attachments; and
a second return circuit path being different from the first return circuit path is coupled between the first and second interfaces to accommodate signal return from a second of the two monopolar electrode attachments to another channel of the control console.

VIII. The cable accessory of any one of clauses I-VII further comprising a non-volatile memory.

IX. The cable accessory of clause VIII wherein the non-volatile memory is configured to store identification data associated with the one or more electrode attachments coupled to the second interface.

X. The cable accessory of any one of clauses VIII and IX wherein the non-volatile memory is configured to store usage data associated with usage of the cable accessory with the control console and/or usage of the cable accessory with the one or more electrode attachments.

XI. The cable accessory of any one of clauses VIII-X wherein the non-volatile memory is configured to store authentication data associated with authorization of use of one or more of:
the electrode attachment with the cable accessory;
the electrode attachment with the control console; and
the cable accessory with the control console.

XII. A cable accessory configured to interconnect one or more electrode attachments to a control console, the control console being configured to energize the one or more electrode attachments through one or more channels to perform radio frequency (RF) nerve ablation, said cable accessory comprising:
a first interface configured to couple to the control console;
a second interface configured to couple to the one or more electrode attachments; and
a circuit coupled between the first and second interfaces and comprising a switch arrangement being controllable to select one or more of a plurality of electrical path configurations between the first and second interfaces to thereby accommodate interconnection between the one or more electrode attachments and the one or more channels of the control console.

XIII. The cable accessory of clause XII wherein the first interface comprises a single electrical connector being connectable to all selected electrical path configurations.

XIV. The cable accessory of any one of clauses XII and XIII wherein the second interface comprises a plurality of electrical connectors each being configured to couple to one electrode attachment and wherein the electrode attachment further comprises a type defined as any one of a monopolar electrode attachment and bipolar self-grounding electrode attachment, and wherein the second interface is configured to accommodate any one of the types of electrode attachments, depending on which type of electrode attachment is coupled to the second interface.

XV. The cable accessory of clause XIV wherein each of the electrical connectors of the second interface comprises an identical number of conductive terminals.

XVI. The cable accessory of any one of clauses XIV and XV wherein:
each of the electrical connectors of the second interface comprises a first terminal and a second terminal each configured to accommodate RF signal transmission to or from one channel;
a first circuit path is defined between each first terminal and the first interface; a second circuit path is defined between each second terminal and the first interface; and
wherein the switch arrangement comprises a first relay disposed in series with each first circuit path to open and close each first circuit path and a second relay disposed in series with each second circuit path to open and close each second circuit path.

XVII. The cable accessory of clause XVI wherein the first and second relays of each connector of the second interface are sequentially controllable.

XVIII. The cable accessory of any one of clauses XII-XVII wherein the electrode attachment further comprises a type defined as any one of a monopolar electrode attachment and bipolar self-grounding electrode attachment and wherein the switch arrangement is controllable based on the type of the electrode attachment.

XIX. The cable accessory of any one of clauses XII-XVIII wherein the switch arrangement is controllable to select the electrical path configuration based on the electrode attachment being a monopolar electrode attachment such that the selected electrical path configuration is adapted to interconnect the monopolar electrode attachment and one channel of the control console.

XX. The cable accessory of any one of clauses XII-XIX wherein the switch arrangement is controllable to select the electrical path configuration based on two electrode attachments being two monopolar electrode attachments operating in a parallel bipolar mode such that the selected electrical path configuration is adapted to interconnect the two monopolar electrode attachments and two channels of the control console.

XXI. The cable accessory of any one of clauses XII-XX wherein the switch arrangement is controllable to select the electrical path configuration based on the electrode attachment being a bipolar self-grounding electrode attachment such that the selected electrical path configuration is adapted to interconnect the bipolar self-grounding electrode attachment and one channel of the control console.

XXII. The cable accessory of any one of clauses XII-XXI wherein the circuit further comprises a non-volatile memory coupled to the controller and wherein the non-volatile memory is configured to store one or more of:
identification data associated with the one or more electrode attachments coupled to the second interface;
usage data associated with usage of the cable accessory with the control console and/or usage of the cable accessory with the one or more electrode attachments; and
authentication data associated with authorization of use of the one or more electrode attachments with the control console and/or cable accessory.

XXIII. The cable accessory of any one of clauses XII-XXII wherein the controller and switch arrangement are disposed in a housing and further comprising an electrical cable coupled between the housing and the first interface and wherein the second interface is integrated to the housing.

XXIV. A control console configured for radio frequency (RF) nerve ablation, comprising:
a display;
a controller;
one or more processors;
an interface configured to receive attachments adapted for RF nerve ablation and to facilitate connection between a memory device of each attachment and the controller, each memory device having stored thereon identification data identifying the attachment and usage data identifying usage of the attachment; and
a non-transitory memory having stored thereon instructions, which when executed by the one or more processors, are configured to:
read and store the identification and usage data associated with the attachments received at the interface;
process the stored identification and usage data; and
generate a digital representation of the processed identification and usage data for the display.

XXV. The control console of clause XXIV wherein the instructions are configured to read and store the identification and usage data associated with the attachments received at the interface at different times to generate a cumulative database of the stored identification and usage data.

XXVI. The control console of clause XXV wherein the instructions are configured to process the stored identification and usage data by organizing the stored identification and usage data in the cumulative database.

XXVII. The control console of any one of clauses XXIV-XXVI wherein the instructions are configured to process the stored identification and usage data by transforming the stored identification and usage data into text.

XXVIII. The control console of any one of clauses XXIV-XXVII wherein each memory device further has stored thereon authentication data associated with authorization of use of the attachment and wherein the instructions are further configured to read the authentication data associated with the attachments received at the interface.

XXIX. The control console of any one of clauses XXIV-XXVIII wherein one or more of the attachments are an electrode attachment.

XXX. The control console of any one of clauses XXIV-XXIX wherein one or more of the attachments are a cable accessory being configured to interconnect one or more electrode attachments to the control console.

XXXI. The control console of clause XXX wherein the usage data is further associated with usage of the cable accessory with the control console and/or usage of the cable accessory with the one or more electrode attachments.

XXXII. The control console of any one of clauses XXIV-XXXI wherein the instructions are further configured to:
detect an operating error;
associate the operating error with the identification data associated with the attachment; and
further generate the digital representation to include the associated operating error for the display.

XXXIII. The control console of any one of clauses XXIV-XXXII wherein the controller is further configured to command writing of usage data to the memory device of one or more of the attachments.

XXXIV. The control console of any one of clauses XXIV-XXXII wherein the non-transitory memory is configured to retain the identification and usage data associated with the attachments after the attachments are disconnected from the interface.

XXXV. The control console of any one of clauses XXIV-XXXIV further comprising a housing wherein the controller, one or more processors, and non-transitory memory are disposed within the housing and wherein the display and the interface are coupled to the housing and exposed to an exterior of the housing.

XXXVI. The control console of any one of clauses XXIV-XXXV further comprising an RF generator configured to generate RF signals being transmittable to one or more of the attachments through the interface.

XXXVII. A method for operating a control console configured for radio frequency (RF) nerve ablation, the control console comprising a display, a controller, and an interface configured to receive attachments adapted for RF nerve ablation, each attachment comprising a memory device having stored thereon identification data identifying the attachment and usage data identifying usage of the attachment, the method comprising the control console performing the steps of:
reading the identification and usage data associated with the attachments from the memory devices;
storing the identification and usage data;
processing the stored identification and usage data;
generating a digital representation of the processed identification and usage data; and
displaying the digital representation with the display.

XXXVIII. The method of clause XXXVII wherein:
reading the identification and usage data is further defined as reading the identification and usage data associated with the attachments received at the interface at different times;
storing the identification and usage data is further defined as storing the identification and usage data from the memory devices of the attachments at different times to generate a cumulative database of the stored identification and usage data; and
generating the digital representation is further defined as generating the digital representation of the stored identification and usage data from the cumulative database.

XXXIX. The method of clause XXXVIII wherein processing the stored identification and usage data further comprises organizing the stored identification and usage data in the cumulative database.

XL. The method of any one of clauses XXXVII-XXXIX wherein processing the stored identification and usage data further comprises transforming the stored identification and usage data into text.

XLI. The method of any one of clauses XXXVII-XL wherein each memory device further has stored thereon authentication data associated with authorization of use of the attachment and wherein the control console is configured to read the authentication data associated with the attachments received at the interface.

XLII. The method of any one of clauses XXXVII-XLI wherein one or more of the attachments is an electrode attachment.

XLIII. The method of any one of clauses XXXVII-XLII wherein one or more of the attachments is a cable accessory for interconnecting one or more electrode attachments to the control console.

XLIV. The method of any one of clauses XXXVII-XLIII wherein the usage data is further associated with usage of the cable accessory with the control console and/or usage of the cable accessory with the one or more electrode attachments.

XLV. The method of any one of clauses XXXVII-XLIV further comprising the control console:
detecting an operating error;
associating the operating error with the identification data associated with the attachment; and
further generating the digital representation to include the operating error for the display.

XLVI. The method of any one of clauses XXXVII-XLV further comprising the control console commanding writing of usage data to the memory device of one or more of the attachments.

XLVII. The method of any one of clauses XXXVII-XLVI further comprising retaining, in memory, the identification and usage data associated with the attachments after the attachments are disconnected from the interface.

XLVIII. The method of any one of clauses XXXVII-XLVII further comprising transmitting RF signals from an RF generator of the control console to one or more of the attachments through the interface.

The invention claimed is:

1. A control console configured for radio frequency (RF) nerve ablation, the control console comprising:
a plurality of channels;
a plurality of RF amplifiers each being dedicated to deliver energy to a corresponding one of the channels;
a plurality of DC power supplies each being dedicated to a corresponding one of the RF amplifiers;
a plurality of power supply relays each being coupled between one of the DC power supplies and an input of the dedicated corresponding one of the RF amplifiers; and
a controller coupled to the RF amplifiers and being configured to:
apply switching signals to control each of the power supply relays to selectively switch on and off connections between the DC power supplies and the dedicated corresponding RF amplifiers; and
apply control signals to each RF amplifier sequentially, one at a time, to deliver energy separately and independently to each of the corresponding channels.

2. The control console of claim 1, further comprising a plurality of output relays each being coupled between one of the channels and an output of the dedicated corresponding one of the RF amplifiers.

3. The control console of claim 2, wherein the controller is further configured to apply the switching signals to each of the output relays to selectively switch on and off connections between the channels and the dedicated corresponding RF amplifiers.

4. The control console of claim 1, further comprising a plurality of return relays each being coupled to an output of a respective one of the RF amplifiers.

5. The control console of claim 4, further comprising a connection interface, and a plurality of ground pad relays each being coupled between the connection interface and a corresponding one of the return relays such that each of the return relays is coupled to the connection interface via a bipolar relay.

6. The control console of claim 5, wherein the connection interface is configured to be coupled to a ground pad.

7. The control console of claim 5, wherein the controller is further configured to apply the switching signals to each of the ground pad relays to selectively switch on and off connections between the connection interface and the return relays.

8. The control console of claim 4, further comprising a plurality of bipolar relays each being coupled between one of the channels and a respective one via a bipolar relay.

9. The control console of claim 8, wherein the controller is further configured to apply the switching signals to each of the bipolar relays to selectively switch on and off connections between the channels and the return relays via the bipolar relays.

10. A method for controlling a control console comprising a plurality of channels, a plurality of radio frequency (RF) amplifiers each dedicated to a corresponding one of the channels, a plurality of DC power supplies each dedicated to a corresponding one of the RF amplifiers, a plurality of power supply relays each being coupled between one of the DC power supplies and an input of the dedicated corresponding one of the RF amplifiers, and a controller coupled to the RF amplifiers, the method comprising:
applying, with the controller, switching signals to control each of the power supply relays to selectively switch on and off connections between the DC power supplies and the dedicated corresponding RF amplifiers; and
applying, with the controller, control signals to each RF amplifier sequentially, one at a time, to deliver energy separately and independently to each of the corresponding channels.

11. The method of claim 10, further comprising a plurality of output relays each being coupled between one of the channels and an output of the dedicated corresponding one of the RF amplifiers, the method further comprising applying, with the controller, the switching signals to each of the output relays to selectively switch on and off connections between the channels and the dedicated corresponding RF amplifiers.

12. The method of claim 11, wherein the control console further comprises a plurality of return relays each being coupled to an output of a respective one of the RF amplifiers.

13. The method of claim 12, further comprising a connection interface, and a plurality of ground pad relays each being coupled between the connection interface and a corresponding one of the return relays, and wherein the method further comprises apply, with the controller, the switching signals to each of the ground pad relays to selectively switch on and off connections between the connection interface and the return relays.

14. The method of claim 13, further comprising establishing a connection between the connection interface and a ground pad.

15. The method of claim 12, wherein the control console further comprises further comprising a plurality of bipolar relays each being coupled between one of the channels and a respective one via a bipolar relay, and wherein the method further comprises applying, with the controller, the switching signals to each of the bipolar relays to selectively switch on and off connections between the channels and the return relays via the bipolar relays.

16. The method of claim 12, wherein the control console further comprises a plurality of self-grounding relays each being coupled between one of the channels and an output of the dedicated corresponding one of the RF amplifiers, and wherein the method further comprises of applying, with the controller, the switching signals to each of the self-grounding relays to selectively switch on and off connection the channels and the return relays via the self-grounding relays.

17. A control console configured for radio frequency (RF) nerve ablation, the control console comprising:
a plurality of channels;
a plurality of RF amplifiers each being dedicated to deliver energy to a corresponding one of the channels;
a plurality of DC power supplies each being dedicated to a corresponding one of the RF amplifiers;
a plurality of power supply relays each being coupled between one of the DC power supplies and an input of the dedicated corresponding one of the RF amplifiers; and
a plurality of self-grounding relays each being coupled between one of the channels and an output of the dedicated corresponding one of the RF amplifiers; and
a controller coupled to the RF amplifiers and being configured to:
apply switching signals to control each of the power supply relays to selectively switch on and off connections between the DC power supplies and the dedicated corresponding RF amplifiers; and
apply the switching signals to each of the self-grounding relays to selectively switch on and off connections between the channels and return relays.

18. The control console of claim 17, wherein the controller is further configured to apply control signals to each RF amplifier sequentially, one at a time, to deliver energy separately and independently to each of the corresponding channels.

19. The control console of claim 17, further comprising a plurality of output relays each being coupled between one of the channels and an output of the dedicated corresponding one of the RF amplifiers.

20. The control console of claim 19, wherein the controller is further configured to apply the switching signals to each of the output relays to selectively switch on and off connections between the channels and the dedicated corresponding RF amplifiers.

* * * * *